US009890408B2

(12) United States Patent
Eshoo et al.

(10) Patent No.: US 9,890,408 B2
(45) Date of Patent: Feb. 13, 2018

(54) MULTIPLE DISPLACEMENT AMPLIFICATION

(75) Inventors: Mark W. Eshoo, Solana Beach, CA (US); John Picuri, San Diego, CA (US); Curtis Phillipson, San Diego, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 12/905,819

(22) Filed: Oct. 15, 2010

(65) Prior Publication Data

US 2011/0118151 A1     May 19, 2011

Related U.S. Application Data

(60) Provisional application No. 61/252,065, filed on Oct. 15, 2009.

(51) Int. Cl.
| | | |
|---|---|---|
| *C12Q 1/64* | (2006.01) | |
| *C12P 19/34* | (2006.01) | |
| *C12Q 1/68* | (2018.01) | |

(52) U.S. Cl.
CPC ............ *C12P 19/34* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 4,075,475 | A | 2/1978 | Risby et al. |
| 4,683,195 | A | 7/1987 | Mullis et al. |
| 4,683,202 | A | 7/1987 | Mullis |
| 4,965,188 | A | 10/1990 | Mullis et al. |
| 5,015,845 | A | 5/1991 | Allen et al. |
| 5,043,272 | A * | 8/1991 | Hartley .......................... 435/5 |
| 5,072,115 | A | 12/1991 | Zhou |
| 5,143,905 | A | 9/1992 | Sivasubramanian et al. |
| 5,213,961 | A | 5/1993 | Bunn et al. |
| 5,219,727 | A | 6/1993 | Wang et al. |
| 5,288,611 | A | 2/1994 | Kohne |
| 5,436,129 | A | 7/1995 | Stapleton |
| 5,451,500 | A | 9/1995 | Stapleton |
| 5,472,843 | A | 12/1995 | Milliman |
| 5,476,774 | A | 12/1995 | Wang et al. |
| 5,484,908 | A | 1/1996 | Froehler et al. |
| 5,502,177 | A | 3/1996 | Matteucci et al. |
| 5,503,980 | A | 4/1996 | Cantor |
| 5,504,327 | A | 4/1996 | Sproch et al. |
| 5,504,329 | A | 4/1996 | Mann et al. |
| 5,523,217 | A | 6/1996 | Lupski et al. |
| 5,527,669 | A | 6/1996 | Resnick et al. |
| 5,527,675 | A | 6/1996 | Coull et al. |
| 5,547,835 | A | 8/1996 | Koster |
| 5,556,772 | A | 9/1996 | Sorge et al. |
| 5,567,587 | A | 10/1996 | Kohne |
| 5,576,204 | A | 11/1996 | Blanco et al. |
| 5,580,733 | A | 12/1996 | Levis et al. |
| 5,605,798 | A | 2/1997 | Koster |
| 5,608,217 | A | 3/1997 | Franzen et al. |
| 5,612,179 | A | 3/1997 | Simons |
| 5,622,824 | A | 4/1997 | Koster |
| 5,625,184 | A | 4/1997 | Vestal et al. |
| 5,639,606 | A | 6/1997 | Willey |
| 5,641,632 | A | 6/1997 | Kohne |
| 5,645,985 | A | 7/1997 | Froehler et al. |
| 5,683,869 | A | 11/1997 | Ramsay Shaw et al. |
| 5,686,242 | A | 11/1997 | Bruice et al. |
| 5,691,141 | A | 11/1997 | Koster |
| 5,700,642 | A | 12/1997 | Monforte et al. |
| 5,702,895 | A | 12/1997 | Matsunaga et al. |
| 5,707,802 | A | 1/1998 | Sandhu et al. |
| 5,712,125 | A | 1/1998 | Uhlen |
| 5,716,825 | A | 2/1998 | Hancock et al. |
| 5,727,202 | A | 3/1998 | Kucala |

(Continued)

FOREIGN PATENT DOCUMENTS

| | | |
|---|---|---|
| CN | 101413034 A | 4/2009 |
| DE | 19732086 A1 | 1/1999 |

(Continued)

OTHER PUBLICATIONS

Shoaib et al. BMC Genomics (2008) 9: 415.*
Nakano et al. Journal of Biotechnology (2003) 102: 117-124.*
Product Data Sheet for TSF451-100 (2000), 2 pages.*
Weissensteiner et al. BioTechniques (1996) 21: 1102-1108.*
Hori et al. Biochemical and Biophysical Research Communications (2007) 352: 323-328.*
Spits et al. Nature Protocols (2006) 1(4): 1965-1970.*
Marcy et al., "Nanoliter Reactors Improve Multiple Displacement Amplification of Genomes from Single Cells," PLos Genetics, Sep. 2007, vol. 3, No. 9, e155, pp. 1702-1708.*
Hutchinson et al., "Cell-free cloning using phi29 DNA polymerase," PNAS, Nov. 29, 2005, vol. 102, No. 48, pp. 17332-17336.*

(Continued)

*Primary Examiner* — Young J Kim
(74) *Attorney, Agent, or Firm* — Casimir Jones, S.C.

(57) ABSTRACT

The present invention provides methods kits and systems for performing multiple displacement amplification reactions. In one method a sample of nucleic acid is provided. The nucleic acid is contacted with a reaction mixture which includes a set of oligonucleotide primers, a one or more polymerase enzymes and a detergent. The reaction mixture is then subjected to conditions under which the nucleic acid sequence is amplified to produce an amplified product in a multiple displacement reaction. The method may also be carried out by contacting the nucleic acid with the reaction mixture in the form of an emulsion. A kit is also provided for carrying out either the methods described above. The kit includes one or more polymerases, a plurality of primers and a detergent. The kit may also include a hydrophobic polymer and may include instructions for performing a multiple displacement amplification reaction on a nucleic acid sample.

16 Claims, 11 Drawing Sheets

(56) References Cited

U.S. PATENT DOCUMENTS

| | | | |
|---|---|---|---|
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,280,949 B1 * | 8/2001 | Lizardi ........................ 435/6.18 |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,323,009 B1 * | 11/2001 | Lasken et al. ............... 435/91.1 |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,783,939 B2 | 8/2004 | Olmsted et al. |
| 6,787,308 B2 | 9/2004 | Balasubramanian et al. |
| 6,800,289 B2 | 10/2004 | Nagata et al. |

(56) References Cited

U.S. PATENT DOCUMENTS

| | | |
|---|---|---|
| 6,813,615 B1 | 11/2004 | Colasanti et al. |
| 6,833,246 B2 | 12/2004 | Balasubramanian |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,115,400 B1 | 10/2006 | Adessi et al. |
| 7,198,893 B1 | 4/2007 | Köster et al. |
| 7,211,390 B2 | 5/2007 | Rothberg et al. |
| 7,211,414 B2 | 5/2007 | Hardin et al. |
| 7,217,510 B2 | 5/2007 | Ecker et al. |
| 7,220,549 B2 | 5/2007 | Buzby et al. |
| 7,226,739 B2 | 6/2007 | Ecker et al. |
| 7,232,656 B2 | 6/2007 | Balasubramanian et al. |
| 7,255,992 B2 | 8/2007 | Ecker et al. |
| 7,282,337 B1 | 10/2007 | Harris |
| 7,285,422 B1 | 10/2007 | Little et al. |
| 7,312,036 B2 | 12/2007 | Sampath et al. |
| 7,321,828 B2 | 1/2008 | Cowsert et al. |
| 7,329,492 B2 | 2/2008 | Hardin et al. |
| 7,339,051 B2 | 3/2008 | Crooke et al. |
| 7,349,808 B1 | 3/2008 | Kreiswirth et al. |
| 7,351,532 B2 | 4/2008 | Swerdlow et al. |
| 7,390,458 B2 | 6/2008 | Burow et al. |
| 7,419,787 B2 | 9/2008 | Köster |
| 7,482,120 B2 | 1/2009 | Buzby et al. |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minaminaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0248105 A1* | 12/2004 | Kumar ............................ 435/6 |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0123952 A1 | 6/2005 | Griffey et al. |
| 2005/0130196 A1 | 6/2005 | Hofstadler et al. |
| 2005/0130216 A1 | 6/2005 | Becker et al. |
| 2005/0142581 A1 | 6/2005 | Griffey et al. |
| 2005/0142584 A1 | 6/2005 | Willson et al. |
| 2005/0164215 A1 | 7/2005 | Hofstadler et al. |
| 2005/0239087 A1* | 10/2005 | Xiao et al. .................. 435/6 |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2005/0270191 A1 | 12/2005 | Hofstadler et al. |
| 2006/0014154 A1 | 1/2006 | Eshoo |
| 2006/0020391 A1 | 1/2006 | Kreiswirth et al. |
| 2006/0068390 A1* | 3/2006 | Tillett .................. C12Q 1/6844 435/6.14 |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0216737 A1* | 9/2006 | Bodeau et al. ................... 435/6 |
| 2006/0223071 A1 | 10/2006 | Wisniewski et al. |
| 2006/0240412 A1 | 10/2006 | Hall et al. |
| 2006/0259249 A1 | 11/2006 | Sampath et al. |
| 2006/0275749 A1 | 12/2006 | Sampath et al. |
| 2006/0275788 A1 | 12/2006 | Ecker et al. |

(56) References Cited

U.S. PATENT DOCUMENTS

| | | |
|---|---|---|
| 2007/0068573 A1 | 3/2007 | Cox et al. |
| 2007/0087336 A1 | 4/2007 | Sampath et al. |
| 2007/0087337 A1 | 4/2007 | Sampath et al. |
| 2007/0087338 A1 | 4/2007 | Sampath et al. |
| 2007/0087339 A1 | 4/2007 | Sampath et al. |
| 2007/0087340 A1 | 4/2007 | Sampath et al. |
| 2007/0087341 A1 | 4/2007 | Sampath et al. |
| 2007/0184434 A1 | 8/2007 | Sampath et al. |
| 2007/0218467 A1 | 9/2007 | Ecker et al. |
| 2007/0218489 A1 | 9/2007 | Sampath et al. |
| 2007/0224614 A1 | 9/2007 | Sampath et al. |
| 2007/0238116 A1 | 10/2007 | Sampath et al. |
| 2007/0243544 A1 | 10/2007 | Sampath et al. |
| 2007/0248969 A1 | 10/2007 | Sampath et al. |
| 2007/0264661 A1 | 11/2007 | Hofstadler et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0047665 A1 | 2/2009 | Hall et al. |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0035303 A1* | 2/2010 | Rhee ............................ 435/91.2 |
| 2010/0035323 A1* | 2/2010 | Ulmer .................... C12N 11/08 435/174 |
| 2010/0070194 A1 | 3/2010 | Ecker et al. |
| 2010/0145626 A1 | 6/2010 | Ecker et al. |
| 2010/0184035 A1 | 7/2010 | Hall et al. |
| 2010/0209916 A1 | 8/2010 | Zon |
| 2011/0065606 A1* | 3/2011 | Janulaitis ............. C12N 9/1276 506/11 |

FOREIGN PATENT DOCUMENTS

| | | |
|---|---|---|
| DE | 19802905 A1 | 7/1999 |
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| EP | 2256188 | 12/2010 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| WO | WO8803957 A1 | 6/1988 |
| WO | WO9015157 A1 | 12/1990 |
| WO | WO9205182 A1 | 4/1992 |
| WO | WO9208117 A1 | 5/1992 |
| WO | WO9209703 A1 | 6/1992 |
| WO | WO9219774 A1 | 11/1992 |
| WO | WO9303186 A1 | 2/1993 |
| WO | WO9305182 A1 | 3/1993 |
| WO | WO9308297 A1 | 4/1993 |
| WO | WO9416101 A2 | 7/1994 |
| WO | WO9419490 A1 | 9/1994 |
| WO | WO9421822 A1 | 9/1994 |
| WO | WO9504161 A1 | 2/1995 |
| WO | WO9511996 A1 | 5/1995 |
| WO | WO9513395 A1 | 5/1995 |
| WO | WO9513396 A2 | 5/1995 |
| WO | WO9531997 A1 | 11/1995 |
| WO | WO9606187 A1 | 2/1996 |
| WO | WO9616186 A1 | 5/1996 |
| WO | WO9629431 A2 | 9/1996 |
| WO | WO9632504 A2 | 10/1996 |
| WO | WO9635450 A1 | 11/1996 |
| WO | WO9637630 A1 | 11/1996 |
| WO | WO9733000 A1 | 9/1997 |
| WO | WO9734909 A1 | 9/1997 |
| WO | WO9737041 A2 | 10/1997 |
| WO | WO9747766 | 12/1997 |
| WO | WO9803684 A1 | 1/1998 |
| WO | WO9812355 A1 | 3/1998 |
| WO | WO9814616 A1 | 4/1998 |
| WO | WO9815652 A1 | 4/1998 |
| WO | WO9820020 A2 | 5/1998 |
| WO | WO9820157 A2 | 5/1998 |
| WO | WO9820166 A2 | 5/1998 |
| WO | WO9826095 A1 | 6/1998 |
| WO | WO9831830 A1 | 7/1998 |
| WO | WO9835057 A1 | 8/1998 |
| WO | 9839352 A1 | 9/1998 |
| WO | WO9840520 A1 | 9/1998 |
| WO | WO9854571 A1 | 12/1998 |
| WO | WO9854751 A1 | 12/1998 |
| WO | WO9905319 A2 | 2/1999 |
| WO | 9914226 A2 | 3/1999 |
| WO | WO9912040 A2 | 3/1999 |
| WO | WO9913104 A1 | 3/1999 |
| WO | WO9914375 A2 | 3/1999 |
| WO | WO9929898 A2 | 6/1999 |
| WO | WO9931278 A1 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A1 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0112853 A1 | 2/2001 |
| WO | WO0120018 A2 | 3/2001 |
| WO | WO0123604 A2 | 4/2001 |
| WO | WO0123608 A2 | 4/2001 |
| WO | WO0132930 A1 | 5/2001 |
| WO | WO0140497 A2 | 6/2001 |
| WO | WO0146404 A1 | 6/2001 |
| WO | WO0151661 A2 | 7/2001 |
| WO | WO0151662 A1 | 7/2001 |
| WO | WO0157263 A1 | 8/2001 |
| WO | WO0157518 A2 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |
| WO | WO02070664 A2 | 9/2002 |
| WO | WO02070728 A2 | 9/2002 |
| WO | WO02070737 A2 | 9/2002 |

(56) References Cited

FOREIGN PATENT DOCUMENTS

| | | |
|---|---|---|
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03018636 A2 | 3/2003 |
| WO | WO03020890 A2 | 3/2003 |
| WO | WO03033732 A2 | 4/2003 |
| WO | WO03054162 A2 | 7/2003 |
| WO | WO03054755 A2 | 7/2003 |
| WO | WO03060163 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | 2004009849 A1 | 1/2004 |
| WO | WO04003511 A2 | 1/2004 |
| WO | WO04009849 A1 | 1/2004 |
| WO | WO04011651 A1 | 2/2004 |
| WO | WO04013357 A2 | 2/2004 |
| WO | WO04040013 A1 | 5/2004 |
| WO | WO04044123 A2 | 5/2004 |
| WO | WO04044247 A2 | 5/2004 |
| WO | WO04052175 A2 | 6/2004 |
| WO | WO04053076 A2 | 6/2004 |
| WO | WO04053141 A2 | 6/2004 |
| WO | WO04053164 A1 | 6/2004 |
| WO | WO04060278 A2 | 7/2004 |
| WO | WO04070001 A2 | 8/2004 |
| WO | WO04072230 A2 | 8/2004 |
| WO | WO04072231 A2 | 8/2004 |
| WO | 04093644 A2 | 11/2004 |
| WO | WO04101809 A2 | 11/2004 |
| WO | 04111187 A2 | 12/2004 |
| WO | WO05003384 A1 | 1/2005 |
| WO | WO05009202 A2 | 2/2005 |
| WO | WO05012572 A1 | 2/2005 |
| WO | 2005023083 A2 | 3/2005 |
| WO | 2005023986 A2 | 3/2005 |
| WO | WO05024046 A2 | 3/2005 |
| WO | 2005033271 A2 | 4/2005 |
| WO | WO05036369 A2 | 4/2005 |
| WO | 2005044976 A2 | 5/2005 |
| WO | WO05054454 A1 | 6/2005 |
| WO | WO05075686 A1 | 8/2005 |
| WO | 05089128 A2 | 9/2005 |
| WO | WO05086634 A2 | 9/2005 |
| WO | 05092059 A2 | 10/2005 |
| WO | 05094421 A2 | 10/2005 |
| WO | WO05091971 A2 | 10/2005 |
| WO | WO05098047 A2 | 10/2005 |
| WO | 05117270 A2 | 12/2005 |
| WO | WO05116263 A2 | 12/2005 |
| WO | 06034294 A1 | 3/2006 |
| WO | 06071241 A2 | 7/2006 |
| WO | WO06089762 A1 | 8/2006 |
| WO | WO06094238 A2 | 9/2006 |
| WO | 06116127 A2 | 11/2006 |
| WO | 2006119066 A2 | 11/2006 |
| WO | WO06135400 A2 | 12/2006 |
| WO | WO2007014045 A2 | 2/2007 |
| WO | 2007047778 A2 | 4/2007 |
| WO | WO2007086904 A2 | 8/2007 |
| WO | 2007100397 A2 | 9/2007 |
| WO | 2007118222 A2 | 10/2007 |
| WO | WO2008104002 A2 | 8/2008 |
| WO | 2008/115427 | 9/2008 |
| WO | 2008116182 A1 | 9/2008 |
| WO | WO2008118809 A1 | 10/2008 |
| WO | 2008143627 A2 | 11/2008 |
| WO | 2008151023 A2 | 12/2008 |
| WO | 2008127839 A3 | 2/2009 |
| WO | 2009023358 A2 | 2/2009 |
| WO | 2009/107816 | 9/2009 |
| WO | 2009017902 A3 | 10/2009 |
| WO | 2009038840 A3 | 10/2009 |
| WO | 2010148039 A2 | 12/2010 |

OTHER PUBLICATIONS

Batzer M.A., et al., "Enhanced Evolutionary PCR using Oligonucleotides with Inosine at the 3'-terminus," Nucleic Acids Research, 1991, vol. 19 (18), pp. 5081.

Ecker Supporting Information [online], May 23, 2005 [retrieved on Jul. 31, 2011]. Retrieved from the Internet< URL: http://www.pnas.org/content/102/22/8012/suppl/DC1>.

Gilar M., et al., "Study of Phosphorothioate-Modified Oligonucleotide Resistance to 3'-exonuclease using Capillary Electrophoresis," Journal of Chromatography B: Biomedical Sciences and Applications, 1998, vol. 714 (1), pp. 13-20.

Hughes S., et al., "Use of Whole Genome Amplification and Comparative Genomic Hybridisation to Detect Chromosomal Copy Number Alterations in Cell Line Material and Tumour Tissue," Cytogenetic and Genome Research, 2004, vol. 105 (1), pp. 18-24.

Latorra D., et al., "Design Considerations and Effects of LNA in PCR Primers," Molecular and Cellular Probes, 2003, vol. 17 (5), pp. 253-259.

Non-Final Office Action dated Feb. 22, 2012 for U.S. Appl. No. 12/602,641, filed Jun. 7, 2010.

Resuehr D., et al., "A Real-Time Polymerase Chain Reaction-Based Evaluation of cDNA Synthesis Priming Methods," Analytical Biochemistry, 2003, vol. 322 (2), pp. 287-291.

Aaserud D.J., et al., "Accurate Base Composition of Double-Strand DNA by Mass Spectrometry," American Society for Mass Spectrometry, 1996, vol. 7 (12), pp. 1266-1269.

Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.

Adam E., et al., "Characterization of Intertype Specific Epitopes on Adenovirus Hexons," Archives of Virology, 1998, vol. 143 (9), pp. 1669-1682.

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucleotides for the Detection of Infectious Bronchitis Virus by Thepolymerase Chain Reaction," Avian Pathology, 1996, vol. 25 (4), pp. 817-836.

Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.

Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

(56) References Cited

OTHER PUBLICATIONS

Alba M.M., et al., "VIDA: A Virus Database System for the Organization of Animal Virus Genome Open Reading Frames," Nucleic Acids Research, 2001, vol. 29 (1), pp. 133-136.

Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.

Allawi H.T., et al., "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Names B.D., ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in *Staphylococci*," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnositic Microbiology and Infectious Diseases, 2001, vol. 40 (1-2), pp. 5-10.

Archer G.L., et al., "Detection of Methicillin Resistance in *Staphylococci* by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.

Aronsson F., et al., "Persistence of the Influenza A/WSN/33 Virus RNA at Midbrain Levels of Immunodefective Mice," Journal of Neurovirology, 2001, vol. 7 (2), pp. 117-124.

Ausubel F.M., et al., Eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing *Mycobacteria* Species," Molecular and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of *Mycobacterium* Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable *Borrelia* Species in the Hard Tick *Amblyomma americanum*: Possible Agent of a Lyme Disease-Like Illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.

Barr I.G., et al., "An Influenza A(H3) Reassortant was Epidemic in Australia and New Zealand in 2003," Journal of Medical Virology, 2005, vol. 76 (3), pp. 391-397.

Barski P., et al., "Rapid Assay for Detection of Methicillin-Resistant *Staphylococcus aureus* Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A *Streptococci*," Journal of Clincal Microbiology, 1996, vol. 34 (4), pp. 953-958.

Beall B., et al., "Survey of emm Gene Sequences and T-Antigen Types from Systemic *Streptococcus* pyogenes Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae," Virus taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.

(56) References Cited

OTHER PUBLICATIONS

Berencsi G., et al., "Molecular Biological Characterization of Adenovirus DNA," Acta Microbiologica et Immunologica Hungarica, 1998, vol. 45 (3-4), pp. 297-304.
Bishop M.J., et al., "Molecular Sequence Databases" in: Nucleic Acid and Protein Sequence Analysis, 4th Chapter, Bishop M.J., et al., Eds, IRL Press, 1987, pp. 83-113.
Bisno A.L., "*Streptococcus* Pyogenes" in: Infectious Diseases and Their Etiologic Agents, vol. 2, Mandell, Eds., Churchill Livingston, New York, pp. 1786-1799.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Blaiotta G., et al., "PCR Detection of Staphylococcal Enterotoxin Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.
BLAST Search results, Mar. 7, 2006.
Boivin-Jahns V., et al., "Bacterial Diversity in a Deep-Subsurface Clay Environment," Applied and Environmental Microbiology, 1996, vol. 62 (9), pp. 3405-3412.
Bolton E.T., et al., "A General Method for the Isolation of RNA Complementary to DNA," Proceedings of the National Academy of Sciences, 1962, vol. 48, pp. 1390-1397.
Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Boubaker K., et al., "Panton-Valentine Leukocidin and Staphylococcal Skin Infections in Schoolchildren," Emerging Infectious Diseases, 2004, vol. 10 (1), pp. 121-124.
Bowen J.E., et al., "The Native Virulence Plasmid Combination Affects the Segregational Stability of a Thetareplicating Shuttle Vector in Bacillus Anthracis Var," Journal of Applied Microbiology, 1999, vol. 87 (2), pp. 270-278.
Bowers K.M., et al., "Screening for Methicillin Resistance in *Staphylococars aureus* and Coagulasenegative *Staphylococci*: Evaluation of Three Selective and Mastalex-MRSA latex Agglutination," British Journal of Biomedical Science, 2003, vol. 60 (2), pp. 71-74.
Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the *Arabidopsis* Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the *Staphylococcal* mecA Gene from Bactec BloodCulture Bottles by the Polymerase Chain Reaction," American Journal of Clincal Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction dated Jan. 6, 2009 for U.S. Appl. No. 10/660,996, filed Sep. 12, 2003.
Certificate of Correction dated Aug. 7, 2007 for U.S. Appl. No. 10/660,997, filed Sep. 12, 2003.
Certificate of Correction dated Dec. 12, 2006 for U.S. Appl. No. 10/156,608, filed May 24, 2002.
Certificate of Correction dated Jul. 17, 2007 for U.S. Appl. No. 09/891,793, filed Jun. 26, 2001.
Certificate of Correction dated Mar. 31, 2008 for U.S. Appl. No. 09/891,793, filed Jun. 26, 2001.
Certificate of Correction dated Mar. 31, 2008 for U.S. Appl. No. 10/156,608, filed May 24, 2002.
Certificate of Correction dated Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.

(56) References Cited

OTHER PUBLICATIONS

Chamberlin M., et al., "New RNA Polymerase from *Escerichia coli* Infected with Bacteriophage T7," Nature, 1970, vol. 228 (5268), pp. 227-231.

Chandra S., et al., "Virus Reduction in the Preparation and Intravenous Globulin: In Vitro Experiments," Transfusion, 1999, vol. 39 (3), pp. 249-257.

Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.

Chaves F., et al., "Molecular Characterization of Resistance to Mupirocin in Methicillin-Susceptible and -Resistant Isolates of *Staphylococcus aureus* from Nasal Samples," Journal of Clincal Microbiology, 2004, vol. 42 (2), pp. 822-824.

Chelly J., et al., "Transcription of the Dystrophin Gene in Human Muscle and Non-Muscle Tissue," Nature, 1988, vol. 333 (6176), pp. 858-860.

Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.

Chen C.H., et al., Laser Desorption Mass Spectrometry for FastDNA Sequencing [online], Nov. 1994, Retrieved from the Internet< URL:http://www.ornl.gove/sci/techresources/Human_Genome/publicat/94SANTA/sequencing/seqtoc.shtml>.

Chen J., et al., "A Universal PCR Primer to Detect Members of the Potyviridae and its Use to Examine the Taxonomic Status of Several Members of the Family," Archives of Virology, 2001, vol. 146 (4), pp. 757-766.

Chen N., et al., "The Genomic Sequence of Ectromelia Virus, the Causative Agent of Mousepox," Virology, 2003, vol. 317 (1), pp. 165-186.

Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.

Chen Y.Z., et al., "A BAC-Based STS-Content Map Spanning a 35-Mb Region of Human Chromosome 1p35-36," Genomics, 2001, vol. 74 (1), pp. 55-70.

Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.

Chiu N.H., et al., "Mass Spectrometry of Single-Stranded Restriction Fragments Captured by an Undigested Complementary Sequence," Nucleic Acids Research, 2000, vol. 28 (8), pp. E31.

Chmielewicz B., et al., "Development of a PCR-Based Assay for Detection, Quantification, and Genotyping of Human Adenoviruses," Clinical Chemistry, 2005, vol. 51 (8), pp. 1365-1373.

Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.

Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.

Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.

Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.

Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.

Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.

Collins D.W., et al., "Numerical Classification of Coding Sequences," Nucleic Acids Research, 1992, vol. 20 (6), pp. 1405-1410.

Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.

Contreras-Salazar B., et al., "Up Regulation of the Epstein-Barr Virus (EBV)-Encoded Membrane Protein Lmp in the Burkitt's Lymphoma Line Daudi after Exposure to N-Butyrate and after EBV Superinfection," Journal of Virology, 1990, vol. 64 (11), pp. 5441-5447.

Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.

Cornel A.J., et al., "Polymerase Chain Reaction Species Diagnostic Assay for Anopheles Quadrimaculatus Cryptic Species (*Diptera:Culicidae*) Based on Ribosomal DNA ITS2 Sequences," Journal of Medical Entomology, 1996, vol. 33 (1), pp. 109-116.

Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.

Crain P.F., et al., "Applications of Mass Spectrometry to the Characterization of Oligonucleotides and Nucleic Acids," Current Opinion in Biotechnology, 1998, vol. 9 (1), pp. 25-34.

(56) References Cited

OTHER PUBLICATIONS

Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Deforce D.L., et al., "Analysis of Oligonucleotides by ESI-MS," Advances in Chromatography, 2000, vol. 40, pp. 539-566.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.
Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus Aureus* tst Gene among Community- and Hospital-Acquired Strains and Isolates from Wegener's Granulomatosis Patients," FEMS Microbiology Letters, 2005, vol. 245 (1), pp. 185-189.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.
Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Severe Acute Respiratory Syndrome," New England Journal of Medicine, 2003, vol. 348 (20), pp. 1967-1976.
Dubernets S., et al., "A PCR-Based Method for Identification of *Lactobacilli* at to Genus Level," FEMS Microbiology Letters, 2002, vol. 214 (2), pp. 271-275.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Edwards K.M., et al., "Adenovirus Infections in Young Children," Pediatrics, 1985, vol. 76 (3), pp. 420-424.
Ellis J.S. et al., "Molecular Diagnosis of Influenza," Reviews in Medical Virology, 2002, vol. 12 (6), pp. 375-389.

(56) References Cited

OTHER PUBLICATIONS

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Elnifro E.M., et al., "PCR and Restriction Endonuclease Analysis for Rapid Identification of Adenovirus Subgenera," Journal of Clinical Microbiology, 2000, vol. 38 (6), pp. 2055-2061.

Elsayed S., et al., "Development and Validation of a Molecular Beacon Probe-Based Real-Time Polymerase Chain Reaction Assay for Rapid Detection of Methicillin Resistance in *Staphylococcus aureus*," Archives of Pathology and Laboratory Medicine, 2003, vol. 127 (7), pp. 845-849.

EMBL "*Arabidopsis thaliana* T-DNA Flanking Sequence, Left Border, Clone 346C06," Accession No. AJ552897, Mar. 2003.

EMBL "Dog (Clone: CXX.147) Primer for STS 147, 3" End, Sequence Tagged Site," Accession No. L15697, Mar. 4, 2000.

EMBL "Human, muscle, Mitochondrial Mutant, 22 nt, segment 2 of 2," Accession No. S90302, Sep. 1, 2004.

EMBL "Sequence 10 from Patent U.S. Pat. No. 6563025," Accession No. AR321656, Aug. 18, 2003.

EMBL "Synthetic Construct DNA, Reverse Primer for Human STS sts-AA031654 at 1p36" Accession No. AB068711, May 21, 2003.

Enright M.C., et al., "A Multilocus Sequence Typing Scheme for *Streptococcus pneumoniae*: Identification of Clones Associated with Serious Invasive Disease," Microbiology, 1998, vol. 144 (Pt 11), pp. 3049-3060.

Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.

Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus* (MRSA)," Proceedings of the National Academy of Sciences, 2002, vol. 99 (11), pp. 7687-7692.

Enright M.C., "The Evolution of a Resistant Pathogen—the Case of MRSA," Current Opinion in Pharmacology, 2003, vol. 3 (5), pp. 474-479.

Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.

Erlich H.A., Ed., PCR Technology: Principles and Applications for DNA Amplification, W.H. Freeman and Company, 1989.

Esmans E.L., et al., "Liquid Chromatography-Mass Spectrometry in Nucleoside, Nucleotide and Modified Nucleotide Characterization," Journal of Chromatography, 1998, vol. 794, pp. 109-127.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

European Search Report for Application No. EP10175659.1, dated Feb. 9, 2011, 4 pages.

Evans P., et al., "Practical Algorithms for Universal DNA Primer Design: An Exercise in Algorithm Engineering," Currents in Computational Molecular Biology, 2001, pp. 25-26.

Ex Parte Re-Examination Certificate for U.S. Appl. No. 90/010,209, dated Jul. 7, 2009.

Ex Parte Re-Examination Certificate for U.S. Appl. No. 90/010,210, dated Dec. 28, 2010.

Ex Parte Re-Examination Certificate for U.S. Appl. No. 90/010,447 dated Feb. 15, 2011.

Examiner Interview Summary dated Oct. 3, 2005 for U.S. Appl. No. 10/326,046, filed Dec. 18, 2002.

Examiner Interview Summary dated Nov. 6, 2008 for U.S. Appl. No. 10/728,486, filed Dec. 5, 2003.

Examiner Interview Summary dated Jun. 7, 2011 for U.S. Appl. No. 11/930,108, filed Oct. 31, 2007.

Examiner Interview Summary dated Aug. 10, 2004 for U.S. Appl. No. 09/798,007, filed Mar. 2, 2001.

Examiner Interview Summary dated Aug. 10, 2004 for U.S. Appl. No. 09/891,793, filed Jun. 26, 2001.

Examiner Interview Summary dated Aug. 10, 2004 for U.S. Appl. No. 10/156,608, filed May 24, 2002.

Examiner Interview Summary dated Aug. 10, 2004 for U.S. Appl. No. 10/326,642, filed Dec. 18, 2002.

Examiner Interview Summary dated May 19, 2003 for U.S. Appl. No. 09/891,793, filed Jun. 26, 2001.

Examiner Interview Summary dated Oct. 24, 2008 for U.S. Appl. No. 11/582,859, filed Oct. 17, 2006.

Examiner Interview Summary dated Feb. 27, 2006 for U.S. Appl. No. 10/326,644, filed Dec. 18, 2002.

Examiner Interview Summary dated Jan. 27, 2006 for U.S. Appl. No. 10/323,211, filed Dec. 18, 2002.

Examiner Interview Summary dated May 28, 2008 for U.S. Appl. No. 10/660,998, filed Sep. 12, 2003.

Examiner Interview Summary dated Oct. 28, 2008 for U.S. Appl. No. 11/331,987, filed Jan. 13, 2006.

Examiner Interview Summary dated Oct. 29, 2008 for U.S. Appl. No. 11/331,978, filed Jan. 13, 2006.

Examiner Interview Summary dated Oct. 29, 2009 for U.S. Appl. No. 10/660,122, filed Sep. 11, 2003.

Examiner Interview Summary dated Jul. 31, 2006 for U.S. Appl. No. 10/326,643, filed Dec. 18, 2002.

Extended European Search Opinion for Application No. EP10175659.1, dated Feb. 21, 2011, 5 pages.

Extended European Search Report for Application No. EP10179789.2, dated Mar. 22, 2011, 9 pages.

Extended European Search Report for Application No. EP10179791.8, dated Mar. 17, 2011, 7 pages.

Extended European Search Report for Application No. EP10179795.9, dated Mar. 22, 2011, 9 pages.

Facklam R., et al., "Emm Typing and Validation of Provisional M Types for Group A *Streptococci*," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "Francisella Tularensis Strain Typing Using Multiple-Locus, Variable-No. Tandem Repeat Analysis," Journal of Critical Microbiology, 2001, vol. 39 (9), pp. 3186-3192.

Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.

Final Office Action dated Aug. 6, 2010 for U.S. Appl. No. 11/929,910, filed Oct. 30, 2007.

Final Office Action dated Jul. 8, 2010 for U.S. Appl. No. 12/326,800, filed Dec. 2, 2008.

Final Office Action dated May 12, 2010 for U.S. Appl. No. 11/674,538, filed Feb. 13, 2007.

Final Office Action dated Apr. 14, 2011 for U.S. Appl. No. 12/049,949, filed Mar. 17, 2008.

(56) References Cited

OTHER PUBLICATIONS

Final Office Action dated Jun. 14, 2011 for U.S. Appl. No. 12/616,422, filed Nov. 11, 2009.
Final Office Action dated Oct. 14, 2009 for U.S. Appl. No. 10/943,344, filed Sep. 17, 2004.
Final Office Action dated Nov. 17, 2009 for U.S. Appl. No. 11/582,875, filed Oct. 17, 2006.
Final Office Action dated Feb. 18, 2010 for U.S. Appl. No. 10/754,415, filed Jan. 9, 2004.
Final Office Action datd Nov. 20, 2009 for U.S. Appl. No. 11/331,987, filed Jan. 13, 2006.
Final Office Action dated Jun. 23, 2010 for U.S. Appl. No. 11/930,017, filed Oct. 30, 2007.
Final Office Action dated Feb. 26, 2009 for U.S. Appl. No. 11/582,863, filed Oct. 17, 2006.
Final Office Action dated Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin-Resistant*Staphylococcus Aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the Erdec Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of *Brucell canis* from Other *Brucella* Spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of Mycoplasma Genitalium," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in *Staphylococcus aureus* Clinicallsolates and in Vitro Selection of Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gall J.G., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp. 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.
Genbank, "{Deletion 6} [Human, Muscle, Mitochondrial Mutant, 22 nt, Segment 2 of 2]," Accession No. S90302.1, Jun. 10, 1992.
Genbank, "Acinetobacter Genomosp. 10 Strain Cip 70.12 RNA Polymerase Subunit B (rpoB) Gene, Complete Cds," Accession No. 78099429, Mar. 11, 2006.
Genbank, "Bovine Parainfluenza Virus 3 Strain Shipping Fever, Complete Genome," Accesion No. AF178655, Sep. 19, 2000.
Genbank, "Clostridium Tetani E88, Complete Genome," Accession No. AE015927.1, Feb. 4, 2003.
Genbank, "*E. coli* Operon rpoBC Coding for the Beta- and Beta"-Subunits of RNA Polymerase (Genes rpoC and rpoB), and Genes rplL, rlpJ, rplA, and rplK Coding for 50S Ribosomal Subunit Proteins L7/L12, L10, L1, and L11, Respectively. (Map position 89-90 min.), Accession No. 42813, Feb. 28, 1992.
Genbank, "*E.coli* 16S Ribosomal RNA," Accession No. 174375, Aug. 11, 1995.
Genbank, "*E.coli* Open Reading Frame Upstream of Leu Operon," Accession No. M21150, Sep. 15, 1990.
Genbank, "*E. coli* rRNA Operon (rrnB) Coding for Glu-tRNA-2, 5S, 16S and 23S rRNA," Accession No. 147581, Sep. 14, 1992.
Genbank, "Enterococcus Malodoratus Strain ATCC43197 Elongation Factor Tu (tufA) Gene, Partial Cds," Accession No. AF274728, Dec. 11, 2000.
Genbank "*Escherichia coli* str. K-12 substr. MG1655, Complete Genome," Accession No. NC000913, Oct. 15, 2001.
Genbank, "*Homo sapiens* Haplotype V Mitochondrion, Complete Genome", Accession No. AF381990.1, Dec. 28, 2001.
Genbank, "Human Adenovirus Type 4 Hexon Gene," for Accession No. X84646, Jun. 30, 1995.
Genbank, "Human Coronavirus 229E, Complete Genome," Accession No. AF304460, Jul. 11, 2001.
Genbank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5-similar to SW:COX3 Human P00414

(56) References Cited

OTHER PUBLICATIONS

Cytochrome C Oxidase Polypeptide III ;, mRNA sequence", Accession No. BQ581956.1, Jun. 20, 2002.
Genbank, "Influenza B Virus B/Panama/45/90 Polymerase (PB2) mRNA, Complete Cds", Accession No. AF005737, Oct. 4, 1997, pp. 1-3.
Genbank, "Mastadenovirus h7 Hexon Gene," Accession No. Z48571, Apr. 18, 2005.
GenBank, "or72a01.s1 NCI_CGAP_Lu5 Homo sapiens cDNA Clone Image:1601352 3-similar to SW:COX1_Human P00395 Cytochrome C Oxidase Polypeptide I ;, mRNA sequence", Accession No. A1002209.1, Jun. 10, 1998.
Genbank "*Staphylococcus aureus* RN4220 ErmC Gene, Partial Cds," Accession No. 18542231, Sep. 16, 2003.
Genbank "*Staphylococcus aureus* Strain MSSA476, Complete Genome," Accession No. BX571857.1, Jun. 24, 2004.
Genbank, "*Staphylococcus aureus* Subsp. *Aureus* Mu50, Complete Genome," Accession No. 15922990, Oct. 4, 2001.
Genbank "*Staphylococcus aureus* Subsp. *Aureus* MW2, Complete Genome," Accession No. GI21281729, May 31, 2002.
Genbank, "*Staphylococcus epidermidis* ATCC 12228, Complete Genome," Accession No. AE015929.1, Jan. 2, 2003.
Genbank "*Streptococcus agalactiae* 2603V/R, Complete Genome," Accession No. AE009948.1, Aug. 28, 2002.
Genbank, "*Streptococcus anginosus* Elongation Factor Tu (tuf) Gene, Partial cds," Accession No. AF276257.1, Jul. 1, 2001.
Genbank, "*Streptococcus pneumoniae* Isolate 95.11nOOS DNA Gyrase Subunit B (gyrB) Gene, Complete Cds," Accession No. 73916349, Sep. 30, 2005.
Genbank, "*Streptococcus pyogenes* Strain MGAS8232, Complete Genome," Accession No. AE009949.1, Apr. 3, 2002.
Genbank, "Venezuelan Equine Encephalitis Virus Nonstructural Polyprotein and Structural Polyprotein Genes, Complete Cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.
Giles R.E., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.
Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.
Ginther C., et al., "Identifying Individuals by Sequencing Mitochondrial DNA from Teeth," Nature Genetics, 1992, vol. 2 (2), pp. 135-138.
Gjoen K.V., et al., "Specific Detection of Coxsackie Viruses A By the Polymerase Chain Reaction," Clinical and Diagnostic Virology, 1997, vol. 8 (3), pp. 183-188.
Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.
Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.
Gravet A., et al., "Characterization of a Novel Structural Member, LukE-LukD, of the Bi-Component Staphylococcal Leucotoxins Family," Febs Letters, 1998, vol. 436 (2), pp. 202-208.
Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.
Greenberg B.D., et al., "Intraspecific Nucleotide Sequence Variability Surrounding the Origin of Replicationin Human Mitochondrial DNA," Gene, 1983, vol. 21, pp. 33-49.
Griffey, et al., "Detection of Base Pair Mismatches in Duplex DNA and RNA Oligonucleotides Using Electrospray Mass Spectrometry," SPIE, 1997, vol. 2985, pp. 82-86.
Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.
Griffin T.J., et al., "Single-Nucleotide Polymorphism Analysis by Maldi-TOF Mass Spectrometry," Trends in Biotechnology, 2000, vol. 18 (2), pp. 77-84.
Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.
Grundmann H., et al., "Emergence and Resurgence of Meticillin-Resistant *Staphylococcus aureus* as a Public-Health Threat," Lancet, 2006, vol. 368 (9538), pp. 874-885.
Grzybowski T., et al., "Extremely High Levels of Human Mitochondrial DNA Heteroplasmy in Single Hair Roots," Electrophoresis, 2000, vol. 21 (3), pp. 548-553.
Gu Z., et al., "Multiplexed, Real-Time PCR for Quantitative Detection of Human Adenovirus," Journal of Clinical Microbiology, 2003, vol. 41 (10), pp. 4636-4641.
Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.
Haff L.A., et al., "Multiplex Genotyping of PCR Products with Mass Tag-Labeled Primers," Nucleic Acids Research, 1997, vol. 25 (18), pp. 3749-3750.
Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.
Haines J.D., et al., "Medical Response to Bioterrorism: Are We Prepared," Journal of Oklahoma State Medical Association, 2000, vol. 93, pp. 187-196.
Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.
Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.
Hamel S., et al., "Consensus PCR and Microarray for Diagnosis of the Genus *Staphylococcus*, Species, and Methicillin Resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.
Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

(56) References Cited

OTHER PUBLICATIONS

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.
Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "Sccmecin Staphylococci: Genes on the Move," FEMS Immuol Medical Microbiol, 2006, vol. 46, pp. 8-20.
Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.
Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.
Haugland R.A., et al., "Identification of Putative Sequence Specific PCR Primers for Detection of the Toxygenic Fungal Species Stachybotrys Chartarum," Molecular and Cellular Probes, 1998, vol. 12 (6), pp. 387-396.
Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
Heim A., et al., "Rapid and Quantitative Detection of Human Adenovirus DNA by Real-Time PCR," Journal of Medical Virology, 2003, vol. 70, pp. 228-239.
Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.
Herrmann B., et al., "Differentiation of *Chlamydia* spp. by Sequence Determination and Restriction Endonuclease Cleavage of RNase P RNA Genes," Journal of Clinical Microbiology, 1996, vol. 34 (8), pp. 1897-1902.
Higgins G.S., et al., "Competitive Oligonucleotide Single-base Extension Combined with Mass Spectrometric Detection for Mutation Screening," Biotechniques, 1997, vol. 23 (4), pp. 710-714.
Higgins J.A., et al., "Sensitive and Rapid Identification of Biological Threat Agents," Annals of the New York Academy of Sciences, 1999, vol. 894, pp. 130-148.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hiramatsu K., et al., "The Emergence and Evolution of Methicillin-Resistant *Staphylococcusaureus*," Trends Microbiology, 2001, vol. 9 (10), pp. 486-493.
Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.
Hoffman E., et al., "Rescue of Influenza B Virus from Eight Plasmids," Proceedings of the National Academy of Sciences, 2002, vol. 99 (17), pp. 11411-11416.
Hoffmann E., et al., "Universal Primer Set for the Full-Length Amplification of all Influenza A Viruses," Archives of Virology, 2001, vol. 146 (12), pp. 2275-2289.
Hofstadler S.A., et al., "TIGER: The Universal Biosensor," International Journal of Mass Spectrometry, 2005, vol. 242, pp. 23-41.
Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis—Validation and Use for Forensic Casework," Forensic Science Review, 1999, vol. 11 (1), pp. 22-50.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Honda K., et al., "Universal Method of Hypersensitive Nested PCR Toward Forensic DNA typing," International Congress Series, 1998, vol. 7, pp. 28-30.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.
Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time Pcr Assay for Rapid Detection of Methicillin-Resistantstaphylococcus Aureus Directly from Specimens Containing a Mixture of Staphylococci," Journal of Clinical Microbiology, 2004, vol. 42 (5), pp. 1875-1884.
Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.
Hurdle J.G., et al., "Analysis of Mupirocin Resistance and Fitness in *Staphylococus aureus* by Molecular Genetic and Structural Modeling Techniques," Antimicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

(56) References Cited

OTHER PUBLICATIONS

Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, dated Jun. 11, 2003, 6 pages.
International Preliminary Examination Report for Application No. PCT/US2002/20336, dated Apr. 26, 2004, 8 pages.
International Preliminary Examination Report for Application No. PCT/US2003/09802, dated Apr. 8, 2005, 7 pages.
International Preliminary Examination Report for Application No. PCT/US2003/22835, dated Mar. 5, 2005, 4 pages.
International Preliminary Examination Report for Application No. PCT/US2003/38505, dated Mar. 3, 2006, 5 pages.
International Preliminary Examination Report for Application No. PCT/US2003/38757, dated Feb. 2, 2007, 5 pages.
International Preliminary Examination Report for Application No. PCT/US2003/38761, dated Jun. 27, 2006, 6 pages.
"International Preliminary Report on Patentability and Written Opinion for Application No. PCT/US04/007236, dated Mar. 16, 2006, 7 pages.".
International Preliminary Report on Patentability and Written Opinion for Application No. PCT/US2005/00386, dated Jul. 10, 2006, 6 pages.
International Preliminary Report on Patentability and Written Opinion for Application No. PCT/US2005/030058, dated Sep. 25, 2007, 6 pages.
International Preliminary Report on Patentability and Written Opinion for Application No. PCT/US2005/033707, dated Mar. 20, 2007, 6 pages.
International Preliminary Report on Patentability for Application No. PCT/US2004/033742, dated Jun. 20, 2006, 1 page.
International Preliminary Report on Patentability for Application No. PCT/US2005/018031, dated Nov. 29, 2006, 1 page.
International Preliminary Report on Patentability for Application No. PCT/US2006/028397, dated Jan. 22, 2008, 1 page.
International Preliminary Report on Patentability for Application No. PCT/US2008/054926, dated Aug. 26, 2009, 1 page.
International Preliminary Report on Patentability for Application No. PCT/US2008/065332, dated Dec. 1, 2009, 1 page.
International Preliminary Report on Patentability, Written Opinion and International Search Report for Application No. PCT/US2004/015123, dated Oct. 3, 2005, 8 pages.
International Search Report and Written Opinion for Application No. PCT/US2005/018031, dated Jun. 28, 2006, 14 pages.
International Search Report and Written Opinion for Application No. PCT/US2006/007747, dated Sep. 5, 2006, 13 pages.
International Search Report and Written Opinion for Application No. PCT/US2006/028397, dated Mar. 5, 2007, 14 pages.
International Search Report and Written Opinion for Application No. PCT/US2006/040747, dated Mar. 17, 2009, 19 pages.
International Search Report and Written Opinion for Application No. PCT/US2006/061307, dated Jan. 9, 2008, 21 pages.
International Search Report and Written Opinion for Application No. PCT/US2007/020045 dated Jan. 8, 2009, 17 pages.
International Search Report and Written Opinion for Application No. PCT/US2008/054926, dated Jan. 26, 2009, 15 pages.
International Search Report and Written Opinion for Application No. PCT/US2008/057901, dated Aug. 28, 2008, 14 pages.
International Search Report and Written Opinion for Application No. PCT/US2008/064891, dated Jun. 29, 2009, 15 pages.
International Search Report and Written Opinion for Application No. PCT/US2010/052904, dated Feb. 4, 2011, 8 pages.
International Search Report for Application No. PCT/US04/007236, dated Feb. 24, 2006, 2 pages.
International Search Report for Application No. PCT/US2002/06763, dated Oct. 23, 2002, 2 pages.
International Search Report for Application No. PCT/US2002/20336, dated Feb. 3, 2003, 4 pages.
International Search Report for Application No. PCT/US2003/009802, dated Aug. 3, 2004, 2 pages.
International Search Report for Application No. PCT/US2003/038505, dated Apr. 12, 2005, 2 pages.
International Search Report for Application No. PCT/US2003/038830, dated Aug. 25, 2004, 4 pages.
International Search Report for Application No. PCT/US2003/22835, dated Dec. 12, 2003, 1 page.
International Search Report for Application No. PCT/US2003/38757, dated Jun. 24, 2004, 2 pages.
International Search Report for Application No. PCT/US2003/38761, dated Dec. 30, 2005, 5 pages.
International Search Report for Application No. PCT/US2003/38795, dated Apr. 19, 2004, 3 pages.
International Search Report for Application No. PCT/US2004/012671, dated Sep. 28, 2007, 2 pages.
International Search Report for Application No. PCT/US2004/015123, dated Oct. 3, 2005, 2 pages.
International Search Report for Application No. PCT/US2004/015196, dated Jul. 1, 2005, 3 pages.
International Search Report for Application No. PCT/US2004/028869, dated Jul. 17, 2006, 4 pages.
International Search Report for Application No. PCT/US2004/033742, dated May 15, 2006, 2 pages.
International Search Report for Application No. PCT/US2005/000386, dated May 9, 2006, 3 pages.
International Search Report for Application No. PCT/US2005/005356, dated Aug. 7, 2007, 4 pages.
International Search Report for Application No. PCT/US2005/006133, dated Jul. 26, 2007, 4 pages.
International Search Report for Application No. PCT/US2005/009557, dated Sep. 19, 2005, 1 page.
International Search Report for Application No. PCT/US2005/018337, dated Oct. 10, 2006, 2 pages.
International Search Report for Application No. PCT/US2005/024799, dated Dec. 28, 2006, 4 pages.
International Search Report for Application No. PCT/US2005/030058, dated Aug. 20, 2007, 1 page.
International Search Report for Application No. PCT/US2005/033707, dated Feb. 6, 2006, 3 pages.
International Search Report for Application No. PCT/US2007/066194, dated Jan. 15, 2008, 4 pages.
International Search Report for Application No. PCT/US2008/065332, dated Nov. 28, 2008, 4 pages.
International Search Report for Application No. PCT/US2009/045635, dated Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of *Cyanobacteria*," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.

(56) References Cited

OTHER PUBLICATIONS

Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for TSST-1 in Staphylococcal Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of *Francisella* species and Subspecies and Development of a Specific PCR that Distinguishes the Two Major Subspecies of *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of *B. subtilis* and *B. atrophaeus*, Closely Related Species of Bacilli," Journal of Microbiological Methods, 2000, vol. 40 (3), pp. 241-254.
Jonas D., et al., "Rapid PCR-Based Identification of Methicillin-Resistant *Staphylococcus aureus* from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-HBC Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.

Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal *Eubacterium* Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431-Mediated mecI Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.
Ke D., et al., "Development of a PCR Assay for Rapid Detection of Enterococci," Journal of Clinical Microbiology, 1999, vol. 37 (11), pp. 3497-3503.
Kearns A.M., et al., "Rapid Detection of Methicillin-Resistant *Staphylococci* by Multiplex PCR," The Journal of Hospital Inspection, 1999, vol. 43 (1), pp. 33-37.
Keller A., et al., "Empirical Statistical Model to Estimate the Accuracy of Peptide Identifications Made by MS/MS and Database Search," Analytical Chemistry, 2002, vol. 74 (20), pp. 5383-5392.
Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.
Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.
Kidd A.H., et al., "Rapid Subgenus Identification of Human Adenovirus Isolates by a General PCR," Journal of Clinical Microbiology, 1996, vol. 34 (3), pp. 622-627.
Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.
Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.
Kilbourne E.D., "Influenza Pandemics of the 20th Century," Emerging Infectious Diseases Journal, 2006, vol. 12 (1), pp. 9-14.
Kilbourne E.D., "Influenza Pandemics: Can We Prepare for the Unpredictable," Viral Immunology, 2004, vol. 17 (3), pp. 350-357.
Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.
Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.
Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.
Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.
Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

(56) References Cited

OTHER PUBLICATIONS

Kolbert C.P., et al., "Branched-DNA Assay for Detection of the mecA Gene in Oxacillin-Resistant and Oxacillin-Sensitive *Staphylococci*," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus*isolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin CausesNecrotizing Pneumonia," ScienceExpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, vol. 1263, pp. 610-614.

(56) References Cited

OTHER PUBLICATIONS

Li Q.G., et al., "Analysis of 15 Different Genome Types of Adenovirus Type 7 Isolated on FiveContinents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of Caenorhabditis Elegans," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of Staphylococcalagr Alleles," Applied and Environmental Microbiology, 2003, vol. 69 (1), pp. 18-23.

Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Little D.P., et al, "Rapid Sequencing of Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 Region of Candidaalbicans and Related Species," Yeast, 1993, vol. 9, pp. 1199-1206.

Louie L., et al., "Evaluation of Three Rapid Methods for Detection of Methicillin Resistance in *Staphylococcus aureus*," Journal of Clinical Microbiology, 2000, vol. 38 (6), pp. 2170-2173.

Love B.C., et al., "Cloning and Sequence of the GroESL Heat-Shock Operon of Pasteurella Multocida," Gene, 1995, vol. 166 (1), pp. 179-180.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, vol. 18 (7), pp. 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiolofy Reviews, 1994, vol. 15 (2-3), pp. 155-173.

Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.

Ma X.X., et al., "Novel Type of Staphylococcal Cassette Chromosome Mec Identified in Community-Acquired Methicillin-Resistant *Staphylococcus aureus* Strains," Antimicrobial Agents and Chemotherapy, 2002, vol. 46 (4), pp. 1147-1152.

Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.

Magnuson V.L., et al., "Substrate Nucleotide-Determined Non-Templated Addition of Adenine by Taq DNA Polymerase: Implications for PCR-Based Genotyping and Cloning," BioTechniques, 1996, vol. 21 (4), pp. 700-709.

Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.

Malasig M.D., et al., "Simplified Microneutralization Test for Serotyping Adenovirus Isolates," Journal of Clinical Microbiology, 2001, vol. 39 (8), pp. 2984-2986.

Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.

Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.

Marcy Y., et al., "Nanoliter Reactors Improve Multiple Displacement Amplification of Genomes from Single Cells," PLoS Genetics, 2007, vol. 3 (9), pp. e155.

Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Separation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elongation Factor (3 from Aquifer aeolicus: Cloning, Expression, Purification,

(56) References Cited

OTHER PUBLICATIONS and Characterization in a Heterologous Translation System," Protein Expression and Purification, 2000, vol. 18 (3), pp. 257-261.

Martineau F., et al., "Development of a PCR Assay for Identification of *Staphylococci* at Genus and Species Levels," Journal of Clinical Microbiology, 2001, vol. 39 (7), pp. 2541-2547.

Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.

Martin-Lopez J.V., et al., "Simultaneous PCR Detection of Ica Cluster and Methicillin and Mupirocinresistance Genes in Catheter-Isolated *Staphylococcus*," International Microbiology, 2004, vol. 7 (1), pp. 63-66.

Mason V.P., et al., "Diversity and linkage of Replication and Mobilisation Genes in *Bacillus* Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonucleotide N3→p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.C., "Percent Sequence Identity: The Need to be Explicit," Structure, 2004, vol. 12 (5), pp. 737-738.

McCabe K.M., et al., "Bacterial Species Identification After DNA Amplification with a Universal Primer Pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.

Meiyu F., et al., "Detection of Flaviviruses by Reverse Transcriptase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of *Staphylococcus aureus* and Methicillin-Resistant *S. Aureus*," Journal of Clinical Microbiology, 2000, vol. 38 (6), pp. 2378-2380.

Merlino J., et al., "Rapid Detection of Non-Multidrug-Resistant and Multidrug-Resistant Methicillin-Resistant *Staphylococcus aureus* Using Cycling Probe Technology for the mecA Gene," European Journal of Clinical Microbiology and Infectious Diseases, 2003, vol. 22 (5), pp. 322-323.

Messmer T.O., et al., "Discrimination of *Streptococcus pneumoniae* from Other Upper respiratory tract *Streptococci* by Arbitrary Primed PCR," Clinical Biochemistry, 1995, vol. 28 (6), pp. 567-572.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondrial DNA Control Region: Development of an International Standard Forensic Database," Croatian Medical Journal, 2001, vol. 42 (3), pp. 315-327.

Miragaia M., et al., "Genetic Diversity among Methicillin-Resistant *Staphylococcus epidemidis*(MRSE)," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "RpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of *Fusarium oxysporum* f.sp. Vasinfectum in Cotton Tissue by Polymerase Chain Reaction," Plant Pathology, 1998, vol. 47 (4), pp. 486-494.

Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.

Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of *Staphylococci* by Polymerase Chain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms'?," Journal of Microbiological Methods, 1998, vol. 33, pp. 211-219.

Nagy M., et al., "Sequence Analysis of Porcine Adenovirus Serotype 5 Fibre Gene: Evidence for Recombination," Virus Genes, 2002, vol. 24 (2), pp. 181-185.

(56) References Cited

OTHER PUBLICATIONS

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene Sequences and Specific Detection for Panton-Valentine Leukocidin," Biochemical and Biophysical Research Communications, 2005, vol. 328 (4), pp. 995-1002.
Nakao H., et al., "Development of a Direct PCR Assay for Detection of the Diphtheria Toxin Gene," Journal of Clinical Microbiology, 1997, vol. 35 (7), pp. 1651-1655.
Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.
Naumov G.I., et al., "Discrimination Between the Soil Yeast Species *Williopsis saturnus* and *Williopsis suaveolens* by the Polymerase Chain Reaction with the Universal Primer N21," Microbiology, 2000, vol. 69 (2), pp. 229-233.
NEB Catalog, 1998/1999, pp. 1, 79, 121 and 284.
Neumann G., et al., "Host Range Restriction and Pathogenicity in the Context of Influenza Pandemic," Emerging Infectious Diseases, 2006, vol. 12 (6), pp. 881-886.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.
Non-Final Office Action dated Feb. 2, 2007 for U.S. Appl. No. 10/844,938, filed May 12, 2004.
Non-Final Office Action dated Oct. 2, 2009 for U.S. Appl. No. 11/929,707, filed Oct. 30, 2007.
Non-Final Office Action dated Aug. 4, 2010 for U.S. Appl. No. 12/049,949, filed Mar. 17, 2008.
Non-Final Office Action dated Apr. 6, 2009 for U.S. Appl. No. 11/331,987, filed Jan. 13, 2006.
Non-Final Office Action dated Apr. 7, 2006 for U.S. Appl. No. 10/964,571, filed Oct. 12, 2004.
Non-Final Office Action dated Aug. 7, 2007 for U.S. Appl. No. 10/844,938, filed May 12, 2004.
Non-Final Office Action dated Jun. 10, 2009 for U.S. Appl. No. 10/844,938, filed May 12, 2004.
Non-Final Office Action dated Jan. 12, 2010 for U.S. Appl. No. 11/491,376, filed Jul. 21, 2006.
Non-Final Office Action dated Oct. 13, 2010 for U.S. Appl. No. 10/754,415, filed Jan. 9, 2004.
Non-Final Office Action dated Sep. 16, 2009 for U.S. Appl. No. 11/233,630, filed Sep. 21, 2005.
Non-Final Office Action dated Apr. 17, 2009 for U.S. Appl. No. 12/211,641, filed Sep. 16, 2008.
Non-Final Office Action dated Nov. 19, 2003 for U.S. Appl. No. 09/798,007, filed Mar. 2, 2001.
Non-Final Office Action dated Aug. 20, 2007 for U.S. Appl. No. 11/582,863, filed Oct. 17, 2006.
Non-Final Office Action dated May 20, 2008 for U.S. Appl. No. 10/844,938, filed May 12, 2004.
Non-Final Office Action dated Oct. 20, 2004 for U.S. Appl. No. 09/891,793, filed Jun. 26, 2001.
Non-Final Office Action dated Feb. 23, 2009 for U.S. Appl. No. 10/660,122, filed Sep. 11, 2003.
Non-Final Office Action dated May 26, 2010 for U.S. Appl. No. 11/869,449, filed Oct. 9, 2007.
Non-Final Office Action dated Jul. 27, 2006 for U.S. Appl. No. 11/209,439, filed Aug. 8, 2005.
Non-Final Office Action dated Jun. 28, 2010 for U.S. Appl. No. 11/930,002, filed Oct. 30, 2007.
Non-Final Office Action dated Sep. 28, 2009 for U.S. Appl. No. 11/930,017, filed Oct. 30, 2007.
Non-Final Office Action dated Dec. 29, 2010 for U.S. Appl. No. 12/616,422, filed Nov. 11, 2009.
Non-Final Office Action dated Apr. 30, 2010 for U.S. Appl. No. 11/930,108, filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Notice of Allowance dated Apr. 1, 2011 for U.S. Appl. No. 11/233,630, filed Sep. 21, 2005.
Notice of Allowance dated Jun. 3, 2009 for U.S. Appl. No. 11/331,978, filed Jan. 13, 2006.
Notice of Allowance dated Aug. 5, 2010 for U.S. Appl. No. 11/233,630, filed Sep. 21, 2005.
Notice of Allowance dated Aug. 6, 2009 for U.S. Appl. No. 10/728,486, filed Dec. 5, 2003.
Notice of Allowance dated Jun. 9, 2011 for U.S. Appl. No. 11/331,987, filed Jan. 13, 2006.
Notice of Allowance dated Jun. 9, 2011 for U.S. Appl. No. 11/491,376, filed Jul. 21, 2006.
Notice of Allowance dated Dec. 10, 2010 for U.S. Appl. No. 11/233,630, filed Sep. 21, 2005.
Notice of Allowance dated Dec. 10, 2010 for U.S. Appl. No. 11/491,376, filed Jul. 21, 2006.
Notice of Allowance dated Nov. 12, 2009 for U.S. Appl. No. 10/728,486, filed Dec. 5, 2003.
Notice of Allowance dated Dec. 15, 2008 for U.S. Appl. No. 11/331,978, filed Jan. 13, 2006.
Notice of Allowance dated Sep. 18, 2009 for U.S. Appl. No. 10/660,998, filed Sep. 12, 2003.
Notice of Allowance dated Nov. 24, 2009 for U.S. Appl. No. 11/331,978, filed Jan. 13, 2006.
Notice of Allowance dated May 25, 2011 for U.S. Appl. No. 11/929,707, filed Oct. 30, 2007.
Notice of Allowance dated Oct. 29, 2009 for U.S. Appl. No. 10/660,122, filed Sep. 11, 2003.
Nubel U.,et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Trans-

(56) References Cited

OTHER PUBLICATIONS form Ion Cyclotron Resonance Mass Spectrometry," Analytical Chemistry, 2001, vol. 73 (18), pp. 4514-4521.

Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.

Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.

Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.

Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.

Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.

Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.

Oberste M.S., et al., "Improved Molecular Identification of Enteroviruses by RT-PCR and Amplicon Sequencing," Journal of Clinical Virology, 2003, vol. 26 (3), pp. 375-377.

Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.

Oberste M.S., et al., "Molecular Phylogeny and Proposed Classification of the Simian Picornaviruses," Journal of Virology, 2002, vol. 76 (3), pp. 1244-1251.

Office Action dated Apr. 1, 2004 for U.S. Appl. No. 10/156,608, filed May 24, 2002.

Office Action dated May 1, 2006 for U.S. Appl. No. 10/660,998, filed Sep. 12, 2003.

Office Action dated Feb. 2, 2011 for U.S. Appl. No. 11/869,449, filed Oct. 9, 2007.

Office Action dated Jan. 2, 2009 for U.S. Appl. No. 11/060,135, filed Feb. 17, 2005.

Office Action dated Jun. 2, 2006 for U.S. Appl. No. 10/933,928, filed Sep. 3, 2004.

Office Action dated Jun. 2, 2008 for U.S. Appl. No. 11/331,978, filed Jan. 13, 2006.

Office Action dated Oct. 2, 2008 for U.S. Appl. No. 11/233,630, filed Sep. 21, 2005.

Office Action dated Oct. 2, 2009 for Japanese Application No. 2005508560 filed Dec. 5, 2003.

Office Action dated Aug. 3, 2006 for U.S. Appl. No. 10/660,998, filed Sep. 12, 2003.

Office Action dated Aug. 3, 2009 for U.S. Appl. No. 11/754,174, filed May 25, 2007.

Office Action dated Dec. 3, 2003 for U.S. Appl. No. 10/325,527, filed Dec. 18, 2002.

Office Action dated Feb. 3, 2011 for U.S. Appl. No. 12/326,800, filed Dec. 2, 2008.

Office Action dated Nov. 3, 2008 for U.S. Appl. No. 10/728,486, filed Dec. 5, 2003.

Office Action dated Apr. 4, 2008 for U.S. Appl. No. 10/829,826, filed Apr. 22, 2004.

Office Action dated Dec. 4, 2006 for Indian Application No. 1136KOLNP2003 filed Mar. 4, 2002.

Office Action dated Feb. 4, 2009 for U.S. Appl. No. 11/404,561, filed Apr. 12, 2006.

Office Action dated Jun. 4, 2009 for U.S. Appl. No. 10/754,415, filed Jan. 9, 2004.

Office Action dated May 4, 2010 for U.S. Appl. No. 90/010,447, filed Apr. 9, 2009.

Office Action dated May 4, 2010 for U.S. Appl. No. 90/010,448, filed Apr. 9, 2009.

Office Action dated Nov. 4, 2009 for European Application No. 02709785.6 filed Mar. 4, 2002.

Office Action dated Sep. 4, 2008 for Australian Application No. 2003297687 filed Dec. 5, 2003.

Office Action dated Aug. 5, 2010 for European Application No. 02709785.6 filed Mar. 4, 2002.

Office Action dated Sep. 5, 2006 for U.S. Appl. No. 10/660,996, filed Sep. 12, 2003.

Office Action dated Jan. 6, 2011 for Israel Application No. 157661 filed Mar. 4, 2002.

Office Action dated Jul. 6, 2006 for U.S. Appl. No. 10/660,122, filed Sep. 11, 2003.

Office Action dated Jul. 6, 2007 for U.S. Appl. No. 10/829,826, filed Apr. 22, 2004.

Office Action dated Mar. 6, 2009 for U.S. Appl. No. 11/233,630, filed Sep. 21, 2005.

Office Action dated Nov. 6, 2002 for U.S. Appl. No. 09/798,007, filed Mar. 2, 2001.

Office Action dated Apr. 7, 2009 for Canadian Application No. 2525498 filed May 13, 2004.

Office Action dated Apr. 7, 2009 for European Application No. 07760292.8 filed Apr. 6, 2007.

Office Action dated Apr. 7, 2009 for U.S. Appl. No. 10/660,998, filed Sep. 12, 2003.

Office Action dated Aug. 7, 2007 for U.S. Appl. No. 10/660,998, filed Sep. 12, 2003.

Office Action dated Feb. 7, 2008 for European Application No. 03796752.8 filed Dec. 5, 2003.

Office Action dated Jun. 7, 2010 for European Application No. 06800205.4 filed Jul. 27, 2006.

Office Action dated Jan. 8, 2003 for U.S. Appl. No. 09/798,007, filed Mar. 2, 2001.

Office Action dated Jan. 8, 2007 for U.S. Appl. No. 09/891,793, filed Jun. 26, 2001.

Office Action dated Mar. 8, 2005 for U.S. Appl. No. 09/891,793, filed Jun. 26, 2001.

Office Action dated Mar. 8, 2007 for U.S. Appl. No. 11/060,135, filed Feb. 17, 2005.

Office Action dated Sep. 8, 2006 for Chinese Application No. 02809122.1 filed Mar. 4, 2002.

Office Action dated Dec. 9, 2004 for U.S. Appl. No. 10/156,608, filed May 24, 2002.

Office Action dated Dec. 9, 2009 for U.S. Appl. No. 90/010,210, filed Jun. 27, 2008.

Office Action dated Dec. 9, 2009 for U.S. Appl. No. 90/010,447, filed Apr. 9, 2009.

Office Action dated Dec. 9, 2009 for U.S. Appl. No. 90/010,448, filed Apr. 9, 2009.

Office Action dated Feb. 9, 2007 for Chinese Application No. 02809122.1 filed Mar. 4, 2002.

Office Action dated Jan. 9, 2008 for Japanese Application No. 2002570692 filed Mar. 4, 2002.

Office Action dated Jul. 9, 2008 for U.S. Appl. No. 10/660,122, filed Sep. 11, 2003.

Office Action dated Jul. 9, 2008 for U.S. Appl. No. 11/331,987, filed Jan. 13, 2006.

Office Action dated Mar. 9, 2004 for U.S. Appl. No. 09/891,793, filed Jun. 26, 2001.

Office Action dated Nov. 9, 2010 for U.S. Appl. No. 11/331,987, filed Jan. 13, 2006.

Office Action dated Dec. 10, 2008 for U.S. Appl. No. 10/829,826, filed Apr. 22, 2004.

Office Action dated Dec. 10, 2009 for U.S. Appl. No. 11/929,910, filed Oct. 30, 2007.

(56) References Cited

OTHER PUBLICATIONS

Office Action dated Feb. 10, 2005 for U.S. Appl. No. 09/798,007, filed Mar. 2, 2001.
Office Action dated Feb. 10, 2006 for Australian Application No. 2002244250 filed Mar. 4, 2002.
Office Action dated Jun. 10, 2009 for U.S. Appl. No. 90/010,210, filed Jun. 27, 2008.
Office Action dated Jun. 10, 2010 for U.S. Appl. No. 90/010,447, filed Apr. 9, 2009.
Office Action dated Jun. 10, 2010 for U.S. Appl. No. 90/010,448, filed Apr. 9, 2009.
Office Action dated Oct. 10, 2007 for U.S. Appl. No. 10/754,415, filed Jan. 9, 2004.
Office Action dated Sep. 10, 2008 for Australian Application No. 2003302236 filed Dec. 5, 2003.
Office Action dated Aug. 11, 2005 for U.S. Appl. No. 09/891,793, filed Jun. 26, 2001.
Office Action dated Aug. 11, 2010 for U.S. Appl. No. 90/010,447, filed Apr. 9, 2009.
Office Action dated Aug. 11, 2010 for U.S. Appl. No. 90/010,448, filed Apr. 9, 2009.
Office Action dated Dec. 11, 2007 for U.S. Appl. No. 10/660,998, filed Sep. 12, 2003.
Office Action dated Jul. 11, 2003 for U.S. Appl. No. 09/798,007, filed Mar. 2, 2001.
Office Action dated Jun. 11, 2010 for U.S. Appl. No. 90/010,210, filed Jun. 27, 2008.
Office Action dated Mar. 11, 2005 for U.S. Appl. No. 10/325,527, filed Dec. 18, 2002.
Office Action dated May 11, 2007 for U.S. Appl. No. 10/728,486, filed Dec. 5, 2003.
Office Action dated Jul. 12, 2006 for U.S. Appl. No. 09/891,793, filed Jun. 26, 2001.
Office Action dated Jul. 12, 2006 for U.S. Appl. No. 10/660,996, filed Sep. 12, 2003.
Office Action dated Jun. 12, 2008 for U.S. Appl. No. 10/754,415, filed Jan. 9, 2004.
Office Action dated Jun. 12, 2009 for Chinese Application No. 200480016187.9 filed May 13, 2004.
Office Action dated May 12, 2002 for U.S. Appl. No. 09/798,007, filed Mar. 2, 2001.
Office Action dated Aug. 13, 2009 for U.S. Appl. No. 11/674,538, filed Feb. 13, 2007.
Office Action dated Jul. 13, 2004 for U.S Appl. No. 09/891,793, filed Jun. 26, 2001.
Office Action dated Jul. 13, 2007 for U.S. Appl. No. 11/233,630, filed Sep. 21, 2005.
Office Action dated Jul. 13, 2010 for U.S. Appl. No. 11/929,930, filed Oct. 30, 2007.
Office Action dated Mar. 13, 2006 for U.S. Appl. No. 10/754,415, filed Jan. 9, 2004.
Office Action dated Nov. 13, 2003 for U.S. Appl. No. 09/891,793, filed Jun. 26, 2001.
Office Action dated Sep. 13, 2006 for U.S. Appl. No. 09/891,793, filed Jun. 26, 2001.
Office Action dated Jul. 14, 2004 for U.S. Appl. No. 10/326,642, filed Dec. 18, 2002.
Office Action dated Jun. 14, 2004 for U.S. Appl. No. 09/891,793, filed Jun. 26, 2001.
Office Action dated Mar. 14, 2011 for U.S. Appl. No. 11/930,002, filed Oct. 30, 2007.
Office Action dated Aug. 15, 2008 for U.S. Appl. No. 11/331,978, filed Jan. 13, 2006.
Office Action dated Dec. 15, 2008 for Israel Application No. 157661 filed Mar. 4, 2002.
Office action dated Dec. 15, 2010 for Canadian Application No. 2508726 filed Dec. 5, 2003.
Office Action dated Jan. 15, 2008 for Israel Application No. 157661 filed Mar. 4, 2002.
Office Action dated Jul. 15, 2009 for U.S. Appl. No. 11/060,135, filed Feb. 17, 2005.
Office Action dated Mar. 15, 2010 for European Application No. 08730682.5 filed Feb. 25, 2008.
Office Action dated Nov. 15, 2007 for U.S. Appl. No. 11/331,978, filed Jan. 13, 2006.
Office Action dated Sep. 15, 2005 for U.S. Appl. No. 10/156,608, filed May 24, 2002.
Office Action dated Apr. 16, 2002 for U.S. Appl. No. 09/798,007, filed Mar. 2, 2001.
Office Action dated Apr. 16, 2008 for U.S. Appl. No. 11/233,630, filed Sep. 21, 2005.
Office Action dated Apr. 16, 2009 for U.S. Appl. No. 90/010,210, filed Jun. 27, 2008.
Office Action dated Aug. 16, 2004 for U.S. Appl. No. 10/325,527, filed Dec. 18, 2002.
Office Action dated Aug. 16, 2010 for U.S. Appl. No. 11/929,707, filed Oct. 30, 2007.
Office Action dated Feb. 16, 2011 for U.S. Appl. No. 11/929,910, filed Oct. 30, 2007.
Office Action dated Jul. 16, 2007 for U.S. Appl. No. 11/331,987, filed Jan. 13, 2006.
Office Action dated Mar. 16, 2006 for U.S. Appl. No. 09/891,793, filed Jun. 26, 2001.
Office Action dated Mar. 16, 2010 for Canadian Application No. 2616281 filed Jul. 21, 2006.
Office Action dated May 16, 2008 for U.S. Appl. No. 11/404,561, filed Apr. 12, 2006.
Office Action dated Nov. 16, 2009 for Japanese Application No. 2005508488 filed Dec. 5, 2003.
Office Action dated Jun. 17, 2008 for U.S. Appl. No. 11/582,863, filed Oct. 17, 2006.
Office Action dated Mar. 17, 2006 for U.S. Appl. No. 10/660,122, filed Sep. 11, 2003.
Office Action dated Nov. 17, 2006 for U.S. Appl. No. 10/754,415, filed Jan. 9, 2004.
Office Action dated Oct. 17, 2007 for U.S. Appl. No. 10/728,486, filed Dec. 5, 2003.
Office Action dated Oct. 17, 2008 for U.S. Appl. No. 11/331,978, filed Jan. 13, 2006.
Office Action dated Sep. 17, 2008 for European Application No. 03796752.8 filed Dec. 5, 2003.
Office Action dated Sep. 17, 2008 for U.S. Appl. No. 10/660,122, filed Sep. 11, 2003.
Office Action dated Feb. 18, 2010 for European Application No. 03814656.9 filed Dec. 5, 2003.
Office Action dated Jan. 18, 2011 for U.S. Appl. No. 11/930,108, filed Oct. 31, 2007.
Office Action dated May 18, 2005 for New Zealand Application No. 527857 filed Mar. 4, 2002.
Office Action dated Sep. 18, 2006 for U.S. Appl. No. 10/660,997, filed Sep. 12, 2003.
Office Action dated Sep. 18, 2008 for Australian Application No. 2003298030 filed Dec. 5, 2003.
Office Action dated Sep. 18, 2008 for U.S. Appl. No. 10/660,998, filed Sep. 12, 2003.
Office Action dated Jan. 19, 2007 for U.S. Appl. No. 11/059,776, filed Feb. 17, 2005.
Office Action dated May 19, 2005 for U.S. Appl. No. 09/891,793, filed Jun. 26, 2001.
Office Action dated Nov. 19, 2004 for U.S. Appl. No. 10/156,608, filed May 24, 2002.
Office Action dated Oct. 19, 2007 for U.S. Appl. No. 11/210,516, filed Aug. 24, 2005.
Office Action dated Sep. 19, 2006 for U.S. Appl. No. 10/660,122, filed Sep. 11, 2003.
Office Action dated Sep. 19, 2007 for U.S. Appl. No. 10/660,122, filed Sep. 11, 2003.
Office Action dated Apr. 20, 2007 for U.S. Appl. No. 10/660,122, filed Sep. 11, 2003.
Office Action dated Apr. 20, 2009 for U.S. Appl. No. 10/891,337, filed Jul. 14, 2004.

(56) References Cited

OTHER PUBLICATIONS

Office Action dated Dec. 20, 2006 for U.S. Appl. No. 10/728,486, filed Dec. 5, 2003.
Office Action dated Jul. 20, 2005 for U.S. Appl. No. 10/156,608, filed May 24, 2002.
Office Action dated Jun. 20, 2002 for U.S. Appl. No. 09/798,007, filed Mar. 2, 2001.
Office Action dated Nov. 20, 2003 for U.S. Appl. No. 10/323,438, filed Dec. 18, 2002.
Office Action dated Nov. 20, 2006 for U.S. Appl. No. 09/891,793, filed Jun. 26, 2001.
Office Action dated Nov. 20, 2006 for European Application No. 02709785.6 filed Mar. 4, 2002.
Office Action dated Sep. 20, 2010 for U.S. Appl. No. 90/010,447, filed Apr. 9, 2009.
Office Action dated Sep. 20, 2010 for U.S. Appl. No. 90/010,448, filed Apr. 9, 2009.
Office Action dated Apr. 21, 2009 for U.S. Appl. No. 90/010,209, filed Jun. 27, 2008.
Office Action dated Mar. 21, 2008 for U.S. Appl. No. 10/660,122, filed Sep. 11, 2003.
Office Action dated May 21, 2008 for U.S. Appl. No. 10/943,344, filed Sep. 17, 2004.
Office Action dated Nov. 21, 2003 for U.S. Appl. No. 10/326,642, filed Dec. 18, 2002.
Office Action dated Nov. 21, 2006 for U.S. Appl. No. 10/660,997, filed Sep. 12, 2003.
Office Action dated Oct. 21, 2005 for U.S. Appl. No. 10/326,641, filed Dec. 18, 2002.
Office Action dated Oct. 21, 2009 for U.S. Appl. No. 12/326,800, filed Dec. 2, 2008.
Office Action dated Apr. 22, 2009 for U.S. Appl. No. 11/491,376, filed Jul. 21, 2006.
Office Action dated Jul. 22, 2008 for U.S. Appl. No. 90/010,209, filed Jun. 27, 2008.
Office Action dated Jul. 22, 2008 for U.S. Appl. No. 90/010,210, filed Jun. 27, 2008.
Office Action dated Nov. 22, 2006 for U.S. Appl. No. 10/660,996, filed Sep. 12, 2003.
Office Action dated Oct. 22, 2007 for U.S. Appl. No. 11/331,987, filed Jan. 13, 2006.
Office Action dated Sep. 22, 2003 for U.S. Appl. No. 09/798,007, filed Mar. 2, 2001.
Office Action dated Sep. 22, 2010 for Canadian Application No. 2510007 filed Dec. 5, 2003.
Office Action dated Apr. 23, 2010 for U.S. Appl. No. 90/010,210, filed Jun. 27, 2008.
Office Action dated Feb. 23, 2009 for U.S. Appl. No. 10/943,344, filed Sep. 17, 2004.
Office Action dated Jan. 23, 2008 for U.S. Appl. No. 10/728,486, filed Dec. 5, 2003.
Office Action dated Jan. 23, 2008 for U.S. Appl. No. 11/059,776, filed Feb. 17, 2005.
Office Action dated May 23, 2003 for U.S. Appl. No. 09/891,793, filed Jun. 26, 2001.
Office Action dated May 23, 2005 for U.S. Appl. No. 10/156,608, filed May 24, 2002.
Office Action dated Oct. 23, 2003 for New Zealand Application No. 527857 filed Mar. 4, 2002.
Office Action dated Apr. 24, 2009 for U.S. Appl. No. 90/010,447, filed Apr. 9, 2009.
Office Action dated Apr. 24, 2009 for U.S. Appl. No. 90/010,448, filed Apr. 9, 2009.
Office Action dated Aug. 24, 2010 for U.S. Appl. No. 90/010,210, filed Jun. 27, 2008.
Office Action dated Dec. 24, 2004 for New Zealand Application No. 527857 filed Mar. 4, 2002.
Office Action dated Feb. 24, 2004 for U.S. Appl. No. 10/326,642, filed Dec. 18, 2002.
Office Action dated Jan. 24, 2005 for U.S. Appl. No. 10/326,642, filed Dec. 18, 2002.
Office Action dated Jan. 24, 2007 for U.S. Appl. No. 10/660,998, filed Sep. 12, 2003.
Office Action dated Jul. 24, 2007 for Mexican Application No. PAA2003007927 filed Sep. 2, 2003.
Office Action dated Jul. 24, 2007 for U.S. Appl. No. 11/060,135, filed Feb. 17, 2005.
Office Action dated Jul. 24, 2009 for U.S. Appl. No. 11/754,182, filed May 25, 2007.
Office Action dated Jun. 24, 2008 for European Application No. 06800205.4 filed Jul. 27, 2006.
Office Action dated Mar. 24, 2011 for U.S. Appl. No. 11/929,930, filed Oct. 30, 2007.
Office Action dated Nov. 24, 2009 for U.S. Appl. No. 90/010,210, filed Jun. 27, 2008.
Office Action dated Sep. 24, 2009 for U.S. Appl. No. 90/010,210, filed Jun. 27, 2008.
Office Action dated Aug. 25, 2009 for U.S. Appl. No. 11/754,169, filed May 25, 2007.
Office Action dated Jun. 25, 2009 for U.S. Appl. No. 11/869,449, filed Oct. 9, 2007.
Office Action dated Jun. 25, 2009 for U.S. Appl. No. 90/010,210, filed Jun. 27, 2008.
Office Action dated Mar. 25, 2008 for U.S. Appl. No. 11/060,135, filed Feb. 17, 2005.
Office Action dated Aug. 26, 2003 for U.S. Appl. No. 09/891,793, filed Jun. 26, 2001.
Office Action dated Aug. 26, 2010 for Canadian Application No. 2508584 filed Dec. 5, 2003.
Office Action dated Jul. 26, 2004 for U.S. Appl. No. 10/323,438, filed Dec. 18, 2002.
Office Action dated May 26, 2005 for U.S. Appl. No. 10/156,608, filed May 24, 2002.
Office Action dated May 26, 2006 for U.S. Appl. No. 10/660,997, filed Sep. 12, 2003.
Office Action dated Feb. 27, 2003 for U.S. Appl. No. 09/798,007, filed Mar. 2, 2001.
Office Action dated Feb. 27, 2007 for U.S. Appl. No. 10/754,415, filed Jan. 9, 2004.
Office Action dated Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action dated Jul. 27, 2009 for Canadian Application No. 2439655 filed Mar. 4, 2002.
Office Action dated Aug. 28, 2006 for U.S. Appl. No. 10/754,415, filed Jan. 9, 2004.
Office Action dated Feb. 28, 2006 for U.S. Appl. No. 10/660,996, filed Sep. 12, 2003.
Office Action dated Jul. 28, 2009 for U.S. Appl. No. 11/754,163, filed May 25, 2007.
Office Action dated Jul. 28, 2010 for U.S. Appl. No. 90/010,210, filed Jun. 27, 2008.
Office Action dated May 28, 2003 for U.S. Appl. No. 09/798,007, filed Mar. 2, 2001.
Office Action dated Mar. 29, 2010 for Australian Application No. 2006272776 filed Jul. 21, 2006.
Office Action dated May 29, 2007 for U.S. Appl. No. 11/059,776, filed Feb. 17, 2005.
Office Action dated Oct. 29, 2009 for U.S. Appl. No. 90/010,447, filed Apr. 9, 2009.
Office Action dated Oct. 29, 2009 for U.S. Appl. No. 90/010,448, filed Apr. 9, 2009.
Office Action dated Aug. 30, 2007 for U.S. Appl. No. 10/754,415, filed Jan. 9, 2004.
Office Action dated Jul. 30, 2008 for Australian Application No. 2004248107 filed Apr. 23, 2004.
Office Action dated Jul. 30, 2009 for Japanese Application No. 2002570692 filed Mar. 4, 2002.
Office Action dated Jun. 30, 2004 for U.S. Appl. No. 09/798,007, filed Mar. 2, 2001.

(56) References Cited

OTHER PUBLICATIONS

Office Action dated Jun. 30, 2010 for U.S. Appl. No. 90/010,210, filed Jun. 27, 2008.
Office Action dated Jun. 30, 2010 for U.S. Appl. No. 90/010,447, filed Apr. 9, 2009.
Office Action dated Jun. 30, 2010 for U.S. Appl. No. 90/010,448, filed Apr. 9, 2009.
Office Action dated May 30, 2006 for U.S. Appl. No. 10/660,996, filed Sep. 12, 2003.
Office Action dated Nov. 30, 2009 for U.S. Appl. No. 10/660,122, filed Sep. 11, 2003.
Office Action dated Sep. 30, 2005 for Chinese Application No. 02809122.1 filed Mar. 4, 2002.
Office Action dated Jan. 31, 2003 for U.S. Appl. No. 09/798,007, filed Mar. 2, 2001.
Office Action dated Jan. 31, 2007 for Philippines Application No. PH12003500824 filed Mar. 4, 2002.
O"Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: The Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run to Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, dated Dec. 16, 2002, 2 pages.
Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pawa A., et al., "Co-Transfer of Plasm ids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, the Market and Prospects for New Antimicrobial Agents," Current Opinion in Microbiology, 2004, vol. 7, pp. 435-438.
Peng X., et al., "Rapid Detection of *Shigella* Species in Environmental Sewage by an Immunocapture PCR with Universal Primers," Applied and Environmental Microbiology, 2002, vol. 68 (5), pp. 2580-2583.
Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.
Peters S.E., et al., "Quantification of the Detection of Pneumocystis Carinii by DNA Amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid Molecular Detection of Microbial Pathogens: Breakthroughs and Challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of Adenovirus using PCR and Molecular Beacon," Journal of Virological Methods, 1999, vol. 82 (1), pp. 19-26.
Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-Based Detection and Typing of Human Adenoviruses in Clinical Samples," Research in Virology, 1997, vol. 148 (3), pp. 225-231.
Promega. T4 Polynucleotide Kinase, Technical Bulletin No. 519, 2002.
Puthavathana P., et al., "Molecular Characterization of the Complete Genome of Human Influenza H5N1 Virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.

(56) References Cited

OTHER PUBLICATIONS

Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Ramisse V., et al., "Identification and Characterization of *Bacillus anthracis* by Multiplex PCR Analysis of Sequences on Plasmids pX01 and pX02 and Chromosomal DNA," Fems Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of *Bacillus subtilis* and *Bacillus mojavensis*," Evolution, 1995, vol. 49 (6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleoprotein Gene of Influenza B/Ann Arbor/1/86," Nucleic Acids Research, 1989, vol. 17 (9), pp. 3595.
Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus* Mutans by using Competitive Polymerasechain Reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of Pcr-Based Methods for Typing *Staphylococcus aureus* Isolates," Journal of Clinical Microbiology, 2006, vol. 44 (10), pp. 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative *Staphylococci* in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4- Carboxamide During PCR," Nucleic Acids Research, 1996, vol. 24 (17), pp. 3302-3306.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and Molecular Characterization of Ebola Viruses Causing Disease in Human and Nonhuman Primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.
Santos S.R., et al., "Identification and Phylogenetic Sorting of Bacterial Lineages with Universally Conserved Genes and Proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," the Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.
Schlecht N.F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a Marine Pikoplankton Community by 16s rRNA Gene Cloning and Sequencing," Journal of Bacteriology, 1991, vol. 173 (14), pp. 4371-4378.
Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.
Schmitz F.J., et al., "Development of Resistance to Ciprofloxacin, Rifampin, and Mupirocin in Methicillin-Susceptible and -Resistant

(56) References Cited

OTHER PUBLICATIONS

*Staphylococcus aureus* Isolates," Antimicrobial Agents and Chemotherapy, 2000, vol. 44 (11), pp. 3229-3231.
Schmitz F.J., et al., "Specific Information Concerning Taxonomy, Pathogenicity and Methicillin Esistance of *Staphylococci* Obtained by a Multiplex PCR," Journal of Medical Microbiology, 1997, vol. 46 (9), pp. 773-778.
Schram K.H., et al., "Mass Spectrometry of Nucleic Acid Components," Methods of Biochemical Analysis, 1990, vol. 34, pp. 203-280.
Schultz J.C., et al., "Polymerise Chain Reaction Products Analyzed by Charge Detection Mass Spectrometry," Rapid Communications in Mass Spectrometry, 1999, vol. 13 (1), pp. 15-20.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.
Sciacchitano C.J., "Analysis of Polymerase Chain Reaction-Amplified DNA Fragments of *Clostridium botulinum* Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of *Bacilus subtilis* Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the Gene for Toxic Shock Syndrome Toxin 1 in *Siaphylococcusaureus* by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus*," Journal of Clinical Microbiology, 1994, vol. 32 (8), pp. 1866-1869.
Shrestha N.K., et al., "Rapid Identification of *Staphylococcus aureus* and the MecA Gene from BacT/Alert Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from *Bacilus thuringiensis* Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and the Avian H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjinand Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of *Staphylococci*," Journal of Clinical Pathology, 2003, vol. 56 (10), pp. 782-785.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, dated Jul. 7, 2008, 8 pages.
Supplementary European Search Report for Application No. EP03796752.8, dated Aug. 7, 2007, 3 pages.
Supplementary European Search Report for Application No. EP03810055.8, dated Jun. 8, 2007, 4 pages.

(56) References Cited

OTHER PUBLICATIONS

Supplementary European Search Report for Application No. EP03814656, dated Oct. 16, 2007, 2 pages.
Supplementary European Search Report for Application No. EP04752257.8, dated Feb. 15, 2006, 2 pages.
Supplementary European Search Report for Application No. EP05753037, dated Aug. 21, 2009, 2 pages.
Supplementary Partial European Search Report for Application No. EP02709785.6, dated Sep. 1, 2005, 5 pages.
Supplementary Partial European Search Report for Application No. EP05751872.2, dated Jan. 28, 2008, 8 pages.
Supplementary Partial European Search Report for Application No. EP05856582.1, dated Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—A Critical Review," Microbes and Infection / Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.
Takagaki Y., et al., "Four Factors are Required for 3"-End Cleavage of Pre-mRNAs," Genes and Development, 1989, vol. 3 (11), pp. 1711-1724.
Takahashi H., et al., "Characterization of gryA, gryB, grlA and grlB Mutations in Fluoroquinolone-Resistant Clinical Isolates of *Staphylococcus aureus*," The Journal of Antimicrobial Chemotherapy, 1998, vol. 41 (1), pp. 49-57.
Takahata M., et al., "Mutations in the GyrA and Gr1A Genes of Quinolone-Resistant Clinical Isolates of Methicillin-Resistant *Staphylococcus aureus*," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Talaat A.M., et al., "Genome-Directed Primers for Selective Labeling of Bacterial Transcripts for DNA Microarray Analysis," Nature Biotechnology, 2000, vol. 17, pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.

Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.
Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.
Top F.H Jr., "Control of Adenovirus Acute Respiratory Disease in U.S. Army Trainees," The Yale Journal of Biology and Medicine, 1975, vol. 48 (3), pp. 185-195.
Torroni A., et al., "Classification of European mtDNAs from an Analysis of Three European Populations," Genetics, 1996, vol. 144 (4), pp. 1835-1850.
Towner K.J., et al., "Development and Evaluation of a PCR-Based Immunoassay for the Rapid Detection of Methicillin-Resistant *Staphylococcus Aureus*," Journal of Medical Microbiology, 1998, vol. 47 (7), pp. 607-613.
Tsuneyoshi T., et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.
Udo E.E., et al., "Rapid Detection of Methicillin Resistance in *Staphylococci* Using a Slide Latex Agglutination Kit," International Journal of Antimicrobial Agents, 2000, vol. 15 (1), pp. 19-24.
Unal S., et al., "Detection of Methicillin-Resistant *Staphylococci* by Using the Polymerase Chain Reaction," Journal of Clinical Microbiology, 1992, vol. 30 (7), pp. 1685-1691.
Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.
Vabret A., et al., "Development of a PCR-and Hybridization-Based Assay (PCR Adenovirus Consensus) for the Detection and the

(56) References Cited

OTHER PUBLICATIONS

Species Identification of Adenoviruses in Respiratory Specimens," Journal of Clinical Virology, 2004, vol. 31 (2), pp. 116-122.
Van Aerschot A., et al., "In Search of Acyclic Analogues as Universal Nucleosides in Degenerate Probes," Nucleosides and Nucleotides, 1995, vol. 14 (3-5), pp. 1053-1056.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Der Zee H., et al., "Rapid and Alternative Screening Methods for Microbiological Analysis," Journal of AOAC International, 1997, vol. 80 (4), pp. 934-940.
Van Dinten L.C., et al., "Proteolytic Processing of the Open Reading Frame lb-EncodedPart of Arterivirus Replicase Is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," The British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Ert M.N., et al., "Mass Spectrometry Provides Accurate Characterization of Two Genetic Marker Types in *Bacillus anthracis*," Bio Techniques, 2004, vol. 37 (4), pp. 642-651.
Van Leeuwen W.B., et al., "Multilocus Sequence Typing of *Staphylococcus aureus* with DNA Array Technology," Journal of Clinical Microbiology, 2003, vol. 41 (7), pp. 3323-3326.
Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Vannuffel P., et al., "Specific Detection of Methicillin-Resistant *Staphylococcus* Species by Multiplex Pcr," Journal of Clinical Microbiology, 1995, vol. 33 (11), pp. 2864-2867.
Verma S., et al., "Modified Oligonucleotides: Synthesis and Strategy for Users," Annual Review of Biochemistry, 1998, vol. 67, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.
Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative *Staphylococci*," The Lancet Infectious Diseases, 2002, vol. 2 (11), pp. 677-685.
Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.
Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease VIII," DNA Repair, 2003, vol. 2 (5), pp. 441-453.
Wallet F., et al., "Choice of a Routine Method for Detecting Methicillin-Resistance in *Staphylococci*," The Journal of Antimicrobial Chemotherapy, 1996, vol. 37 (5), pp. 901-909.
Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.
Wang G., et al., "Targeted Mutagenesis in Mammalian Cells Mediated by Intracellular Triple Helix Formation," Molecular and Cellular Biology, 1995, vol. 15 (3), pp. 1759-1768.
Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: The gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant*Staphylococcus aureus*," Journal of Clinical Microbiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.
Williams R., et al., "Amplification of Complex Gene Libraries by Emulsion PCR," Nature Methods, 2006, vol. 3 (7), pp. 545-550.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wolter A., et al., "Negative Ion Fab Mass Spectrometric Analysis of Non-Charged Key Intermediates in Oligonucleotide Synthesis:

(56) References Cited

OTHER PUBLICATIONS

Rapid Identification of Partially Protected Dinucleoside Monophosphates," Biomedical and Environmental Mass Spectrometry, 1987, vol. 14, pp. 111-116.
Woo T.H., et al., "Identification of Leptospira Inadai by Continuous Monitoring of Fluorescence during Rapid Cycle PCR," Systematic and Applied Microbiology, 1998, vol. 21 (1), pp. 89-96.
Wood S.R., et al., "Rapid Detection and Serotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.
Written Opinion for Application No. PCT/US2004/33742, dated May 15, 2006, 5 pages.
Written Opinion for Application No. PCT/US2008/065332, dated Nov. 28, 2008, 7 pages.
Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Wunschel D., et al., "Discrimination Among the *B. Cereus* Group, in Comparison to *B. Subtilis*, by Structural Carbohydrate Profiles and Ribosomal RNA Spacer Region PCR," Systematic and Applied Microbiology, 1994, vol. 17, pp. 625-635.
Wunschel D.S., et al., "Analysis of Double-Stranded Polymerase Chain Reaction Products from the *Bacilus cereus* Group by Electrospray Lonization Fourier Transform Lon Cyclotron Resonance Mass Spectrometry," Rapid Communications in Mass Spectrometry, 1996, vol. 10 (1), pp. 29-35.
Wunschel D.S., et al., "Heterogeneity in *Bacillus cereus* PCR Products Detected by ESI-FTICR Mass Spectrometry," Analytical Chemistry, 1998, vol. 70 (6), pp. 1203-1207.
Wunschel D.S., et al., "Mass spectrometric characterization of DNA for molecular biological applications: advances using MALDI and ESI," Advances in Mass Spectrometry, 1998, vol. 14, Elsevier, pp. 377-406.
Xu L., et al., "Electrophore Mass Tag Dideoxy DNA Sequencing," Analytical Chemistry, 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1 N2) Reassortant Viruses During the 2001-2002 Influenza Season," The Journal of Infectious Diseases, 2002, vol. 186 (10), pp. 1490-1493.
Yao Z.P., et al., "Mass Spectrometry Based Proteolytic Mapping for Rapid Virus Identification," Analytical Chemistry, 2002, vol. 74 (11), pp. 2529-2534.
Yasui T., et al., "A Specific Oligonucleotide Primer for the Rapid Detection of Lactobacillus Lindneri by Polymerase Chain Reaction," Canadian Journal of Microbiology, 1997, vol. 43 (2), pp. 157-163.
Ye K., et al., "Three Distinct Promoters Direct Transcription of Different 5" Untranslated Regions of the Human Interleukin 1 Type 1 Receptor. A Possible Mechanism for Control of Translation, Cytokine, 1996, vol. 8 (6), pp. 421-429.
Yun H.J., et al., "Increased Antibacterial Activity of OW286, a Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), pp. 1457-1468.
Zhang J., et al., "PowerBLAST: A New Network BLAST Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of *Staphylococcus aureus* from Coagulase-Negative *Staphylococci*," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming *Staphylococcus epidermidis* Strain (ATCC 12228)," Molecular Microbiology, 2003, vol. 49 (6), pp. 1577-1593.
Dean F.B., et al., "Comprehensive Human Genome Amplification Using Multiple Displacement Amplification," Proceedings of the National Academy of Sciences, 2002, vol. 99 (8), pp. 5261-5266.
Final Office Action dated Jul. 25, 2012 for U.S. Appl. No. 12/602,641, filed Jun. 7, 2010.
Spiess A.N., et al., "A Highly Efficient Method for Long-Chain cDNA Synthesis Using Trehalose and Betaine," Analytical Biochemistry, 2002, vol. 301 (2), pp. 168-174.
Extended European Search Report for Application No. EP10824195.1, dated May 23, 2014, 5 pages.
Non-Final Office Action dated May 9, 2014 for U.S. Appl. No. 12/602,641, filed Jun. 7, 2010.
Extended European Search Report for Application No. EP10824195.1, dated Apr. 8, 2013, 6 pages.
Extended European Search Report for Application No. EP10824195.1, dated Dec. 11, 2013, 4 page.
Mazutis L., et al., "Droplet-based Microfluidic Systems for High-throughput Single DNA Molecule Isothermal Amplification and Analysis," Analytical Chemistry, 2009, vol. 81 (12), pp. 4813-4821.
Final Office Action dated Dec. 24, 2014 for U.S. Appl. No. 12/602,641, filed Jun. 7, 2010.
Blanco L., et al., "Highly Efficient Dna Synthesis by the Phage Phi 29 Dna Polymerase. Symmetrical Mode of Dna Replication," The Journal of Biological Chemistry, 1989, vol. 264 (15), pp. 8935-8940.
Blyn B., et al., "Rapid Detection and Molecular Serotyping of Adenovirus by Use of PCR Followed by Electrospray Ionization Mass Spectrometry," Journal of Clinical Microbiology, 2008, vol. 46 (2), pp. 644-651.
Ecker D.J., et al., "The Microbial Rosetta stone Database: A Compilation of Global and Emerging Infectious Microorganisms and Bioterrorist Threat Agents," BMC Microbiology, 2005, vol. 5, pp. 19.
Ecker J.A., et al., "Identification of Acinetobacter Species and Genotyping of *Acinetobacter baumannii* by Multilocus PCR and Mass Spectrometry," Journal of Clinical Microbiology, 2006, vol. 44 (8), pp. 2921-2932.
Eshoo M.W., et al., "Direct Broad-range Detection of Alphaviruses in Mosquito Extracts," Virology, 2007, vol. 368 (2), pp. 286-295.
Gallo M., et al., "2'-C-Methyluridine Phosphoramidite: A New Building Block for the Preparation of RNA Analogues Carrying the 2'-Hydroxyl Group," Tetrahedron, 2001, vol. 57 (27), pp. 5707-5713.
Guillerm D., et al., "Synthesis of 4'-Fluoroadenosine as an Inhibitor of S-Adenosyl-L-Homocysteine Hydrolase," Bioorganic & Medicinal Chemistry Letters, 1995, vol. 5 (14), pp. 1455-1460.
Hannis J.C., et al., "High-Resolution Genotyping of *Campylobacter* Species by Use of PCR and High-Throughput Mass Spectrometry," Journal of Clinical Microbiology, 2008, vol. 46 (4), pp. 1220-1225.
Harry-O'Kuru R.E., et al., "A Short, Flexible Route toward 2'-C-Branched Ribonucleosides," The Journal of Organic Chemistry, 1997, vol. 62 (6), pp. 1754-1759.
Hofstadler S.A., et al., "Selective Ion Filtering by Digital Thresholding: A Method to Unwind Complex ESI-Mass Spectra and Eliminate Signals from Low Molecular Weight Chemical Noise," Analytical Chemistry, 2006, vol. 78 (2), pp. 372-378.

(56) References Cited

OTHER PUBLICATIONS

Hosfstadler S. A., et al., "Detection of Microbial Agents Using Broad-Range PCR with Detection by Mass Spectrometry," In: The TIGER Concept, Miller M.J., Eds., Encyclopedia of Rapid Microbiological Methods, Parenteral Drug Association, Bethesda, MD, 2005, vol. 3, pp. 287-307.

Hujer K.M., et al., "Analysis of Antibiotic Resistance Genes in Multidrug-resistant *Acinetobacter* Sp. Isolates from Military and Civilian Patients Treated at the Walter Reed Army Medical Center," Antimicrob Agents Chemother, 2006, vol. 50 (12), pp. 4114-4123.

Hutchison C.A., et al., "Cell-Free Cloning Using Phi29 DNA Polymerase," Proceedings of the National Academy of Sciences of the United States of America, 2005, vol. 102 (48), pp. 17332-17336.

Jacobson K.A., et al., "Methanocarba Analogues of Purine Nucleosides as Potent and Selective Adenosine Receptor Agonists," Journal of Medicinal Chemistry, 2000, vol. 43 (11), pp. 2196-2203.

Kawasaki A.M., et al., "Uniformly Modified 2'-Deoxy-2'-Fluoro Phosphorothioate Oligonucleotides as Nuclease-Resistant Antisense Compounds with High Affinity and Specificity for RNA Targets," Journal of Medicinal Chemistry, 1993, vol. 36 (7), pp. 831-841.

Kittler R., et al., "A Whole Genome Amplification Method to Generate Long Fragments from Low Quantities of Genomic DNA," Analytical Biochemistry, 2002, vol. 300 (2), pp. 237-244.

Koshkin A.A., et al., "LNA (Locked Nucleic Acids) : Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, 1998, vol. 54, pp. 3607-3630.

Kumar R., et al., "The First Analogues of LNA (Locked Nucleic Acids): Phosphorothioate-LNA and 2'-Thio-LNA," Bioorganic Medicinal Chemistry Letters, 1998, vol. 8 (16), pp. 2219-2222.

Lage J.M., et al., "Whole Genome Analysis of Genetic Alterations in Small DNA Samples Using Hyperbranched Strand Displacement Amplification and Array-CGH," Genome Research, 2003, vol. 13 (2), pp. 294-307.

Lasken R.S., et al., "Whole Genome Amplification: Abundant Supplies of DNA from Precious Samples or Clinical Specimens," Trends in Biotechnology, 2003, vol. 21 (12), pp. 531-535.

Lee K., et al., "Ring-Constrained (N)-Methanocarba Nucleosides as Adenosine Receptor Agonists: Independent 5'Uronamide and 2'-Deoxy Modifications," Bioorganic Medicinal Chemistry Letters, 2001, vol. 11 (10), pp. 1333-1337.

Lizardi P.M., et al., "Mutation Detection and Single-molecule Counting using Isothermal Rolling-circle Amplification," Nature Genetics, 1998, vol. 19 (3), pp. 225-232.

Owen G.R., et al., "4'-Substituted Nucleosides. 3. Synthesis of Some 4'-Fluorouridine Derivatives," The Journal of Organic Chemistry, 1976, vol. 41 (18), pp. 3010-3017.

Sampath R. et al., "Learning from SARS: Preparing for the Next Disease Outbreak: Workshop Summary," in: Institute of Medicine (US) Forum on Microbial Threats, Knobler S.E., et al., Eds., The National Academies Press, Washington, D.C., 2004, pp. 181-185.

Sanger W., "Principles of Nucleic Acid Structure," 1984, Springer Advanced Texts in Chemistry, table of contents only.

Singh S.K., et al., "Synthesis of 2'-Amino-LNA: a Novel Conformationally Restricted High-Affinity Oligonucleotide Analogues with a Handle," The Journal of Organic Chemistry, 1998, vol. 63, pp. 10035-10039.

Tang X.Q., et al., "2'-C-Branched Ribonucleosides: Synthesis of the Phosphoramidite Derivatives of 2'-C-Beta-Methylcytidine and their Incorporation Into Oligonucleotides," The Journal of Organic Chemistry, 1999, vol. 64 (3), pp. 747-754.

Telenius H., et al., "Degenerate Oligonucleotide-primed PCR: General Amplification of Target Dna by a Single Degenerate Primer," Genomics, 1992, vol. 13 (3), pp. 718-725.

Wortmann G., et al., "Genotypic Evolution of Acinetobacter Baumannii Strains in an Outbreak Associated with War Trauma," Infection Control and Hospital Epidemiology, 2008, vol. 29 (6), pp. 553-555.

Zhang L., et al., "Whole Genome Amplification from a Single Cell: Implications for Genetic Analysis," Proceedings of the National Academy of Sciences of the United States of America, 1992, vol. 89 (13), pp. 5847-5851.

Final Office Action dated Nov. 27, 2015 for U.S. Appl. No. 12/602,641, filed Jun. 7, 2010.

Jeyaprakash A., et al., "Multiple Displacement Amplification in Combination with High-Fidelity PCR Improves Detection of Bacteria from Single Females or Eggs of Metaseiulus Occidentalis (Nesbitt) (Acari: Phytoseiidae)," Journal of Invertebrate Pathology, 2004, vol. 86 (3), pp. 111-116.

Jiang Y., et al., "Mitochondrial DNA Mutation Detection by Electrospray Mass Spectrometry," Clinical Chemistry, 2007, vol. 53 (2), pp. 195-203.

Non-Final Office Action dated Jun. 16, 2015 for U.S. Appl. No. 12/602,641, filed Jun. 7, 2010.

Alsmadi O., et al., "Specific and Complete Human Genome Amplification with Improved Yield Achieved by Phi29 DNA Polymerase and a Novel Primer at Elevated Temperature," BMC Research Notes, 2009, vol. 24 (2), p. 48.

European Search Report for Application No. EP15167348, dated Sep. 24, 2015, 5 pages.

McIntyre G.J., et al., "Design and Cloning Strategies for Constructing Shma Expression Vectors," BMC Biotechnology, 2006, vol. 6 (1).

Non-Final Office Action dated May 3, 2016 for U.S. Appl. No. 12/602,641, filed Jun. 7, 2010.

First Office Action dated Aug. 9, 2016 for Chinese Application No. CN201380061295 filed Sep. 26, 2013.

Notice of Allowance dated Nov. 4, 2016 for U.S. Appl. No. 12/602,641, filed Jun. 7, 2010.

Extended European Search Report dated Aug. 25, 2017 in copending European patent application No. 17171154.2.

\* cited by examiner

MULTIPLE DISPLACEMENT AMPLIFICATION

CROSS-REFERENCE TO RELATED APPLICATION

The present Application claims priority to U.S. Provisional Application Ser. No. 61/252,065 filed Oct. 15, 2009, the entirety of which is herein incorporated by reference.

FIELD OF THE INVENTION

The present invention is directed to the field of amplification of nucleic acids and more particularly to methods for performing multiple displacement amplification reactions.

BACKGROUND OF THE INVENTION

In genetic research, diagnosis or forensic investigations, the scarcity of genomic DNA can be a severely limiting factor on the type and quantity of genetic tests that can be performed on a sample. One approach designed to overcome this problem is whole genome amplification. The objective is to amplify a limited DNA sample in a non-specific manner in order to generate a new sample that is indistinguishable from the original but with a higher DNA concentration. The aim of a typical whole genome amplification technique would be to amplify a sample up to a level sufficient to perform multiple tests and archiving procedures, while maintaining an accurate representation of the original sequence.

The first whole genome amplification methods were described in 1992, and were based on the principles of the polymerase chain reaction (PCR). Zhang and coworkers (Zhang et al. *Proc. Natl. Acad. Sci. U.S.A.* 1992, 89, 5847-5851) developed the primer extension PCR technique (PEP) and Telenius and collaborators (Telenius et al., *Genomics* 1992, 13, 718-725) designed the degenerate oligonucleotide-primed PCR method (DOP-PCR).

PEP involves a high number of PCR cycles using Taq polymerase and 15 base random primers that anneal at a low stringency temperature. Although the PEP protocol has been improved in different ways, it still results in incomplete genome coverage, failing to amplify certain sequences such as repeats. Failure to prime and amplify regions containing repeats may lead to incomplete representation of a whole genome because consistent primer coverage across the length of the genome is required for complete representation of the genome. This method also has limited efficiency on very small samples (such as single cells). Moreover, the use of Taq polymerase is optimized for a maximal product length of about 3 kb. DOP-PCR is a method which uses Taq polymerase and semi-degenerate oligonucleotides that bind at a low annealing temperature at approximately one million sites within the human genome. The first cycles are followed by a large number of cycles with a higher annealing temperature, allowing only for the amplification of the fragments that were tagged in the first step. This leads to incomplete representation of a whole genome. DOP-PCR generates, like PEP, fragments that are in average 400-500 bp, with a maximum size of 3 kb, although fragments up to 10 kb have been reported. On the other hand, as noted for PEP, a low input of genomic DNA (less than 1 ng) decreases the fidelity and the genome coverage (Kittler et al. *Anal. Biochem.* 2002, 300, 237-244).

Multiple displacement amplification (MDA, is a non-PCR-based isothermal method based on the annealing of random hexamers to denatured DNA, followed by strand-displacement synthesis at constant temperature (Blanco et al. *J. Biol. Chem.* 1989, 264, 8935-8940). It has been applied to samples with small quantities of genomic DNA, leading to the synthesis of high molecular weight DNA with limited sequence representation bias (Lizardi et al. *Nature Genetics* 1998, 19, 225-232; Dean et al., *Proc. Natl. Acad. Sci. U.S.A.* 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. *Trends Biotech.* 2003, 21, 531-535).

The methods described above generally do not successfully amplify DNA samples when the quantity of template DNA being amplified is below the level of one 1 nanogram (ng). Problems encountered during such amplification attempts include, for example, poor representation of the original template DNA in the amplified product (Dean et al. *Proc. Natl. Acad. Sci U.S.A.* 2002, 99, 5261-5266) and competing amplification of non-template DNA (Lage et al. *Genome Research* 2003, 13, 294-307).

It has been established that a problem encountered when small amounts of template are amplified using Phi29 DNA polymerase is that "background" DNA synthesis usually occurs when template is omitted, or at low template concentrations. Reducing the reaction volume while keeping the amount of template fixed increases the template concentration, results in a suppression of background synthesis (Hutchinson, C. A. III et al., *Proc. Natl. Acad. Sci. U.S.A.* 2005, 102, 17332-17336). Another issue is poor representation and balance of the DNA of interest following whole genome amplification (WGA).

There remains a long felt need for methods and kits for performing whole genome amplification reactions on small quantities of DNA than maintains the genetic balance and representation of the original sample. The present invention satisfies this need.

SUMMARY OF THE INVENTION

Development of improved procedures for multiple displacement amplification of nucleic acids present at trace levels in a sample would eliminate the need for culturing cells and requires only a few non-viable cells to obtain sufficient DNA for the reaction. Such an improved process would enhance sensitivity in various DNA analysis methods and even produce sufficient nucleic acid for whole genome sequencing. It is advantageous if representation and allelic balance are maintained in addition to obtaining efficient yields of amplified nucleic acid.

It has been recognized that performing multiple displacement amplification reactions in a reaction mixture containing a detergent or in an emulsion format will result in improved representation of the original template sequence as well as providing improved allelic balance in downstream genetic profiling assays. Without being bound to any particular theory, it is believed that performing the amplification reactions in an emulsion format results in capture of individual template nucleic acid molecules within emulsion micro-droplets. This provides for amplification of the template nucleic acid while minimizing interference from background nucleic acid molecules. It is also thought that the emulsion format provides more efficient amplification of smaller or low copy number fragments of the target genome.

In one aspect, there is provided a method for amplifying nucleic acids. The method includes the steps of contacting a sample of nucleic acid with a reaction mixture comprising a set of oligonucleotide primers, one or more polymerase enzymes and an emulsion-forming component and subjecting the reaction mixture to conditions under which the nucleic acid sequence is amplified to produce an amplified product in a multiple displacement reaction. In some embodiments, the emulsion-forming component is a non-ionic detergent such as Tween 20, Tween 40, Tween 80, Triton X 100 or Triton X 102. In some preferred embodiments, the non-ionic detergent is present in the reaction mixture at a level between about 0.05% to about 3% (w/v).

In other embodiments, it is advantageous to further include betaine, trehalose or both betaine and trehalose as stabilizing agents. Advantageously, betaine is present in the reaction mixture at a concentration between about 0.2 M to about 1.6 M and trehalose is present in the reaction mixture at a concentration between about 0.1 M and 1.0 M.

In some embodiments, the polymerases in the reaction mixture comprise 5'→3' DNA polymerase activity, 3'→5' exonuclease activity, and 5'→3' excision repair activity. Advantageously, the polymerases include Phi29 polymerase, Bst DNA polymerase, Pol I polymerase, and/or a component thereof. In some embodiments, Phi29 polymerase is included in the reaction mixture at a concentration between about 0.2 units/µL to about 0.6 units/µL. In some embodiments, Pol I polymerase is included in the reaction mixture at a concentration between about 0.005 units/µL to about 0.015 units/µL of Pol I polymerase.

In some embodiments, dimethylsulfoxide (DMSO) is employed as a further stabilizing agent that enhances strand separation for the amplification reaction and may be included at a concentration of about 1% to about 5%.

Bovine serum albumin (BSA) is included in some embodiments of the method. Without being bound to any particular theory, it is believed that BSA prevents loss of polymerase activity through non-specific binding of the polymerase enzymes to glass or plastic container walls during the amplification process. It has been discovered that commercially obtained BSA is usually significantly contaminated with other biomolecules, particularly nucleic acids. It is advantageous to treat the BSA and other reagents/stabilizing agents to remove contaminating nucleic acids prior to performing multiple displacement amplification reactions.

In some embodiments, the reaction mixture further includes enzyme activators and reagent solubilizing agents such as a magnesium ion (e.g., from an ionic compound, such as magnesium chloride or the like), ammonium sulfate and dithiothreitol. In some embodiments, the reaction mixture includes magnesium chloride at a concentration ranging between about 2 mM to about 20 mM. In some embodiments, the reaction mixture includes ammonium sulfate at a concentration ranging between about 2 mM to about 15 mM. In some embodiments, the reaction mixture includes dithiothreitol at a concentration ranging between about 1 mM to about 8 mM.

In some embodiments, the reaction mixture further includes pyrophosphatase for removal of pyrophosphate generated from the deoxynucleoside triphosphates used in the amplification reaction. Advantageously, pyrophosphatase is present in the reaction mixture at a concentration ranging between about $3\times10^{-5}$ units/µL to about $1\times10^{-4}$ units/µL.

In some embodiments, the reaction mixture is buffered at a pH ranging between about 7.1 to about 7.8 by TRIS or other suitable buffering agent known to those skilled in the art.

In some embodiments, the emulsion-forming component is a hydrophobic polymer such as polydimethylsiloxane or mineral oil for example. Advantageously, polydimethylsiloxane is present in the reaction mixture at a 4:1 ratio of polydimethylsiloxane to aqueous solution.

Upon completion of the multiple displacement amplification reaction, the emulsion must be broken by an emulsion-breaking compound to enable withdrawal of nucleic acids for further analysis. Advantageously, the emulsion-breaking component is chloroform or ethanol.

Once the amplified nucleic acid is obtained, it may be then further analyzed. The amplified nucleic acid may represent an entire genome of an organism. It may be advantageous to prepare one or more additional amplification products representing targeted regions of the genome for further analysis. In some embodiments, a targeted segment is amplified by a conventional polymerase chain reaction to obtain a second amplification product. This second amplification product may be analyzed by base composition analysis using mass spectrometry, for example. In this embodiment, sequencing of the amplification is not necessary in order to determine the base composition.

In other embodiments, the second amplification product is analyzed by determining its sequence. This may be performed using conventional Sanger sequencing methods or any of the "next generation" rapid sequencing methods known to those skilled in the art which include, but are not limited to pyrosequencing, SOLiD™ sequencing, single molecule real time sequencing, nanosequencing, tSMS™ sequencing, single molecule sequencing by synthesis, and nanopore sequencing.

Another aspect is a kit for performing multiple displacement amplification of a nucleic acid. The kit includes one or more polymerases, a plurality of primers and an emulsion-forming component. In some embodiments of the kit, the emulsion forming components are a detergent and a hydrophobic polymer. In this embodiment, the detergent is preferably a non-ionic detergent. The non-ionic detergent may be selected from the group consisting of Tween 20, Tween 40, Tween 80, Triton X 100 and Triton X 102. Tween 40 is a preferred non-ionic detergent. In some embodiments where a hydrophobic polymer is used, the hydrophobic polymer is preferably polydimethylsiloxane.

In some embodiments of the kit, the polymerases have 5'→3' DNA polymerase activity, and optionally 3'→5' exonuclease activity, and/or 5'→3' excision repair activity. In some embodiments, for example, the polymerases include pol I, Bst DNA polymerase and/or Phi29.

In some embodiments, the kit may further include any combination of amplification reaction stabilizing reagents selected from the group consisting of: betaine, trehalose, bovine serum albumin, dimethylsulfoxide, dithiothreitol, ammonium sulfate, magnesium chloride, pyrophosphatase, and polyadenylic acid. Preferably the reagents of the kit are treated to remove contaminating nucleic acids prior to inclusion in said kit.

In some embodiments, the kit includes instructions for performing a multiple displacement amplification reaction on a nucleic acid sample.

In another aspect, a system for analyzing nucleic acids is provided. The system includes a thermal cycler, a container for holding a reaction mixture, and one or more liquid handlers configured to deliver a nucleic acid sample to the container as well as for delivery of an emulsion-breaking compound to the container. The container is configured for insertion into the thermal cycler and is chemically compatible with one or more detergents or hydrophobic solvents used to form an emulsion of the reaction mixture in the container. In some embodiments, the container is a tube, a 96-well plate, a 384-well plate or a microfluidics device which is compatible with compounds of the kit described above.

In some embodiments, the system further includes a downstream nucleic acid analysis apparatus which is configured to receive amplified nucleic acid from the container. The apparatus includes a second thermal cycler configured to perform a targeted second amplification of amplified nucleic acid produced by the system. A purification unit is also included in this apparatus. The purification unit is configured to purify a product of the targeted second amplification. A nucleic acid analysis unit for determining the base composition or sequence of said targeted second amplification product is also included. In some embodiments, the purification unit includes an anion exchange resin linked to a magnetic bead.

In some embodiments, the nucleic acid analysis unit comprises a mass spectrometer or a nucleic acid sequencer. The mass spectrometer may be an electrospray time-of-flight mass spectrometer or an electrospray Fourier transform ion cyclotron resonance mass spectrometer. A database of known molecular masses and/or known base compositions of amplification products of known bioagents may be used in conjunction with the mass spectrometer. In this case, a controller is operably connected to the mass spectrometer and to the database. The controller is configured to match the molecular masses of the amplification product with a measured or calculated molecular mass of a corresponding amplification product of a bioagent. In this system, the amplification products of known bioagents preferably have a length of about 29 to about 200 nucleobases.

In other embodiments, of the system, the nucleic acid analysis apparatus includes a nucleic acid sequencer configured to perform a sequencing method. The sequencing method may be Sanger sequencing, pyrosequencing, SOLiD™ sequencing, single molecule real time sequencing, nanosequencing, tSMS™ sequencing, single molecule sequencing by synthesis, nanopore sequencing, or other method.

In other embodiments, of the system, the nucleic acid analysis apparatus includes a DNA microarray.

DESCRIPTION OF EMBODIMENTS

Definitions

Figure 1:
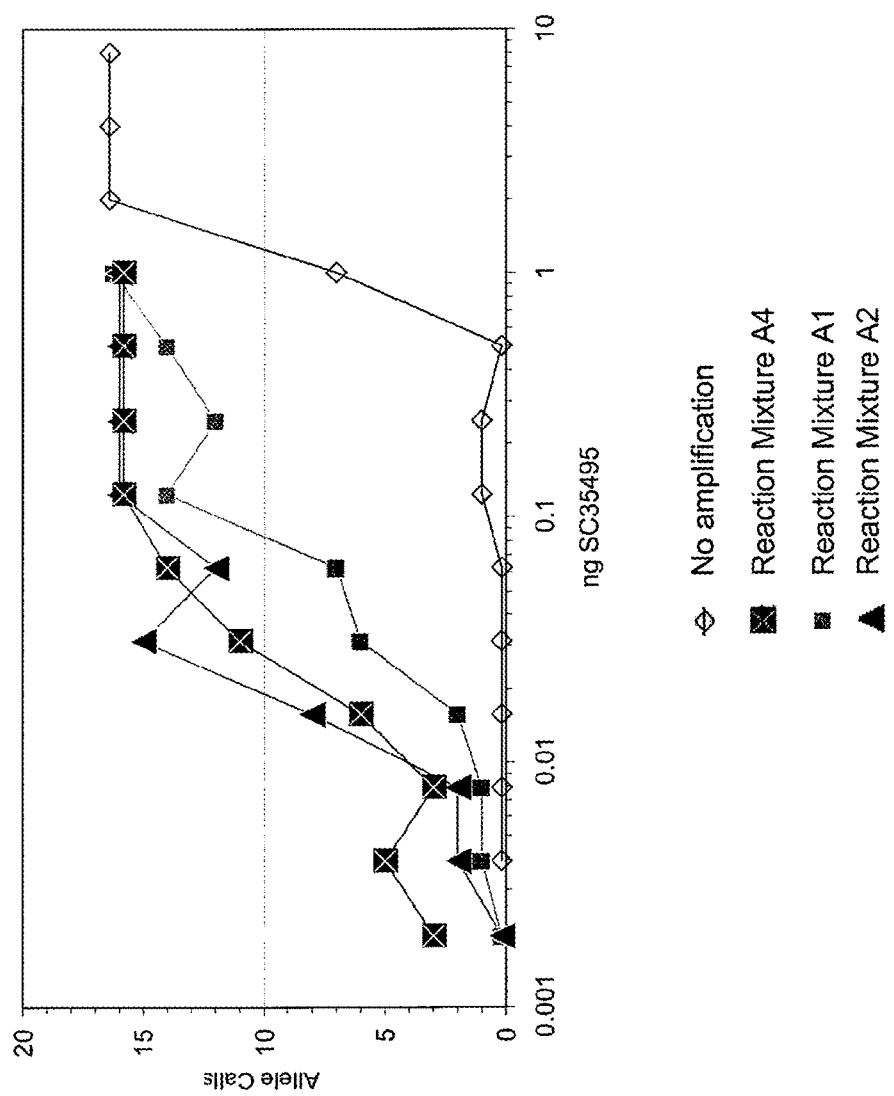
FIG. 1 is a plot of the number of allele calls made in analysis of a human DNA sample using three different amplification mixtures and a non-amplified control mixture.

To facilitate an understanding of the methods disclosed herein, a number of terms and phrases are defined below:

The term "allele" as used herein, is any one of a number of viable DNA sequences occupying a given locus (position) on a chromosome. Usually alleles are DNA (deoxyribonucleic acid) sequences that code for a gene, but sometimes the term is used to refer to a non-gene sequence. An individual's genotype for that gene is the set of alleles it happens to possess. In a diploid organism, one that has two copies of each chromosome, two alleles make up the individual's genotype.

The term "allelic balance" as used herein, refers to the ratio of the quantity of the minor allele to the quantity of the major allele.

The term "allele call" as used herein, refers to successful characterization of an allele by a given analysis method. If the analysis provides successful characterization of both alleles of a gene locus of a DNA sample, it is said that two allele calls are made. If one allele is characterized while the other allele is not characterized, it is said that one allele call is made. If neither of the two alleles is successfully characterized, no allele calls are made.

The term "amplification," as used herein, refers to a process of multiplying an original quantity of a nucleic acid template of a certain sequence in order to obtain greater quantities of nucleic acid with the same sequence.

The term "compatible solute" as used herein, refers to a class of compounds that stabilize cells and cellular components. Compatible solutes include, for example, amino acids and their derivatives, and carbohydrates.

The term "genome," as used herein, generally refers to the complete set of genetic information in the form of one or more nucleic acid sequences, including text or in silico versions thereof. A genome may include either DNA or RNA, depending upon its organism of origin. Most organisms have DNA genomes while some viruses have RNA genomes. As used herein, the term "genome" need not comprise the complete set of genetic information.

The term "hexamer" as used herein refers to a polymer composed of six units. More specifically, the term hexamer is used to describe an oligonucleotide primer having six nucleotide residues.

The term "heptamer" as used herein refers to a polymer composed of seven units. More specifically, the term heptamer is used to describe an oligonucleotide primer having seven nucleotide residues.

The term "hybridization," as used herein refers to the process of joining two complementary strands of DNA or one each of DNA and RNA to form a double-stranded molecule through Watson and Crick base-pairing or pairing of a universal nucleobase with one of the four natural nucleobases of DNA (adenine, guanine, thymine and cytosine).

The term "locked nucleic acid" (LNA), refers to a modified RNA nucleotide. The ribose moiety of a locked nucleotide is modified with an extra bridge connecting 2' and 4' carbons. The ribose structure with this bridge is a bicyclic structure. The bridge "locks" the ribose in a 3'-endo structural conformation, which is often found in the A-form of DNA or RNA. LNA nucleotides can be mixed with DNA or RNA bases in an oligonucleotide. The locked ribose conformation enhances base stacking and backbone pre-organization and has the effect of significantly increasing the thermal stability (melting temperature) of a DNA duplex. Two examples of LNAs are the classic LNA which has a single carbon (methylene) bridge between the ribose 2' and 4' carbons and another type of LNA known as ENA, which has an ethylene bridge between the ribose 2' and 4' carbons. An individual LNA nucleotide is considered to be an example of a modified nucleotide which can be incorporated into DNA and oligonucleotide primers.

The term "multiple displacement amplification" as used herein, refers to a non-PCR-based isothermal method based on the annealing of random hexamers to denatured DNA, followed by strand-displacement synthesis at constant temperature. It has been applied to small genomic DNA samples, leading to the synthesis of high molecular weight DNA with limited sequence representation bias. As DNA is synthesized by strand displacement, a gradually increasing number of priming events occur, forming a network of hyper-branched DNA structures. The reaction can be catalyzed using enzymes such as the Phi29 DNA polymerase or the large fragment of the Bst DNA polymerase.

The term "nucleic acid" as used herein, refers to a high-molecular-weight biochemical macromolecule composed of nucleotide chains that convey genetic information. The most common nucleic acids are deoxyribonucleic acid (DNA) and ribonucleic acid (RNA). The monomers that build nucleic acids are called nucleotides. Each nucleotide consists of three components: a nitrogenous heterocyclic base, either a purine or a pyrimidine (also known as a nucleobase); a pentose sugar and a phosphate. Different nucleic acid types differ in the structure of the sugar in their nucleotides; DNA contains 2-deoxyribose while RNA contains ribose.

The term "nucleobase" as used herein, refers to a nitrogenous heterocyclic base, either a purine or a pyrimidine in a nucleotide residue or within a nucleic acid. The term nucleobase is used herein to describe the length of a given oligonucleotide primer according to the number of nucleotide residues included in the oligonucleotide primer.

The term "octamer" as used herein refers to a polymer composed of eight units. More specifically, the term octamer is used herein to describe a primer having eight nucleotide residues.

The term "polymerase" as used herein, refers to an enzyme that catalyzes the process of replication of nucleic acids. More specifically, DNA polymerase catalyzes the polymerization of deoxyribonucleotides alongside a DNA strand, which the DNA polymerase "reads" and uses as a template. The newly-polymerized molecule is complementary to the template strand and identical to the template's partner strand.

The term "primer," as used herein refers to an oligonucleotide which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, composition of primer, use of the method, and the parameters used for primer design, as disclosed herein.

The term "processivity," as used herein, refers to the ability of an enzyme to repetitively continue its catalytic function without dissociating from its substrate. For example, Phi29 polymerase is a highly processive polymerase due to its tight binding of the template DNA substrate.

The term "Profiler" as used herein, is a generic term that refers to an assay used to characterize a group of genetic loci. Any group of genetic loci may be analyzed. One of the more common groups of loci generally includes a core group of about 13 STR marker loci known as the CODIS group (Combined DNA Index system). In a given Profiler assay, the STRs are characterized by a capillary electrophoresis method that detects fluorescently tagged STR amplification products. Examples of specific profiler assays include the AmpFlSTR® Profiler Plus™ assay and the AmpFlSTR® Identifiler® assay (Applied Biosystems, Foster City, Calif.), which has an additional 3 STR marker loci.

The term "quality of amplification" refers collectively to the yield (or fold amplification) of amplified nucleic acid, the specificity of amplification with respect to non-template nucleic acids, and the performance of the resulting amplified products in the Profiler assays.

The term "reaction mixture" as used herein refers to a mixture containing sufficient components to carry out an amplification reaction.

The term "representation" as used herein, refers to a measure of retaining the original characteristics of the template DNA being amplified in the multiple displacement amplification reaction. For example, if the template DNA in a sample obtained from an individual has an allelic balance of 1.5 to 1.0 at a particular genetic locus, and the amplified DNA indicates that the allelic balance is 2.0 to 1.0 at that same locus, one would conclude that the amplification reaction resulted in poor representation relative to a different amplification reaction producing an allelic balance of 1.6 to 1.0 for the same template DNA sample.

The term "sensitivity" as used herein refers to a measure of the ability of a given reaction mixture to amplify very low quantities of DNA such as, quantities in the picogram range. For example, a given reaction mixture that produces a useful quantity of a amplified DNA in an amplification reaction starting from a given quantity of template DNA is more sensitive than another given reaction mixture which cannot produce a useful quantity of DNA from the same quantity of DNA.

The term "set of oligonucleotide primers" as used herein, refers to a plurality of oligonucleotide primers whose members are not matched up in forward and reverse pairs as they generally are for a typical polymerase chain reaction. As used herein a "set of oligonucleotide primers" is a plurality of oligonucleotide primers having generally random sequences and ranging in length from about six to about eight nucleobases.

The term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)$^n$ in a genomic region) and is typically in the non-coding intron region. By examining several STR loci and counting how many repeats of a specific STR sequence there are at a given locus, it is possible to create a unique genetic profile of an individual.

The term "template nucleic acid" or "template DNA" as used herein, refers to the strand or strands of DNA that are replicated in an amplification reaction catalyzed by a polymerase enzyme. More specifically, a template nucleic acid represents the target nucleic acid added to the amplification reaction. The target nucleic acid refers to the object of analysis. A sample containing the template nucleic acid may contain other nucleic acid contaminants which would not be equally considered as template nucleic acids. For example, if the objective of analysis is to identify an individual from his or her DNA, a sample containing this DNA would be obtained and amplified. This DNA is the target of analysis and represents the template. Contaminating nucleic acids may be present but are not considered as template DNA because they are not the object of analysis.

The term "universal nucleobase" as used herein, refers to a nucleobase that is capable of forming a base pair with any of the four natural nucleobases of DNA; adenine, guanine, thymine or cytosine.

The term "whole genome amplification" or "WGA" as used herein generally refers to a method for amplification of a DNA sample in a non-specific manner, in order to generate a new sample that is indistinguishable from the original but with a higher DNA concentration. The ideal whole genome amplification technique would amplify a sample up to a level sufficient to perform multiple tests and archiving procedures, while maintaining the original sequence representation. The DNA of the sample may include an entire genome or a portion thereof. Degenerate oligonucleotide-primed PCR (DOP), primer extension PCR technique (PEP) and multiple displacement amplification (MDA), are examples of whole genome amplification methods.

Description of Embodiments

Overview

Disclosed herein are methods, reaction mixtures, kits and primer compositions and systems for multiple displacement amplification reactions appropriate for amplifying small quantities of DNA. The amplified DNA is particularly useful for carrying out human forensics testing and is also useful for clinical testing or for identification of pathogens in environmental samples. The systems described herein are conveniently adaptable for use as a nucleic acid preparation unit as a "front end" component for further nucleic acid analyses such as base composition analyses of targeted amplification products corresponding to bioagent identifying amplicons or any number of rapid "next generation" nucleic acid sequencing processes such as pyrosequencing, SOLiD™ sequencing, single molecule real time sequencing, nanosequencing, tSMS™ sequencing, single molecule sequencing by synthesis, and nanopore sequencing, or other method known to those of skill in the art.

Methods and Reaction Mixtures

The methods for multiple displacement amplification include the steps of preparing a reaction mixture that enhances the sensitivity, allelic balance and quality of the template DNA being amplified.

Sensitivity is a measure of the ability of the reaction mixture to amplify the smallest quantities of DNA.

Allelic balance refers to the ratio of the quantities of two forms of a given allele. If representation of the original DNA is maintained in a given multiple displacement amplification reaction, the allelic balance should be maintained. Poor representation of the original template DNA in the amplified product is a common problem associated with whole genome amplification methods (Dean et al. *Proc. Natl. Acad. Sci U.S.A.* 2002, 99, 5261-5266).

Quality is a general measure of the extent of amplification obtained and the percentage of the amplification products from the template (or "target") DNA. A further measure of quality is the performance of the amplification product in a DNA Profiler™ assay where specific human DNA markers are measured for the purpose of identifying human individuals.

In some embodiments, the reaction mixtures employed in the multiple displacement amplification reactions include compounds known as stabilizers or compatible solutes. These compounds stabilize cells and cellular components when exposed to extreme conditions. In bacteria, the uptake or synthesis of compatible solutes renders the cells and their enzymatic machinery more resistant to stress-inducing environmental conditions such as high osmolarity or high temperatures. These protective effects can be extended to amplification reactions by inclusion as components of an amplification reaction mixture.

The compatible solute betaine (N,N,N-trimethylglycine), is an amino acid that acts as an osmoprotectant which increases the resistance of polymerase enzymes to denaturation and also allows amplification reactions to overcome low levels of contaminants that often result in low-quality amplification reactions (Weissensteiner et al. *Biotechniques* 1996, 21, 1102-1108). The compatible solute trehalose is a non-reducing disaccharide in which two D-glucose units are linked by an alpha-alpha-1,1-glycosidic bond.

Trehalose has been identified as an enhancer of the polymerase chain reaction (PCR) acting to lower the melting temperature of DNA and increasing the thermal stability of Taq polymerase (Speiss et al. *Clin. Chem.* 2004, 50, 1256-1259).

Dimethylsulfoxide (DMSO) is another example of a stabilizer. This compound is a polar aprotic solvent that dissolves both polar and nonpolar compounds and is miscible in a wide range of organic solvents as well as water. DMSO is used in amplification reactions to inhibit secondary structures in the DNA template or the DNA primers. It is added to the reaction mixture prior to amplification and interferes with the self-complementarity of the DNA, minimizing interfering reactions. In some embodiments, DMSO is included in the amplification reaction mixture at a concentration of about 1% to about 5%, preferably about 2.5%.

In some embodiments, the compatible solutes are betaine, trehalose, or a combination thereof. In some embodiments, the concentrations of betaine included in the reaction mixtures is in a range between about 0.2 M to about 1.6 M or any fractional concentration therebetween. Preferably, the concentration of betaine is about 0.6 M.

In some embodiments, the concentration of trehalose included in the reaction mixtures is in a range between about 0.1 M to about 1.0 M and any fractional concentration in between. Preferably, the concentration of trehalose is about 0.6 M.

In some embodiments, the reaction mixtures employed for the multiple displacement amplification include one or more polymerase enzymes. In some embodiments, the catalytic activities include 5'→3' DNA polymerase activity, and optionally 3'→5' exonuclease proofreading activity, and/or DNA repair activities such as, for example, 5'→3' excision repair activity. Examples of various polymerase enzymes include, but are not limited to, the following: Phi29, Klenow fragment, T4 polymerase, T7 polymerase, BstE polymerase, E. coli Pol I, Vent, Deep Vent, Vent exo-polymerase, Deep Vent exo-, KOD HiFi, Pfu ultra, Pfu turbo, Pfu native, Pfu exo-, Pfu exo-Cx, Pfu cloned, Proofstart (Qiagen), rTth, Tgo and Tfu Qbio. Most of these polymerases are commercially available. In one exemplary embodiment, the polymerases are Phi29 and at least one more polymerase enzyme. In certain embodiments, the polymerases are Phi29 and at least one Pol I polymerase. To further illustrate, the polymerases are Phi29 and E. coli Pol I in some embodiments.

In embodiments wherein the polymerases in the reaction mixture includes Phi29 polymerase, and E. coli Polymerase I (also known as Pol I), the enzymes include 5'→3' DNA polymerase activity, 3'→5' exonuclease proofreading activity, and 5'→3' excision repair activity.

In some embodiments, Phi29 is the major polymerase while E. coli DNA Polymerase I (Pol I) is present at lower activity levels. In some embodiments, the reaction mixture contains about 0.2 units/µL to about 0.6 units/µL of Phi29 polymerase or any concentration therebetween. Preferably, the reaction mixture contains about 0.43 units/µL of Phi29 polymerase.

In some embodiments, the reaction mixture contains about 0.005 units/µL to about 0.015 units/µL of Pol I polymerase or any concentration therebetween. Preferably, the reaction mixture contains about 0.01 units/µL of Pol I polymerase.

In other embodiments, other non-polymerase enzymes or accessory proteins are included in the reaction mixtures such as, for example, helicase, gyrase, T4G32 and SSBP for example. Most of these accessory proteins are commercially available.

In some embodiments, the reaction mixture further includes pyrophosphatase which serves to convert pyrophosphate to phosphate. Pyrophosphate accumulates in the reaction mixture as a result of the amplification reaction (one equivalent of pyrophosphate is generated from each incorporated deoxynucleotide triphosphate added and is known to inhibit the amplification reaction). In some embodiments the reaction mixture contains about $3 \times 10^{-5}$ units/µL to about $1 \times 10^{-4}$ units/µL of a pyrophosphatase. Preferably, the reaction mixture contains about $7 \times 10^{-5}$ units/µL of pyrophosphatase.

In some embodiments, it is preferable that bovine serum albumin (BSA) is not included in the reaction mixture because commercially obtained lots of BSA often are contaminated with bovine DNA which represents a significant contaminant that may be co-amplified with the template DNA in the amplification reaction. Alternatively, BSA may be included if it can be successfully purified away from contaminating nucleic acids. Methods for removal or destruction of nucleic acids in protein samples such as irradiation and anion exchange chromatography are known to those skilled in the art.

In some embodiments, the amplification reaction is an isothermal amplification reaction, meaning that it is carried out at a constant temperature. In some embodiments, the reaction conditions include thermal cycling where the temperature of the reaction mixture is successively raised and lowered to pre-determined temperatures in order to melt and anneal the two strands of DNA. In some embodiments, it may be appropriate to perform an isothermal amplification if, for example, representation is maintained by amplification with Phi29 polymerase. In other embodiments, a greater contribution of enzymatic activity originating from different polymerase (such as Pol I, for example) may be advantageous, in which case thermal cycling may be included in the reaction conditions.

In some embodiments, the amplification reaction results in the amplification of template DNA consisting of a whole genome, or a substantial portion thereof.

In some embodiments, the multiple displacement amplification reaction produces an amplification product from a template DNA at a constant ratio relative to production of amplification products of other extraneous DNAs in a given sample. This preserves the representation of the original template DNA.

In some embodiments, the total quantity of the template DNA added to the reaction mixture for amplification is at least about 2 picograms.

In some embodiments the reaction mixture is prepared with a detergent which may be a non-ionic detergent such as Tween 20, Tween 40, Tween 80, Triton X-100 or Triton X-102, Span 80 or any combination thereof. The detergent may be present in the reaction mixture at a level between about 0.05% to about 3% (w/v). Preferably the non-ionic detergent is Tween 40 at a concentration of about 0.05% to about 3% (w/v), preferably at a concentration of about 1% (w/v).

Without being bound to any particular theory, it is believed that performing the amplification reactions in an emulsion format results in capture of individual template nucleic acid molecules within emulsion micro-droplets. This provides for amplification of the template nucleic acid while minimizing interference from background nucleic acid molecules. It is also thought that the emulsion format provides more efficient amplification of smaller fragments of the target genome.

The method for amplifying a nucleic acid in the form of an emulsion is carried out by contacting said nucleic acid with the reaction mixture which is in the form of an emulsion which may be prepared using a detergent and a hydrophobic polymer. A preferred hydrophobic polymer is polydimethylsiloxane which may be present in the reaction mixture in a ratio of about 4:1 of polydimethylsiloxane to aqueous solution. In other embodiments, the hydrophobic polymer is mineral oil.

In some embodiments, the reaction mixture contains other additives to improve the activity of one or more of the polymerases. Magnesium chloride is one such additive which enhances polymerase activity. Magnesium chloride may be included in the reaction mixture at a concentration between about 2 mM to about 20 mM, preferably about 9 mM.

Ammonium sulfate may be added to improve the solubility of proteins (polymerases, pyrophosphatase and BSA) in the reaction mixture. The concentration of ammonium sulfate is advantageously between about 2 mM and about 15 mM, preferably about 7.5 mM.

Dithiothreitol may also be added to the reaction mixture to maintain reducing conditions and prevent cross-linking of proteins. The concentration of dithiothreitol is advantageously between about 1 mM and about 8 mM, preferably about 4 mM.

The pH of the reaction mixture may be maintained by known buffering agents such as Tris and other buffer agents known to those skilled in the art. Advantageously, the pH of the reaction mixture is maintained between about 7.1 and 7.8, preferably about 7.5.

Primer Sets

The primer sets used in the amplification reactions disclosed herein are generally defined as a plurality of oligonucleotide primers. In some embodiments, the primers have random sequences that hybridize randomly to the template nucleic acid at positions of the template that substantially base-pair with the primers. The members of the primer sets may be random hexamers (primers with six nucleotide residues), random heptamers (primers with seven nucleotide residues), or random octomers (primers with eight nucleotide residues). The syntheses of such hexamers, heptamers and octomers with random sequences are accomplished by known procedures.

In some embodiments, the primers include modifications that increase their affinity for the template nucleic acid. In certain embodiments, the modifications include substituents on the ribose ring of a given nucleotide residue of a given primer, which stabilize or lock the ribose ring in the 3'-endo conformation which provides for a higher affinity of the nucleotide residue for a pairing nucleotide residue on a template nucleic acid.

The conformation of the ribose sugar of a nucleotide residue containing a pentofurnosyl sugar within a primer is influenced by various factors including substitution at the 2'-, 3'- or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag). Modification of the 2' position to favor the 3'-endo conformation can be achieved while maintaining the 2'-OH as a recognition element (Gallo et al. *Tetrahedron* 2001, 57, 5707-5713; Harry-O'kuru et al., *J. Org. Chem.*, 1997, 62, 1754-1759; and Tang et al., *J. Org. Chem.* 1999, 64, 747-754). Alternatively, preference for the 3'-endo conformation can be achieved by deletion of the 2'-OH as exemplified by 2'-deoxy-2'-F-nucleosides (Kawasaki et al., *J. Med. Chem.* 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., *Bioorg. Medicinal Chem. Lett.* 1995, 5, 1455-1460 and Owen et al., J. Org. Chem. 1976, 41, 3010-3017), or for example modification to yield methanocarba nucleoside analogs (Jacobson et al., *J. Med. Chem. Lett.* 2000, 43, 2196-2203 and Lee et al., *Bioorg. Med. Chem. Lett.* 2001, 11, 1333-1337) also induce preference for the 3'-endo conformation.

The most common locked nucleic acid modification is a 2' to 4' methylene bridge which locks the ribose ring in the 3'-endo conformation. This modification is often abbreviated as "LNA," meaning "locked nucleic acid. Another type of locked nucleic acid is referred to as ENA (ethylene-bridged nucleic acid). This modification includes a 2' to 4' ethylene bridge. The synthesis and preparation of the 2' to 4' bridged monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). The 2' to 4' bridged monomers and methods of preparing them are also described in WO 98/39352 and WO 99/14226. The first analogs of 2' to 4' bridged nucleic acids, phosphorothioate-LNA and 2'-thio-LNAs, have also been prepared as published (Kumar et al., *Bioorg. Med. Chem. Lett.*, 1998, 8, 2219-2222). Preparation of oligodeoxyribonucleotide duplexes with 2' to 4' bridged nucleoside analogs as substrates for nucleic acid polymerases has also been described (WO 99/14226). Furthermore, the synthesis of 2'-amino-LNA, a novel conformationally-restricted high-affinity oligonucleotide analog with a handle has been described in the art (Singh et al., *J. Org. Chem.* 1998, 63, 10035-10039). In addition, 2'-amino- and 2'-methylamino-LNAs have been prepared and the thermal stability of their duplexes with complementary RNA and DNA strands has been previously reported (see, e.g., WO/2005/044976).

In some embodiments, at least some of the primers contain at least one 2' to 4' bridged nucleotide residues or at least two 2' to 4' bridged nucleotide residues. In other embodiments, 2' to 4' bridged nucleotide residues are located at the $2^{nd}$ and $5^{th}$ positions of the oligonucleotide primers. These embodiments of the primer sets are hexamers, heptamers or octamers or any combination thereof.

In some embodiments, the primers have random sequences with the exception of having specifically located universal nucleobases such as inosine. The specific locations of the inosine nucleobases are preferably at the two final terminal nucleobases of a given inosine-containing primer.

In some embodiments, one or more phosphorothioate linkages are incorporated into the primers at the 3' end of a given primer for the purpose of making the primer more resistant to nuclease activity.

Primer Kits

Some embodiments also provide kits comprising the primers disclosed herein.

In some embodiments, the kits comprise a sufficient quantity of a polymerase enzyme having high processivity. In some embodiments, the high processivity polymerase is Phi29 polymerase or Taq polymerase. In other embodiments, the high processivity polymerase is a genetically engineered polymerase whose processivity is increased relative to the native polymerase from which it was constructed.

In some embodiments, the kits comprise a sufficient quantity of an additional polymerase in addition to a high processivity polymerase, for improvement of the characteristics of the amplification reaction. In some embodiments, the additional polymerase is *E. coli* Pol I polymerase.

In some embodiments, the kits comprise a sufficient quantity of pyrophosphatase which catalyzes conversion of pyrophosphate to two equivalents of phosphate. Pyrophosphate is known to inhibit polymerase reactions.

In some embodiments, the kits further comprise deoxynucleotide triphosphates, buffers, and buffer additives such as compatible solutes including trehalose and betaine at concentrations optimized for multiple displacement amplification.

The kit may include components for preparation of emulsion PCR reaction mixtures. Such emulsion-forming components may include a detergent or the combination of a detergent and a hydrophobic polymer.

In some embodiments, the detergent provided with the kit is a non-ionic detergent. The non-ionic detergent may be Tween 20, Tween 40, Tween 80, Triton X-100 or Triton X-102, or any combination thereof. The detergent may be present in the reaction mixture at a level between about 0.05% to about 3.0% (w/v). A preferred hydrophobic polymer for inclusion in the kit is polydimethylsiloxane. This polymer is included in the kit in an amount sufficient to prepare reaction mixtures having a ratio of about 4:1 of polydimethylsiloxane to aqueous solution. Other hydrophobic polymers may be provided in the kit, such as mineral oil for example.

The kits may also contain a buffered solution containing any components of the reaction mixtures described above, as long as they are chemically stable under convenient shipping and storage conditions. Components may also be provided individually in separate containers in the kit in solutions, or lyophilized powders with instructions for preparation of solutions for dispensing into reaction mixtures.

In some embodiments, the kits further comprise instructions for carrying out multiple displacement amplification reactions.

Nucleic Acid Amplification Systems

A system for analyzing nucleic acids is also provided. The system includes a thermal cycler. The thermal cycler (also known as a thermocycler, PCR Machine or nucleic acid Amplifier) is a laboratory apparatus that rapidly cycles between temperatures and is commonly used to amplify nucleic acids. The device typically has a thermal block with holes where tubes holding the PCR reaction mixtures can be inserted. The cycler then raises and lowers the temperature of the block in discrete, pre-programmed steps. The flexibility provided by the programmable thermal cycler makes it readily adaptable to multiple displacement amplification reactions.

The system further includes a container for holding a reaction mixture for a multiple displacement amplification reaction. The container is configured for insertion into the thermal cycler and is compatible with one or more detergents or hydrophobic solvents which are used for developing an emulsion in the reaction mixture. The container may be a tube, or a 96- or -384 well microtiter plate formed of polystyrene, polypropylene, or polycarbonate, or any other polymer compatible with the detergents or hydrophobic solvents used for development of the emulsion. Microfluidics cards or chips constructed of compatible materials may also be used provided they are configured for functional placement in the thermal cycler.

The system also includes one or more liquid handlers configured to deliver a nucleic acid sample to the container and to deliver an emulsion-breaking compound to the container.

The system may be combined with a downstream nucleic acid analysis apparatus such that the system described above functions as a nucleic acid preparation unit in order to raise the level of the nucleic acid of interest so that it can then be analyzed in whole, or in part by the downstream apparatus. The downstream nucleic acid analysis apparatus may include a second thermal cycler configured to perform a targeted second amplification of amplified nucleic acid produced by the system. A purification unit such as a magnetic system including an anion exchange resin linked to a magnetic bead is useful for purifying a product of the targeted second amplification may also be included. Such purification units are described in US Patent Application Publication Nos. 20050164215 and 20050130196 which are incorporated herein by reference in entirety. A nucleic acid analysis unit for determining the base composition of the targeted second amplification product using mass spectrometry and a molecular mass/base composition database may be used to analyze the nucleic acids. Particular embodiments of the mass-spectrum based detection methods are described in the following patents, patent applications and scientific publications, all of which are herein incorporated by reference as if fully set forth herein: U.S. Pat. Nos. 7,108,974; 7,217,510; 7,226,739; 7,255,992; 7,312,036; 7,339,051; US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; 2007/0264661; 2008/0160512; 2008/0311558; 2009/0004643; 2009/0047665; 2009/0125245; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; WO2007/100397; WO2007/118222; WO2008/104002; WO2008/116182; WO2008/118809; WO2008/127839; WO2008/143627; WO2008/151023; WO2009/017902; WO2009/023358; WO2009/038840; Ecker et al., Ibis T5000: a universal biosensor approach for microbiology. *Nat Rev Microbiol.* 2008 Jun. 3; Ecker et al., The Microbial Rosetta Stone Database: A compilation of global and emerging infectious microorganisms and bioterrorist threat agents. *BMC Microbiology.* 2005. 5(1): 19; Ecker et al., The Ibis T5000 Universal Biosensor: An Automated Platform for Pathogen Identification and Strain Typing. *JALA.* 2006. 6(11): 341-351; Ecker et al., The Microbial Rosetta Stone Database: A common structure for microbial biosecurity threat agents. *J. Forensic Sci.* 2005. 50(6): 1380-5; Ecker et al., Identification of *Acinetobacter* species and genotyping of *Acinetobacter baumannii* by multilocus PCR and mass spectrometry. *J Clin Microbiol.* 2006 August; 44(8):2921-32; Ecker et al., Rapid identification and strain-typing of respiratory pathogens for epidemic surveillance. *Proc Natl Acad Sci USA.* 2005 May 31; 102(22):8012-7. Epub 2005 May 23; Wortmann et al., Genotypic evolution of *Acinetobacter baumannii* strains in an outbreak associated with war trauma. *Infect Control Hosp Epidemiol.* 2008 June; 29(6):553-555; Hannis et al., High-resolution genotyping of *Campylobacter* species by use of PCR and high-throughput mass spectrometry. *J Clin Microbiol.* 2008 April; 46(4):1220-5; Blyn et al., Rapid detection and molecular serotyping of adenovirus by use of PCR followed by electrospray ionization mass spectrometry. *J Clin Microbiol.* 2008 February; 46(2):644-51; Eshoo et al., Direct broad-range detection of alphaviruses in mosquito extracts. *Virology.* 2007 Nov. 25; 368(2):286-95; Sampath et al., Global surveillance of emerging Influenza virus genotypes by mass spectrometry. *PLoS ONE.* 2007 May 30; 2(5):e489; Sampath et al., Rapid identification of emerging infectious agents using PCR and electrospray ionization mass spectrometry. *Ann N Y Acad Sci.* 2007 April; 1102: 109-20; Hujer et al., Analysis of antibiotic resistance genes in multidrug-resistant *Acinetobacter* sp. isolates from military and civilian patients treated at the Walter Reed Army Medical Center. *Antimicrob Agents Chemother.* 2006 December; 50(12):4114-23; Hall et al., Base composition analysis of human mitochondrial DNA using electrospray ionization mass spectrometry: a novel tool for the identification and differentiation of humans. *Anal Biochem.* 2005 Sep. 1; 344(1):53-69; Sampath et al., Rapid identification of emerging pathogens: coronavirus. *Emerg Infect Dis.* 2005 March; 11(3):373-9; Jiang Y, Hofstadler S A. A highly efficient and automated method of purifying and desalting PCR products for analysis by electrospray ionization mass spectrometry. *Anal Biochem.* 2003. 316: 50-57; Jiang et al., Mitochondrial DNA mutation detection by electrospray mass spectrometry. *Clin Chem.* 2006. 53(2): 195-203. Epub December 7; Russell et al., Transmission dynamics and prospective environmental sampling of adenovirus in a military recruit setting. *J Infect Dis.* 2006. 194(7): 877-85. Epub 2006 Aug. 25; Hofstadler et al., Detection of microbial agents using broad-range PCR with detection by mass spectrometry: The TIGER concept. Chapter in *Encyclopedia of Rapid Microbiological Methods.* 2006; Hofstadler et al., Selective ion filtering by digital thresholding: A method to unwind complex ESI-mass spectra and eliminate signals from low molecular weight chemical noise. *Anal Chem.* 2006. 78(2): 372-378; Hofstadler et al., TIGER: The Universal Biosensor. *Int J Mass Spectrom.* 2005. 242(1): 23-41; Van Ert et al., Mass spectrometry provides accurate characterization of two genetic marker types in *Bacillus anthracis*. *Biotechniques.* 2004. 37(4): 642-4, 646, 648; Sampath et al., Forum on Microbial Threats: Learning from SARS: Preparing for the Next Disease Outbreak—Workshop Summary. (ed. Knobler S E, Mahmoud A, Lemon S.) The National Academies Press, Washington, D.C. 2004. 181-185.

As an alternative to the mass spectrometry/base composition analysis system, sequencing of the product of the multiple displacement amplification reaction or a targeted second amplification product thereof may be performed using a sequencer configured for a sequencing method selected from the group consisting of Sanger sequencing, pyrosequencing, SOLiD™ sequencing, single molecule real time sequencing, nanosequencing, tSMS™ sequencing, single molecule sequencing by synthesis, nanopore sequencing, or other technique. These methods are generally known to those skilled in the art and are described in U.S. Pat. Nos. 7,211,390; 7,211,414; 7,329,492; 7,482,120; 7,282,337; 7,220,549; 7,351,532; 7,232,656; 7,115,400; 6,833,246; 6,787,308 which are incorporated herein by reference in entirety.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1: Effects of Compatible Solutes on Sensitivity of Amplification Reaction The purpose of this series of experiments was to investigate the effects of the compatible solutes trehalose and betaine on enhancement of the sensitivity of the amplification reaction where sensitivity reflects the ability to successfully amplify the target DNA at low concentrations below the 1 nanogram level.

Initial investigations indicated that the concentration of trehalose that provides an optimal increase in sensitivity of the amplification reaction was approximately 0.8 M, as indicated in an amplification reaction of 50 picograms of human DNA, followed by a calculation of the percentage of alleles detected in analysis of the amplified DNA obtained in the reaction. Likewise, the optimal concentration of betaine was found to be approximately 0.8 M.

In order to investigate the effects of compatible solutes on the sensitivity of the amplification reaction, amplification reaction mixtures were developed as indicated in Table 1.

TABLE 1

| Amplification Mixtures | |
|---|---|
| | Final Conc. |
| Mixture 1 | |
| Template DNA 5 µl from dilution to extinction described below. | Variable |
| Tris HCl | 0.04025M |
| Tris Base | 0.00975M |
| Magnesium Chloride | 0.012M |
| Ammonium Sulfate | 0.01M |
| dNTP mix 100 mM (25 mM each) | 2 mM each |
| DTT | 0.004M |
| Primer Pair Mix | 0.05 mM |
| Diluted enzyme in buffer | 0.5 units/µl |
| Mixture 2 (0.8M Trehalose) | |
| Template DNA 5 µl from dilution to extinction described below | Variable |
| Tris HCl | 0.04025M |
| Tris Base | 0.00975M |
| Magnesium Chloride | 0.012M |
| Ammonium Sulfate | 0.01M |
| Trehalose | 0.6M |
| dNTP mix 100 mM (25 mM each) | 2 mM each |
| DTT | 0.004M |
| Primer Pair Mix | 0.05 mM |
| Diluted enzyme in buffer | 0.5 units/µl |
| Mixture 3 (0.8M Trehalose + 0.8M Betaine) | |
| Template DNA 5 µl from dilution to extinction described below. | Variable |
| Tris HCl | 0.04025M |
| Tris Base | 0.00975M |
| Magnesium Chloride | 0.012M |
| Ammonium Sulfate | 0.01M |
| Betaine | 0.6M |
| Trehalose | 0.6M |
| dNTP mix 100 mM (25 mM each) | 2 mM each |
| DTT | 0.004M |
| Primer Pair Mix | 0.05 mM |
| Diluted enzyme in buffer | 0.5 units/µl |

| MixA8/MixB5 | |
|---|---|
| Tris Ph 7.5 | 50.00 mM |
| MgCl2 | 9.00 mM |
| (NH4)2SO4 | 7.50 mM |
| Betaine | 0.60M |
| Sonicated Poly Adenylic acid | 1.00 Ng/ul |
| Trehalose | 0.60M |
| DNTP mix 100 mM (25 mM each) | 2.00 mM |
| DTT | 4.00 mM |
| Primers | 15.00 uM |
| Phi 29 | 0.43 u/ul |
| Pol1 | 0.01 u/ul |
| Pyrophos-phosphatase | 0.00007 u/ul |
| BSA | 0.23 ug/ul |
| DMSO | 2.50% |
| Tween-40 | 1.00% |

FIG. 1 shows the results of a "dilution to extinction" experiment wherein 1 nanogram of human DNA sample SC35495 was successively diluted and added to the reaction mixtures shown in Table 1 for amplification prior to analysis of alleles by known methods. The amplification reactions were carried out as follows: the reaction mixtures of Table 1 (1, 2 and 3) were prepared and subjected to the following amplification conditions over a period of 6 hours in a thermocycler:

1) 30° C. for 4 minutes;
2) 15° C. for 15 seconds;
3) repeat steps 1 and 2 for a total of 150 times;
4) 90° C. for 3 minutes; and
5) hold at 4° C.

The resulting amplified DNA was analyzed for identification of alleles using a mass spectrometry-based analysis method wherein specific primer pairs are then used to obtain additional specific amplification products via PCR of loci. These specific amplification products have lengths up to about 140 nucleobases which are appropriate for base composition analysis by mass spectrometry in a manner similar to that disclosed in Jiang et al. (*Clin Chem.* 2007, 53, 195-203). FIG. 1 clearly shows that reaction mixtures 2 and 3 produce amplified DNA from which allele calls can be made at concentration levels as low as 2 picograms.

In another experiment, the resulting amplified DNA was analyzed using the Profiler™ fluorescence procedure, for determination of a series of short tandem repeat (STR) alleles known as the CODIS (Combined DNA Index System) group. Specific primer pairs were then used to obtain additional specific amplification products via PCR of the loci of interest. These amplification products were then subjected to the Profiler fluorescence procedure. In Tables 2 and 3, ten of the thirteen CODIS core STR (short tandem repeat) loci are included (abbreviations for the loci column labels are as follows: D3S=D3S1358; D8S=D8S1179; D21S=D21S11; D18S=18S51; D5S=D5S8181; D13S=D13S317; and D7S=D7S820, while vWA indicates the von Willebrand factor gene; TPOX indicates the thyroid peroxidase gene; FGA indicates the fibrinogen alpha-chain gene; and AMEL indicates the amelogenin gene). The leftmost column indicates the quantity of DNA used in the amplification reactions. The numbers appearing under the loci indicate the number of allele calls made in the analysis according to the Profiler™ method. The objective is to make two allele calls for as many loci as possible at the lowest possible quantity of DNA prior to amplification because the ability to do so would provide the ability to obtain useful forensic DNA samples from small quantities of tissues.

TABLE 2

Sensitivity of Reaction Mixture 1

| Quantity of DNA(pg) | D3S | vWA | FGA | AMEL | D8S | D21S | D18S | D5S | D13(H) | D7S |
|---|---|---|---|---|---|---|---|---|---|---|
| 1000 | 2 | 2 | 2 | 2 | 2 | 2 | 2 | 2 | 2 | 2 |
| 500 | 2 | 2 | 2 | 2 | 2 | 2 | 2 | 2 | 2 | 2 |
| 250 | 2 | 1 | 2 | 1 | 1 | 2 | 1 | 2 | 2 | 2 |
| 125 | 1 | 2 | 2 | 2 | 2 | 2 | 1 | 2 | 2 | 1 |
| 63 | 0 | 1 | 0 | 1 | 0 | 0 | 1 | 0 | 0 | 0 |
| 31 | 1 | 1 | 2 | 1 | 0 | 2 | 0 | 0 | 0 | 1 |
| 16 | 0 | 0 | 0 | 0 | 0 | 0 | 0 | 2 | 0 | 0 |
| 8 | 0 | 0 | 2 | 0 | 0 | 0 | 0 | 0 | 2 | 0 |
| 4 | 0 | 0 | 0 | 0 | 0 | 0 | 1 | 1 | 0 | 0 |
| 2 | 0 | 0 | 0 | 0 | 0 | 0 | 0 | 1 | 0 | 0 |

TABLE 3

Sensitivity of Reaction Mixture 3

| Quantity of DNA(pg) | D3S | vWA | FGA | AMEL | D8S | D21S | D18S | D5S | D13(H) | D7S |
|---|---|---|---|---|---|---|---|---|---|---|
| 1000 | 2 | 2 | 2 | 2 | 2 | 2 | 2 | 2 | 2 | 2 |
| 500 | 2 | 2 | 2 | 2 | 2 | 2 | 2 | 2 | 2 | 2 |
| 250 | 2 | 2 | 2 | 2 | 2 | 2 | 2 | 2 | 2 | 2 |
| 125 | 2 | 2 | 2 | 2 | 2 | 2 | 2 | 2 | 2 | 2 |
| 63 | 2 | 2 | 2 | 2 | 1 | 1 | 1 | 2 | 2 | 2 |
| 31 | 2 | 2 | 1 | 2 | 1 | 2 | 2 | 1 | 2 | 2 |
| 16 | 2 | 0 | 2 | 1 | 1 | 1 | 1 | 1 | 0 | 0 |
| 8 | 2 | 2 | 0 | 0 | 0 | 0 | 1 | 0 | 0 | 0 |
| 4 | 2 | 0 | 0 | 0 | 1 | 0 | 0 | 1 | 0 | 1 |
| 2 | 1 | 0 | 1 | 0 | 1 | 0 | 0 | 0 | 0 | 0 |

Tables 2 and 3 clearly indicate that mixture 3 comprising added solutes substantially improves sensitivity over that achieved using non-solute mixture 1. Mixture 3, therefore, generates more product from trace nucleic acid samples as low as 2 picograms and provides 5 or more allele calls for trace samples as low as 4 picograms.

Example 2: Effects of Compatible Solutes on Maintaining Allelic Balance in the Amplification Reaction Allelic balance is a measure that indicates the ratio of quantity of detection of the minor allele vs. the major allele. It is desirable to maintain the allelic balance of a given sample of DNA as it is amplified in order to provide an accurate representation of the allelic balance in the original sample.

Figure 2:
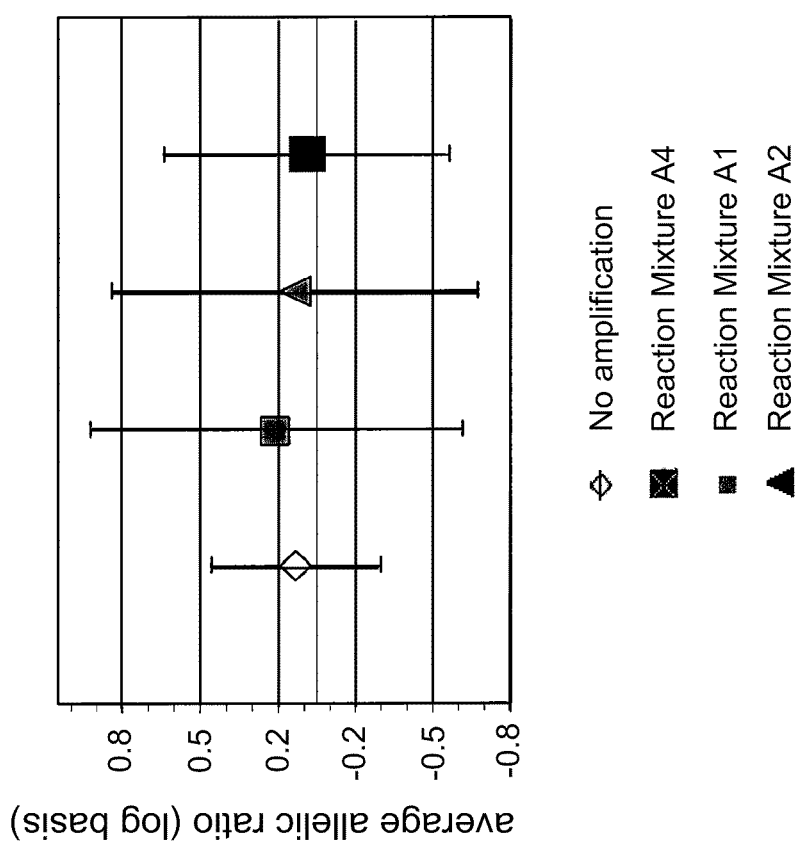
FIG. 2 is a plot of the average allelic ratio (log base 2) for allele calls made in analysis of a human DNA sample using three different amplification mixtures and a non-amplified control mixture.

A human DNA sample designated SC35495 was amplified according to conditions described in Example 1. In this example, the amounts of the alleles detected were quantified using the commercially available kit Quantifiler™ (Applied Biosystems). The quantity values were converted to $Log_2$ to provide a more intuitive measure of balance. These values are shown in FIG. 2, where it can be seen that mixture 3 (A4) is the best mixture for maintaining the best representation of the allelic balance. This indicates that inclusion of compatible solutes betaine and trehalose to the reaction mixture improves allelic balance/representation over the amplification reaction over the reaction mixtures without solute or with trehalose alone.

Example 3: Effects of Compatible Solutes on Maintaining the Quality of the Amplification Reaction The quality of the amplification reaction can be described in terms of providing a combined measure of optimal fold amplification, a high percentage of amplification of the target nucleic acid being analyzed, and optimal performance in the Profiler™ assay.

Figure 3:
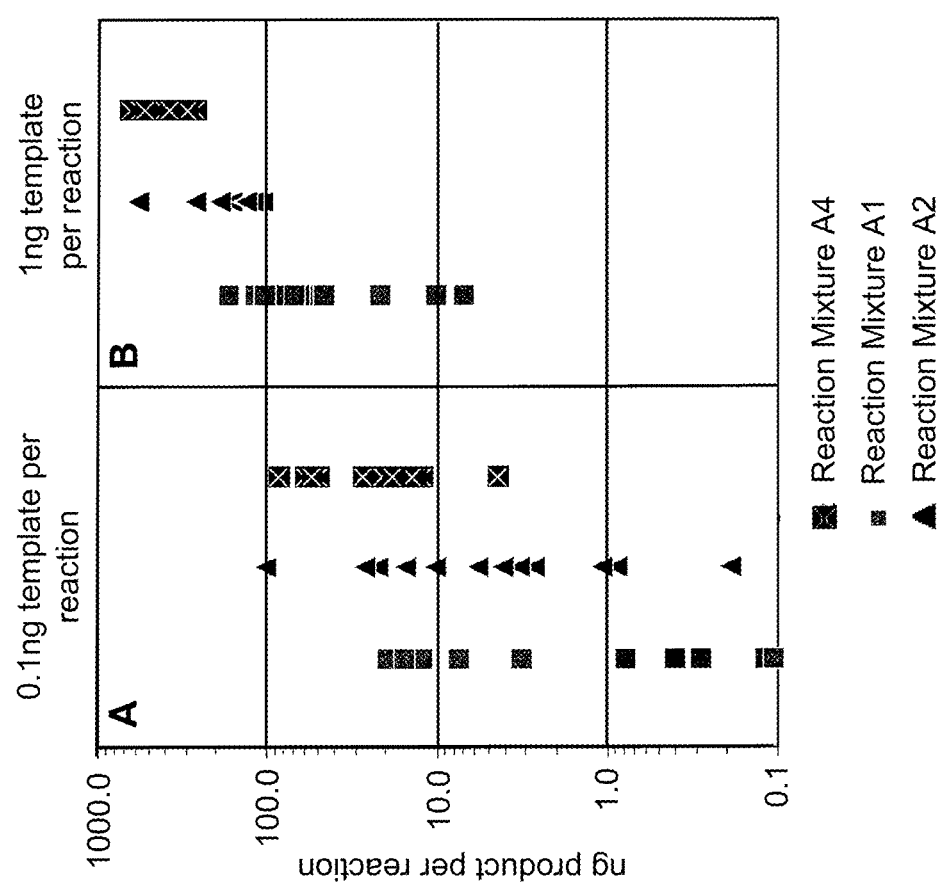
FIGS. 3A and 3B are plots indicating the quantity of amplification product obtained using three different amplification mixtures.

Shown in FIG. 3 are the results of the determinations of quantity of template DNA amplified by the three reaction mixtures according to the conditions described in Example 1 using 0.1 nanograms of template DNA (panel A) and 1 nanogram of template DNA (panel B). It is clear that mixture 3 (A4) produces the most amplified DNA. Furthermore, it was found that mixture 3 (A4) produces fewer extraneous non-template peaks detected in the Quantifier™ assay (not shown) and in 1% agarose gels (not shown) than observed for the other two mixtures. Thus, the inclusion of betaine and trehalose in the reaction mixture significantly improves the quality of an amplification reaction over that of mixtures having no solutes or having trehalose alone.

Example 4: Effects of Inclusion of an Additional DNA Polymerase on the Amplification Reaction To assess the effect of augmenting the action of Phi29 polymerase, additional polymerase enzymes were individually added to amplification mixture 3 along with 15 picograms of human sample SC35495 template DNA. The samples were amplified as indicated in Example 1. The resulting amplified DNA was analyzed in the Profiler™ assay and allele calls were made and tallied. Table 4 shows the results and indicates that the addition of Pol I polymerase results in an average of four additional allele calls in the experiment and also indicates that addition of Pol I polymerase is a favorable modification of the amplification mixture.

TABLE 4

Effects of an Additional Polymerase Enzyme on Whole Genome Amplification as Measured by Allele Calls from Amplified Mixtures.

| Additional Enzyme Included in Mixture | Allele Calls Experiment 1 | Allele Calls Experiment 2 | Average Allele Calls |
|---|---|---|---|
| None | 13 | 12 | 12.5 |
| Klenow Fragment | 11 | 7 | 9 |
| T4 polymerase | 11 | 9 | 10 |
| T7 polymerase | 14 | 13 | 13.5 |
| BstE polymerase | 14 | 9 | 11.5 |
| Pol I polymerase | 18 | 15 | 16.5 |

The addition of Pol I polymerase further increases the yield of amplified DNA and also enhances the genotyping of trace amounts of DNA. Addition of a further enzyme, pyrophosphatase is useful because accumulation of pyrophosphate during the amplification process is known to inhibit polymerase reactions.

Example 5: Design and Testing of Individual Oligonucleotide Primer Modifications A series of primer motifs were designed for improvement of the quality, sensitivity and balance of the amplification reaction. The modifications included inclusion of inosine nucleobases at specific positions within the hexamer, heptamer and octomer primers. Phosphorothioate modified linkages were incorporated into these primers at the two 3'-most terminal linkages. The most effective placement of inosine nucleobases was found to be at the fifth and sixth positions of the hexamer primers, sixth and seventh positions of the heptamer primers and seventh and eighth positions of the octomer primers. These primers containing inosine nucleobases produced less amplified product than the corresponding primers that did not contain inosine. However, the total amplified product was found to represent a greater proportion of the template DNA, indicating that inclusion of inosines in the primers improves the quality of amplification.

The position of the LNA modified nucleotide residues of the heptamer primers was examined in detail by systematically changing the position of one or two LNA modifications (L) in random heptamers as indicated in Table 5. The symbols in Table 5 are as follows: N=A, T, C or G; I=inosine; NI=nitroindole; L=LNA (locked versions of A, C, T or G). In this experiment, improvements in fold amplification are achieved for primers having LNA substituted in position 2, position 4, position 5, positions 1 and 4, and positions 2 and 5. LNA substitutions were well tolerated at all positions, with only the most 3' position showing a slight negative effect (LNA-7). Primers bearing LNA substituted residues at two positions have a higher fold amplification increase as compared to those having only a single LNA substituted residue. Moreover, substituting inosine residues at the most 3' positions of a position 2, position 5 LNA substituted primer further improved fold amplification (LNA-11 and LNA-12). In some embodiments, NLNNLIN or 7 mer N with a phosphorothiote between nucleotide positions 6 and 7 are used.

TABLE 5

Determination of Optimal Positioning of LNA residues in the Primers

| Primer | 5' Primer Nucleotide Residue Position 3' | | | | | | | Fold Amplification Relative to Control |
|---|---|---|---|---|---|---|---|---|
| | 1 | 2 | 3 | 4 | 5 | 6 | 7 | |
| Control | N | N | N | N | N | N | N | 1 |
| LNA-1 | L | N | N | N | N | N | N | 0.9 |
| LNA-2 | N | L | N | N | N | N | N | 1 |
| LNA-3 | N | N | L | N | N | N | N | 0.9 |
| LNA-4 | N | N | N | L | N | N | N | 1.1 |
| LNA-5 | N | N | N | N | L | N | N | 1.4 |
| LNA-6 | N | N | N | N | N | L | N | 1 |
| LNA-7 | N | N | N | N | N | N | L | 0.7 |
| LNA-8 | L | N | N | L | N | N | N | 7.6 |
| LNA-9 | L | N | N | L | N | N | L | 0.2 |
| LNA-10 | L | N | N | L | N | I | I | 4.8 |
| LNA-11 | N | L | N | N | L | I | I | 9.3 |
| LNA-12 | N | L | N | N | L | N | N | 4.1 |
| LNA-13 | L | N | N | L | N | NI | I | None |

Example 6: Preliminary Investigation of Detergents on the Yield Obtained in Multiple Displacement Amplification Reactions The development of an emulsion formulation for a multiple displacement amplification reaction necessitates investigation of the effects of the presence of detergents and oils on the formation of the emulsion and to ascertain that these components do not have detrimental effects on reaction yields. Multiple displacement amplification reactions were carried out using 10 pg of a standard *Klebsiella pneumoniae* genome in a 50 µL reaction volume using a standardized set of primers, 2 mM of dNTPs, 3.7 units per reaction of Pol I polymerase and 18.3 units per reaction of Phi29 polymerase. Varying concentrations of different detergents were included in the reactions. One trial was conducted using polydimethylsiloxane with no detergent. The yields of the reactions were determined using quantitative PCR (QPCR). The results are shown in Table 6.

TABLE 6

Yields of Multiple Displacement Amplification Reaction Mixtures Containing Detergents and Polydimethylsiloxane

| Emulsion Component Added | Amount | Yield Concentration (ng/µL) |
|---|---|---|
| Polydimethylsiloxane | 80 µL | 15.3 |
| Tween 20 | 0.1% | 99.8 |
| Tween 40 | 0.1% | 113.0 |
| Tween 80 | 0.1% | 64.7 |
| Triton-X 100 | 0.1% | 95.4 |
| Triton-X 102 | 0.1% | 112.4 |
| Tween 20 | 0.05% | 74.8 |
| Tween 40 | 0.05% | 59.8 |
| Tween 80 | 0.05% | 64.3 |
| Triton-X 100 | 0.05% | 62.4 |
| Triton-X 102 | 0.05% | 67.2 |

The addition of polydimethylsiloxane was found to decrease the total yield with 5 to 10 seconds of shaking. Addition of 0.05% of the detergents did not appreciably affect the yield but concentrations of 0.1% increased the yield for each detergent except for Tween 80.

A second similar experiment was conducted with detergent concentrations ranging between 0.1% and 1.0%. The results are included in Table 7.

TABLE 7

Yields of Multiple Displacement Amplification Reaction Mixtures Containing Detergents

| Emulsion Component Added | Concentration | Yield Concentration (µg/µL) |
|---|---|---|
| Tween 20 | 0.1% | 57.9 |
| Tween 40 | 0.1% | 54.6 |
| Triton-X 100 | 0.1% | 47.2 |
| Triton-X 102 | 0.1% | 48.4 |
| Tween 20 | 0.5% | 61.9 |
| Tween 40 | 0.5% | 78.7 |
| Triton-X 100 | 0.5% | 52.0 |
| Triton-X 102 | 0.5% | 63.0 |
| Tween 20 | 1.0% | 65.3 |
| Tween 40 | 1.0% | 60.5 |
| Triton-X 100 | 1.0% | 44.1 |
| Triton-X 102 | 1.0% | 45.7 |

In these experiments, Tween 40 was identified as the best performing reagent.

Figure 4:
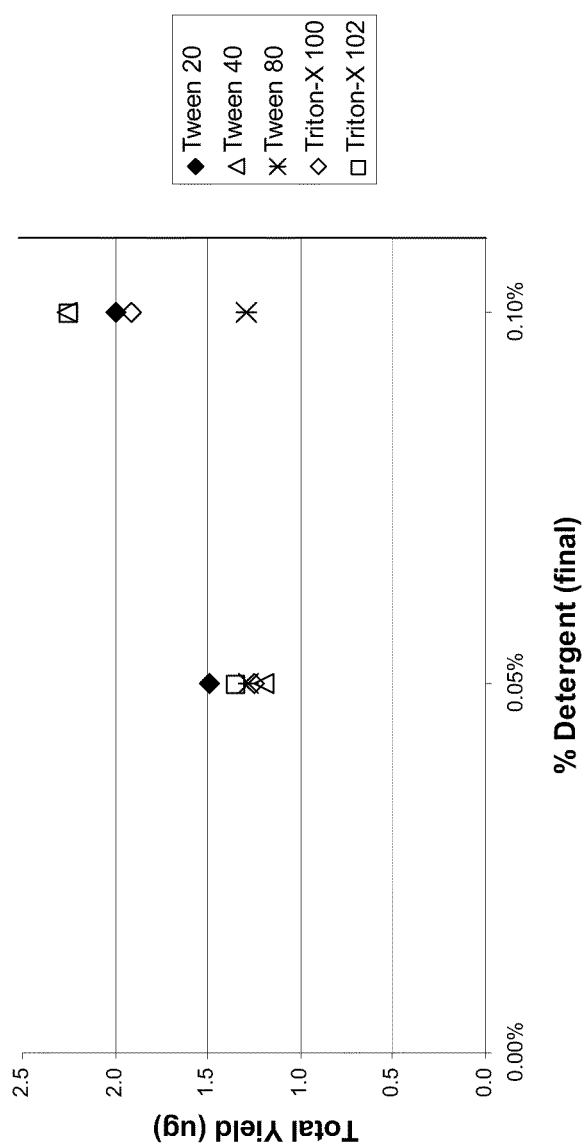
FIG. 4 is a plot of total yield of amplification product obtained with detergents in the amplification mixture (0.05% to 0.1%).
Figure 5:
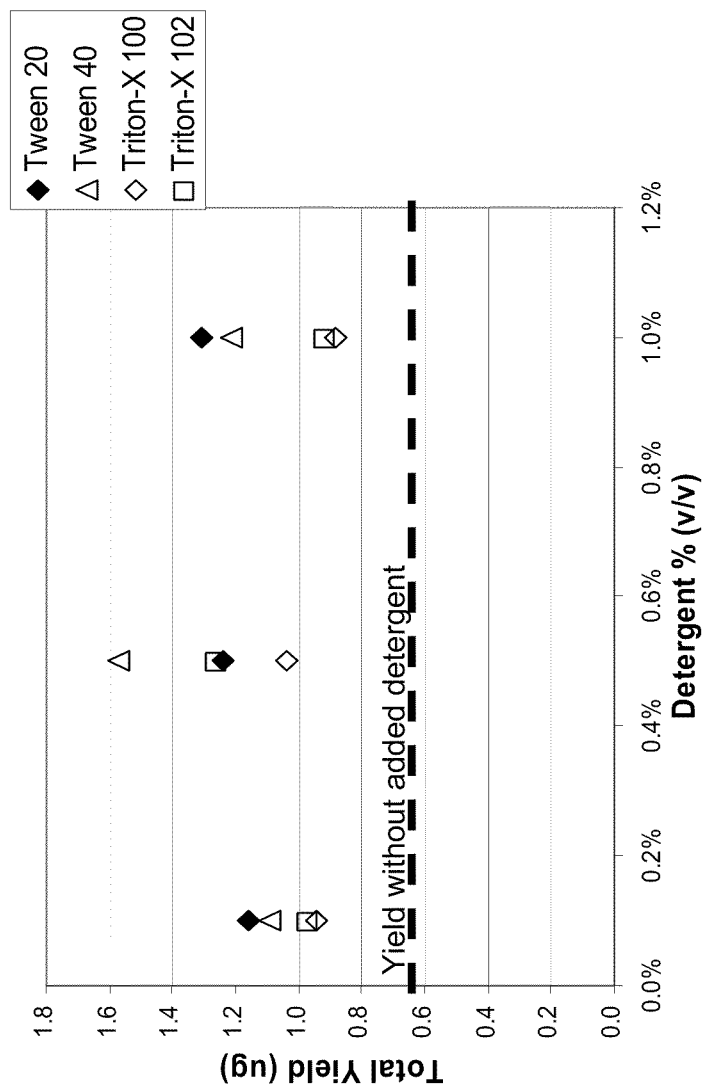
FIG. 5 is a plot of total yield of amplification product obtained with detergents in the amplification mixture (0.1% to 1.0%).

Example 7: Effect of Detergents on Balance in Multiple Displacement Amplification Reactions The effects of Tween 20, Tween 40, Tween 80 (Sigma Catalogue #P9416-50ML, P1504-500ML, P5188-50ML, respectively), Triton X-100 and Triton X-102 (Sigma Cat #T8787-50ML, X102-500ML) were investigated with respect to the amplification of test DNA samples. Upon completion of the amplification reaction, the emulsion was broken by addition of an excess amount of chloroform. The amplification yields were evaluated in the presence of detergents between 0.05% and 1% (w/v). Results are presented in FIGS. 4 and 5. Tween 40 was identified as having the most favorable effect on the yield.

Figure 6:
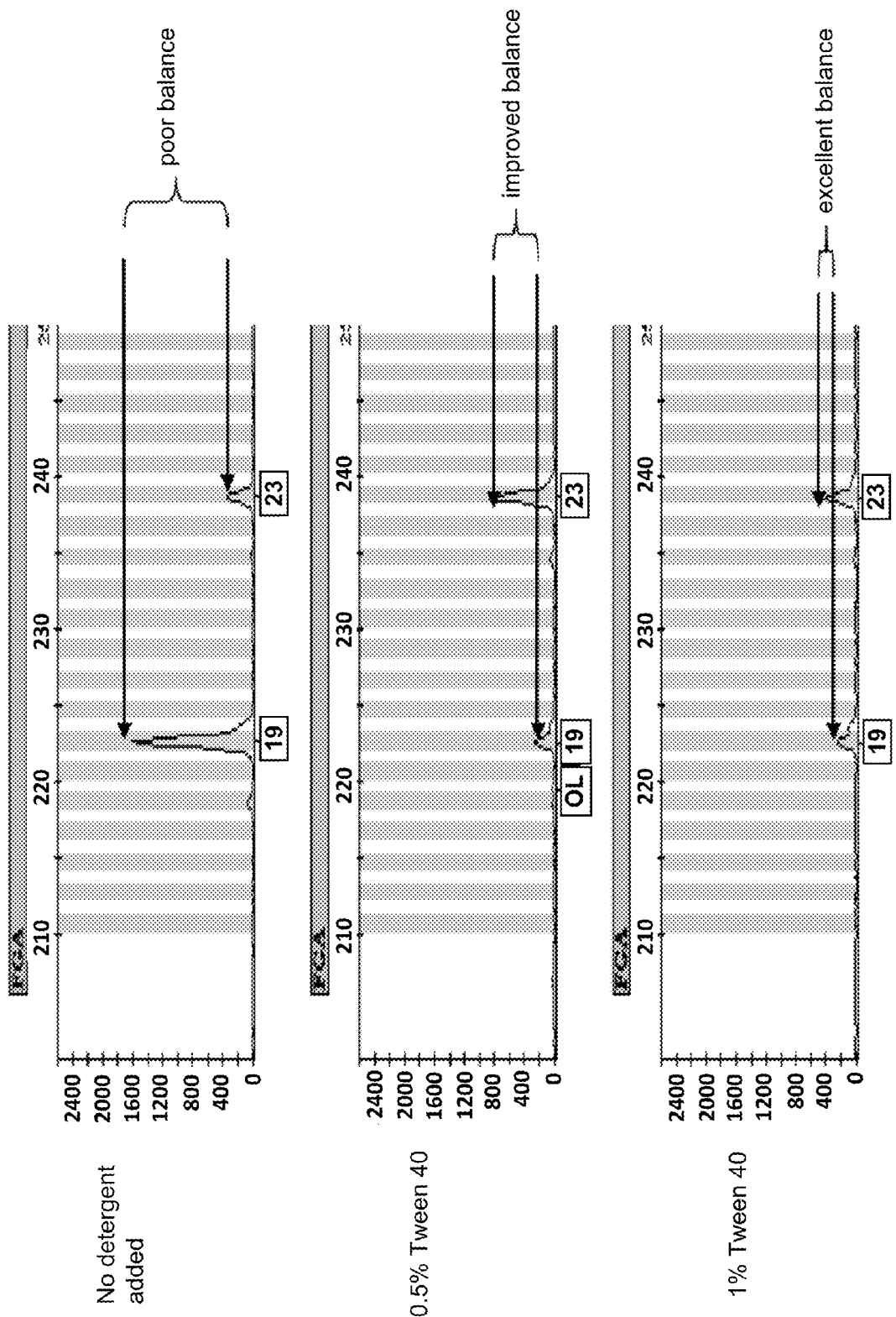
FIG. 6 shows the assay results for the FGA locus in the Identifiler® assay indicating the effect of Tween 40 on the allelic balance.

The amplified DNA obtained as described above in the presence and absence of Tween 40 was used as the template DNA for an assay using the AmpFlSTR® Identifiler® PCR Amplification Kit according to the manufacturer's instructions (Applied Biosciences, Foster City, Calif.). The results obtained for analysis of the FGA locus using DNA amplified from a multiple displacement amplification reaction in the absence of detergent and in the presence of 0.5% and 1% Tween 40 are shown in FIG. 6. It is clear that the balance between the two alleles of the locus (19 and 23) is vastly improved in the presence of 1% Tween 40.

The improved balance of allele detection also resulted in fewer instances of non-detected alleles ("drop-outs") in the analysis. Table 8 shows the relationship between allele drop-outs and the presence of Tween 40 in the reaction mixture.

TABLE 8

Effect of Tween 40 in initial Amplification Mixture on Allele Drop-Outs in the Identifiler® Assay

| Concentration of Tween 40 (% w/v) | Allele Calls | Drop Outs |
|---|---|---|
| 0.0 | 20 | 11 |
| 0.5 | 24 | 7 |
| 1.0 | 25 | 6 |

Example 8: Multiple Displacement Amplification Reactions in Water-in-Oil Emulsions Without being bound to any particular theory, it is believed that performing the amplification reactions in solutions containing a detergent in an emulsion format results in capture of individual template nucleic acid molecules within emulsion micro-droplets. This provides for amplification of the template nucleic acid while minimizing interference from background nucleic acid molecules and competition between individual DNA template molecules. It is also thought that the emulsion format provides more efficient amplification of smaller or low copy number fragments of the target genome.

Aqueous solutions with 0.5-1% detergent (Tween 20, 40, 80; Triton-X 100, 102) mixed with a 4-fold excess volume of polydimethylsiloxane in a bead beater (Biospec Products Inc., Bartlesville, Okla.) for 15 seconds were found to form emulsions which were stable over the chosen amplification cycle described in Example 6. This indicates that the Tween 40/polydimethylsiloxane emulsion is compatible with the multiple displacement amplification reaction.

Multiple displacement amplification reactions in polydimethylsiloxane-based emulsions containing 0.5% Tween 40 and 1% Triton X-100 were found to produce significant amplification products as evidenced by electrophoresis gels (not shown).

Amplified DNA samples obtained from the polydimethylsiloxane emulsions containing 0.5% and 1% Tween 40 were analyzed with the Identifiler® assay to determine if the allele drop-outs could be reduced. This is a particularly desirable outcome because, in the case of the Identifiler® assay, it is unlikely that an individual could be identified in a forensic investigation if an incomplete allelic profile is obtained from the assay due to drop outs resulting from poor representation and/or balance in an initial multiple displacement amplification reaction.

The results shown in Table 9 indicate that a concentration of Tween 40 of 1% (w/v) in a polydimethylsiloxane emulsion provides good representation and balance in multiple displacement amplification reactions. In the case of 1% Tween 40, drop outs were completely eliminated. The Tween 40/polydimethylsiloxane emulsion therefore represents a very useful improvement for multiple displacement amplification. The skilled person will recognize that although the representation and balance were assessed using a commercially available human STR assay kit, DNA obtained using the multiple displacement amplification reactions described herein will also be useful for other applications such as, for example, identification of viruses or bacteria from samples containing trace amounts of the DNA of the viruses or bacteria.

TABLE 9

Effect of Tween 40 in initial Emulsion Amplification Mixture on Allele Drop-Outs in the Identifiler ® Assay

| Concentration of Tween 40 (% w/v) | Allele Calls | Drop Outs |
| --- | --- | --- |
| 0.0 | 20 | 11 |
| 0.5 | 28 | 3 |
| 1.0 | 31 | 0 |

The preceding examples illustrate that the use of polymerases, inclusion of compatible solutes, detergents and hydrophobic polymers and modifications of primers individually and collectively improve the sensitivity of amplification while preserving representation of the original nucleic acid sample and producing high quality amplification products.

Example 9: Testing of the Effects of DMSO Concentration and Denature Time Period on Allelic Balance To test the effect of DMSO concentration and denature time period on the allelic balance of multiple displacement amplification, three 62.5 pg samples of DNA (SC3) were amplified using a standard protocol designated WGA_4 which includes a 10 minute denature cycle. A fourth 62.5 pg DNA sample was subjected to the same protocol with the exception that a 3 minute denature time period was used with a temperature of 95° C. One amplification reaction conducted using WGA_4 contained DMSO at a concentration of 5% and another contained 10% DMSO. The amplified DNA was then analyzed using the Identifiler™ assay and the allelic balance was determined for each sample. The results of this experiment are shown in Table 10.

TABLE 10

Effects of DMSO Concentration and Denature Time Period on Allelic Balance in Amplified Samples

| Sample | Denature Time Period (minutes) | DMSO Concentration (%) | Allelic Balance |
| --- | --- | --- | --- |
| 1 | 10 | 0 | 1.90 |
| 2 | 10 | 5 | 1.44 |
| 3 | 10 | 10 | 1.77 |
| 4 | 3 | 0 | 2.55 |

The data shown in Table 10 indicates that a 10 minute time period for denaturation of the DNA sample and a DMSO concentration of 5% in the multiple displacement amplification reaction produce an allelic balance of 1.44. In some embodiments, a one minute denaturation time at 95° C. is utilized.

Example 10: Further Testing of the Effects of DMSO Concentration and Denature Time Period on Allelic Balance The experiment described in Example 9 was further refined with additional denaturation time periods between zero and 10 minutes and with DMSO concentrations ranging between 1 and 5% using a standardized multiple displacement amplification protocol designated WGA_1. This protocol includes the step of addition of 400 μL of polydimethylsiloxane and shaking the reaction mixture for two 30 seconds pulses to produce an emulsion. Upon completion of the multiple displacement amplification reaction, the emulsion was broken by addition of 250 μL of chloroform, vortexing and centrifuging. The allelic balance of the reaction products was analyzed using the Identifiler™ assay.

TABLE 11

Further Investigation of the Effects of DMSO Concentration and Denature Time Period on Allelic Balance in Amplified Samples

| Sample | Denature Time Period (minutes) | DMSO Concentration (%) | Allelic Balance |
| --- | --- | --- | --- |
| 1 | 0 | 0 | 2.06 |
| 2 | 1 | 0 | 1.37 |
| 3 | 3 | 0 | 1.93 |
| 4 | 5 | 0 | 1.60 |
| 5 | 10 | 0 | 2.23 |

TABLE 11-continued

Further Investigation of the Effects of DMSO Concentration and
Denature Time Period on Allelic Balance in Amplified Samples

| Sample | Denature Time Period (minutes) | DMSO Concentration (%) | Allelic Balance |
|---|---|---|---|
| 6 | 3 | 1 | 1.67 |
| 7 | 3 | 2.5 | 1.23 |
| 8 | 3 | 5 | 1.33 |

The data shown in Table 11 indicates that a 3 minute time period for denaturation of the DNA sample and a DMSO concentration of 2.5% in the multiple displacement amplification reaction produce the best allelic balance of 1.23.

Example 11: Dilution to Extinction Experiment: Amplification of Diluted DNA Samples by Multiple Displacement Amplification with 2.5% DMSO This experiment tests the ability of the multiple displacement amplification reaction conditions to produce amplification product with good allelic balance and yield. DNA samples diluted from 500 pg to 7.8 pg were amplified in reaction mixtures containing 2.5% DMSO. The results indicating amplification yield and balance are shown in Table 10.

TABLE 12

Effect of Starting DNA Sample Concentration
on Yield and Allelic Balance

| Starting Amount of DNA (pg) | Average fold Amplification | Average Drop Out | Average Allelic Balance |
|---|---|---|---|
| 500 | $2.69 \times 10^3$ | 0 | 0.56 |
| 250 | $4.90 \times 10^3$ | 0 | 0.78 |
| 125 | $8.46 \times 10^3$ | 0 | 1.01 |
| 62.5 | $1.60 \times 10^4$ | 0.67 | 1.67 |
| 31.3 | $2.39 \times 10^4$ | 4.33 | 4.74 |
| 16.6 | $4.05 \times 10^4$ | 11.00 | 8.14 |
| 7.8 | $6.99 \times 10^4$ | 13.67 | 8.73 |

The results shown in Table 12 indicate that the multiple displacement amplification method produces satisfactory average fold amplification and allelic balance down to starting amounts of DNA of 125 pg.

Figure 7:
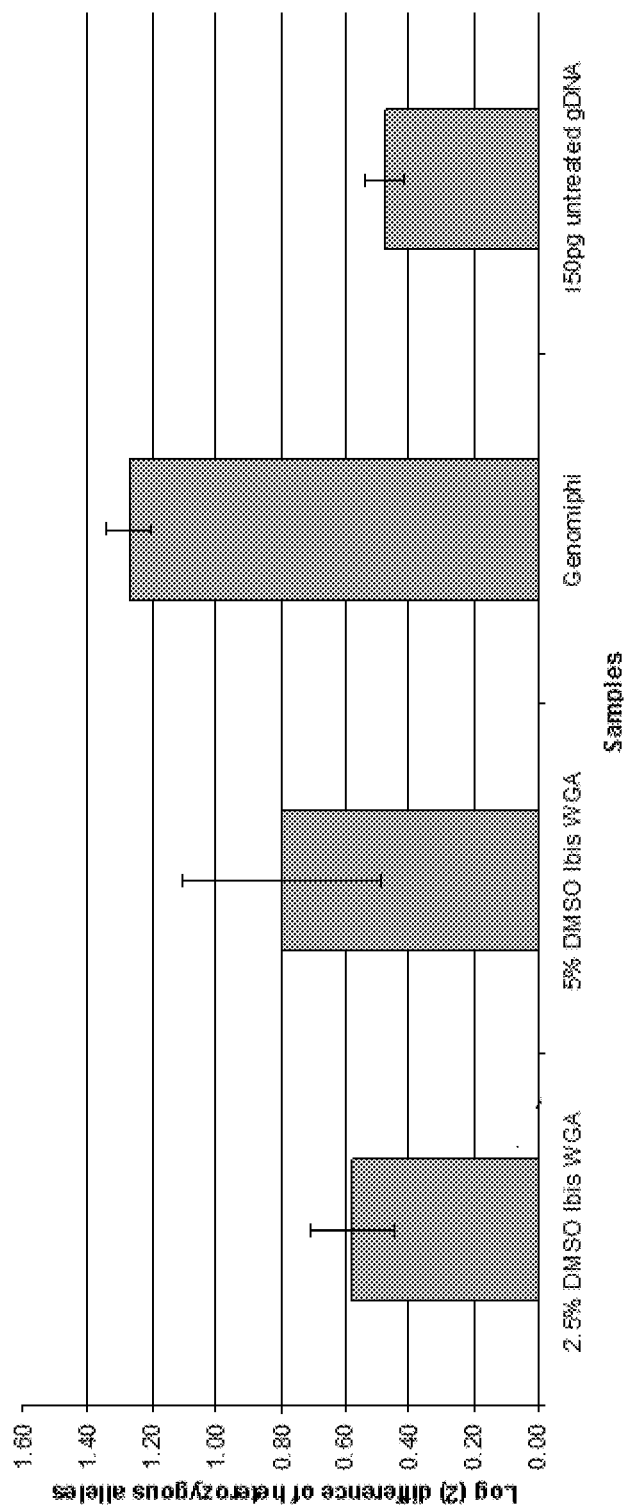
FIG. 7 shows the results of an analysis of the allelic balance obtained by amplification of a 150 pg DNA sample using emulsion multiple displacement amplification with DMSO in comparison with whole genome amplification performed using a commercial kit and in comparison with analysis of the allelic balance of an unamplified DNA sample.

Example 12: Comparison of Allelic Balance of Emulsion Amplification Including DMSO with a Commercially Available Whole Genome Amplification Kit The allelic balance obtained from emulsion multiple displacement amplification reactions of 150 pg of DNA including 2.5% and 5% DMSO was compared with the allelic balance of the same 150 pg sample of DNA amplified using Genomiphi™, a commercially available whole genome amplification kit. The results are shown in Table 13 and in FIG. 7. In Table 13, under the "Conditions" column, A, B and C represent three trials with identical reaction conditions. The bar graph of FIG. 7 shows data corresponding to the average of the three trials.

TABLE 13

Results of Comparison of DMSO-Containing Emulsion
Amplification Reaction with Genomiphi Reaction

| Sample | Conditions | DMSO Conc. (%) | Fold Amplification | Drop Outs | Average Balance |
|---|---|---|---|---|---|
| 1 | eWGA A | 2.5 | $1.31 \times 10^4$ | 0 | 0.64 |
| 2 | eWGA B | 2.5 | $1.40 \times 10^4$ | 0 | 0.67 |
| 3 | eWGA C | 2.5 | $1.26 \times 10^4$ | 0 | 0.43 |
| 4 | eWGA A | 5.0 | $8.84 \times 10^3$ | 0 | 1.16 |
| 5 | eWGA B | 5.0 | $9.33 \times 10^3$ | 0 | 0.65 |
| 6 | eWGA C | 5.0 | $7.41 \times 10^3$ | 0 | 0.59 |
| 7 | Genomiphi A | 0 | $6.58 \times 10^3$ | 0 | 1.28 |
| 8 | Genomiphi B | 0 | $6.31 \times 10^3$ | 3 | 1.21 |
| 9 | Genomiphi C | 0 | $6.55 \times 10^3$ | 0 | 1.34 |
| 10 | Neat A | 0 | — | 1 | 0.51 |
| 11 | Neat B | 0 | — | 4 | 0.52 |
| 12 | Neat C | 0 | — | 0 | 0.40 |

The results shown in Table 13 and in FIG. 7 indicate that the emulsion amplification method conducted with 2.5% DMSO produces allelic balance which is similar to that of the unamplified DNA sample and which is a much better allelic balance than that obtained using the commercially available Genomiphi™ kit.

Figure 8:
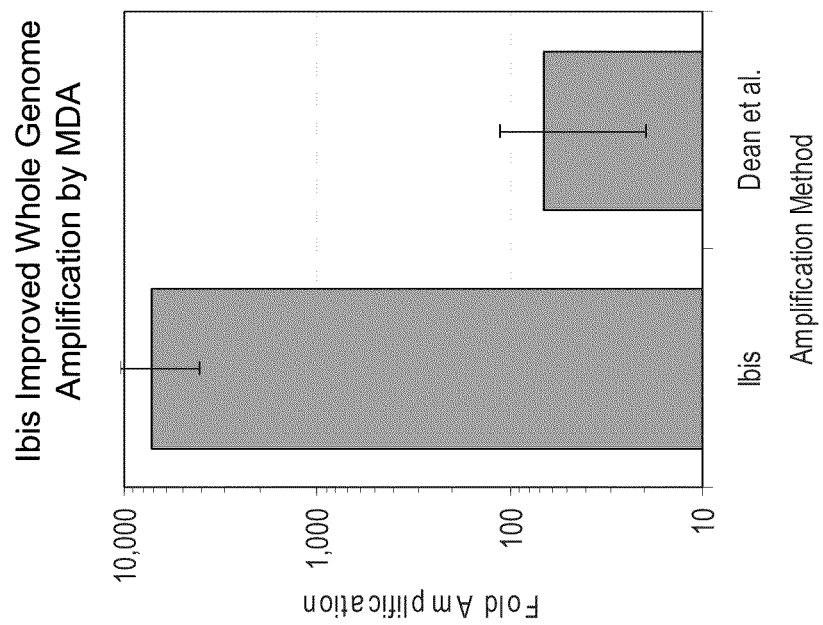
FIG. 8 is a graph showing a comparison of fold amplification data obtained from a human DNA sample obtained with an emulsion-based amplification process as described herein.

Example 13: Testing of Emulsion-Based Multiple Displacement Amplification Reaction with Human DNA Human genomic DNA was amplified in a reaction mixture containing 50 mM Tris pH 7.5, 9 mM magnesium chloride, 7.5 mM ammonium sulfate, 0.6 M betaine, 1.00 ng/µL sonicated polyadenylic acid, 0.6 M Trehalose, 2 mM of Bioline dNTPs, 4 mM dithiothreitol, 15 mM of primers, 0.43 units/µL of Phi29 polymerase, 0.01 units/µL of Pol I polymerase, $7 \times 10^{-5}$ units/µL of pyrophosphatase, 0.23 ug/µL of bovine serum albumin, 2.50% DMSO and 1.00% Tween 40. These conditions have been found to produce a synergistic effect in improving the yield of amplification as shown in FIG. 8 where it is indicated that the emulsion-based multiple displacement amplification reaction produces about a 100 fold increase in product yield relative to the procedure published by Dean et al (Dean et al. Proc. Natl. Acad. Sci. 99(8):5261-5266).

Figure 9:
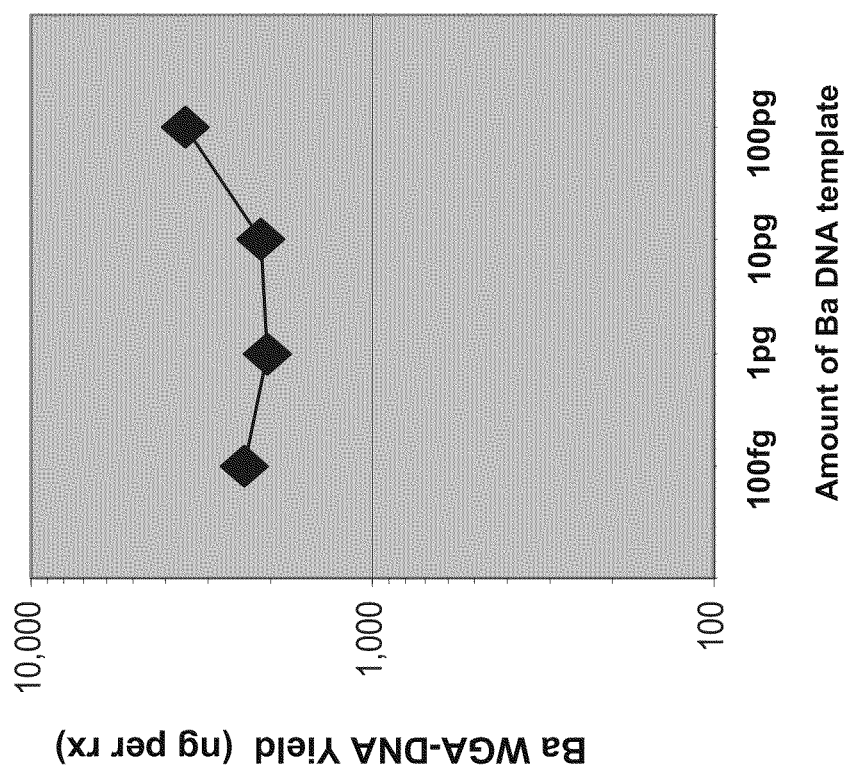
FIG. 9 is a graph showing the relationship between the yield of amplification product obtained at different DNA concentrations of a sample of *Bacillus anthracia* DNA.
Figure 10:
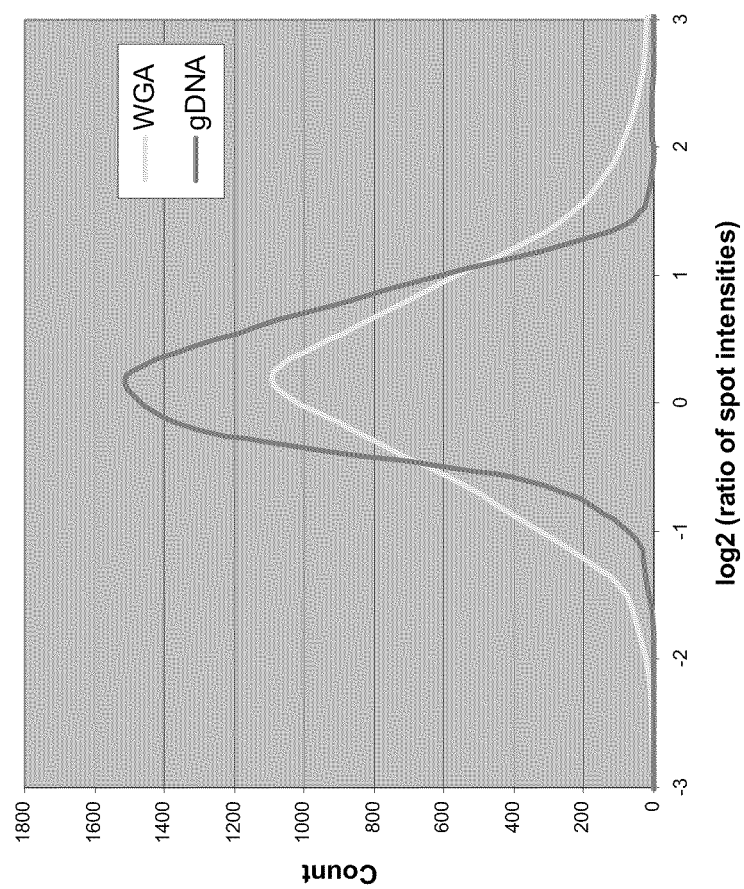
FIG. 10 is a plot of microarray counts vs log 2 ratio of spot intensities for the emulsion-based multiple displacement amplification reaction product in comparison with an unamplified control sample.
Figure 11:
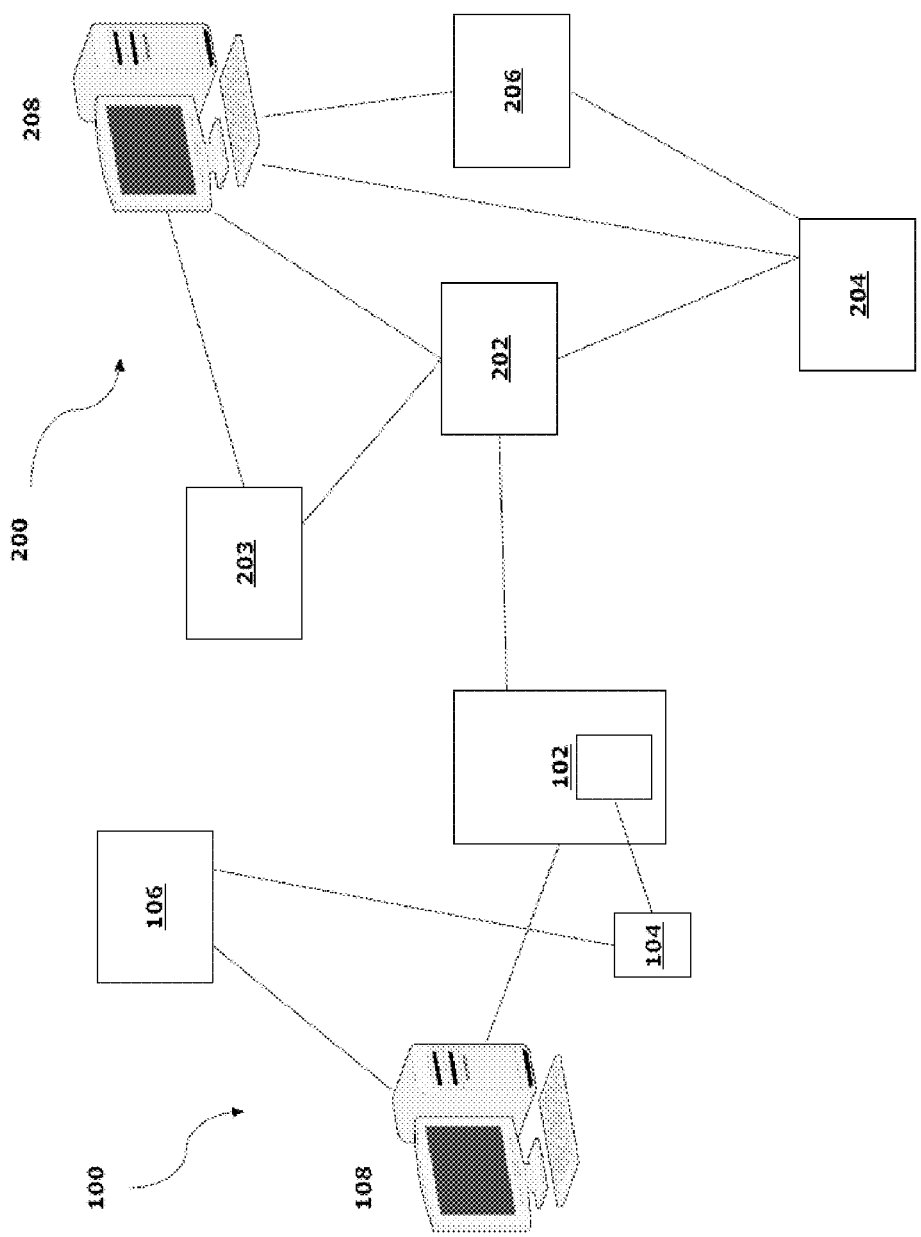
FIG. 11 is a schematic representation of an emulsion-based multiple displacement amplification reaction system combined with a downstream nucleic acid analysis apparatus.

Example 14: Yields of Emulsion-Based Multiple Displacement Amplification Reaction of Bacterial DNA Samples of four different starting amounts of *Bacillus anthracia* DNA ranging between 100 fg and 100 pg were amplified in 120 µL reaction volumes using the emulsion-based multiple displacement amplification reaction described in Example 13. The products were quantified using quantitative PCR. The yields obtained from the reaction are displayed in FIG. 9. At the lowest amount of starting DNA template (100 fg), a $2.3 \times 10^7$-fold amplification was obtained. These results indicate that the emulsion-based multiple displacement amplification reaction produces good amplification yields from low level samples of nucleic acids.

Example 15: DNA Profiling from Computer Keyboards

A Whatman Grade 50 filter disk was wetted with reaction buffer and used to swab a key from a computer keyboard. Nucleic acid was extracted using standard methods and the resulting nucleic acid sample was subjected to the emulsion-based multiple displacement amplification reaction described in Example 13. The amplified sample was analyzed using the ABI Identifiler STR assay. The human loci analyzed included: D8S1179, D21S11, D7S820, CSF1PO, D3S1358, THO1, D13S317, D16S539, D2S1338, D19S433, vWA, TPDX, D18S51, AMEL, D5S818 and FGA. The alleles identified matched the truth data in each case with the exception of the FGA locus where allele 22 was not identified. This example highlights the utility of using the emulsion-based multiple displacement amplification reaction as a pre-treatment step for genetic analysis of trace amounts of DNA.

Example 16: Microarray Analysis of Emulsion-Based Multiple Displacement Amplification Reaction of Bacterial DNA

*Bacillus anthracia* sterne strain DNA subjected to the emulsion-based multiple displacement amplification reaction under conditions described in Example 13 was analyzed using a microarray to determine spot intensities followed by comparison with a control consisting of the same genomic DNA without amplification. The results are shown in FIG. 10 where it is indicated that the profile of the plot of microarray counts vs log 2 ratio of spot intensities for the emulsion-based multiple displacement amplification reaction product is similar to the control plot. These results indicate that the emulsion-based multiple displacement amplification reaction has not appreciably altered the representation of the original sample.

Example 17: Preparation and Analysis of a Sample of DNA from an Unculturable Bacterium A new methanotropic bacterium is discovered. Despite the best efforts of microbiologists, the organism is found to be unculturable, yet it is the subject of intense interest as a possible bioremediation agent. A genetic analysis is desirable but only a few cells can be typically isolated. A total of 8 cells are isolated using flow cytometry and nucleic acids are isolated therefrom using known methods. The nucleic acid sample is then subjected to the emulsion-based multiple displacement amplification reaction under conditions described in Example 13 which produces greater than $1\times10^4$ fold amplification of the DNA in the nucleic acid sample. The sample is then purified from the extraneous components using known methods and is now in a form suitable for genetic characterization using rapid sequencing techniques or base composition analysis by mass spectrometry. The emulsion-based multiple displacement amplification reaction therefore circumvents the problems associated with having only a low level of desired nucleic acid for analysis.

Example 18: Operation of an Emulsion-Based Multiple Displacement Amplification Reaction System with a Downstream Nucleic Acid Analysis Apparatus This example describes the operation of an emulsion-based amplification system in combination with an apparatus for determination of base compositions of targeted amplification products. This combination system is shown schematically in FIG. 11. The emulsion-based amplification system 100 is configured for a multiple displacement amplification reaction and includes a thermal cycler 102 for programming of different temperatures to denature the nucleic acid and to enhance the Phi29 polymerase-driven multiple displacement amplification reaction. The reaction is conducted in a container 104 which may be an individual well of a 96-well or 384-well microtiter plate or a microfluidics chip for example. The container is configured to be compatible with the thermal cycler 102 and to fit therewithin for temperature control of the container. A liquid handler 106 is provided and configured to transfer nucleic acid samples to and from the container and also configured to deliver an emulsion-breaking compound to the container. The thermal cycler 102 and the liquid handler 106 may be under the control of a computer 108. The liquid handler 106 may also be configured under control of the computer 108 to prepare the final emulsion-based multiple displacement amplification reaction mixture from a starting "kit-type" composition comprised of compatible solutes, stabilizers and other components by adding certain reaction components to the composition just prior to initiation of the reaction.

The downstream nucleic acid analysis apparatus 200 may consist of a second thermal cycler 202 configured for a conventional PCR amplification reaction using one or more primer pairs which target conserved regions of the nucleic acid amplified in the emulsion-based amplification reaction, thereby producing a targeted second amplification product. Manipulations of liquids in the downstream apparatus 200 are handled using a second liquid handler 203. The downstream apparatus 200 may also include a purification unit consisting of a magnetic separator 204 to be used in conjunction with magnetic particles conjugated to an anion exchange resin. The magnetic separator 204 purifies the amplification product away from the reagents used in the targeted amplification process. The downstream apparatus also includes a mass spectrometer 206 for measuring the molecular mass of the targeted second amplification product according to methods described above. Advantageously a second computer 208 controls the manipulation of the components in the downstream apparatus and includes a base composition database for deconvoluting molecular mass measurements of amplification products into base compositions and for identifying matches between base compositions of amplification products and base compositions contained in a base composition database.

Various modifications of the invention in addition to those described herein will be apparent to those skilled in the art from the foregoing description. Such modifications are also intended to fall within the scope of the appended claims. Each reference (including but not limited to journal articles, U.S. and non-U.S. patents patent application publications, international patent application publications, gene bank accession numbers and the like) cited in the present application is incorporated herein by reference in its entirety. Those skilled in the art will appreciate that numerous changes and modifications may be made to the embodiments of the invention and that such changes and modifications may be made without departing from the scope of the invention. It is therefore intended that the appended claims cover all such equivalent variations as fall within the true scope of the invention.

What is claimed is:

1. A method comprising:

contacting a sample of nucleic acid with a reaction mixture comprising a set of oligonucleotide primers, one or more polymerase enzymes, and one or more water-in-oil emulsion-forming components wherein said emulsion-forming components comprise polysorbate 40 and polydimethylsiloxane such that said sample and said reaction mixture form an emulsion;

subjecting said emulsion to a multiple displacement amplification reaction comprising thermocycling the emulsion, wherein a nucleic acid sequence in said sample is amplified within at least one emulsion microdroplet to produce at least one multiple displacement amplification product; and converting said emulsion to aqueous and hydrophobic phases upon completion of said multiple displacement amplification reaction by adding an emulsion-breaking compound that is chloroform to said reaction.

2. The method of claim 1 wherein said reaction mixture further comprises betaine, trehalose, or both betaine and trehalose.

3. The method of claim 2 wherein said betaine is present in said reaction mixture at a concentration between about 0.2 M to about 1.6 M.

4. The method of claim 2 wherein said trehalose is present in said reaction mixture at a concentration between about 0.1 M and 1.0 M.

5. The method of claim 4 wherein said one or more polymerase enzymes comprise Phi29 polymerase, Bst DNA polymerase, and/or Pol I polymerase.

6. The method of claim 5 wherein said reaction mixture further comprises between about 0.2 units/μL to about 0.6 units/μL of Phi29 polymerase, if said Phi29 polymerase is present in said reaction mixture.

7. The method of claim 5 wherein said reaction mixture further comprises between about 0.005 units/μL to about 0.015 units/μL of Pol I polymerase, if said Pol I polymerase is present in said reaction mixture.

8. The method of claim 1 wherein said one or more polymerase enzymes comprise 5'→3' DNA polymerase activity, 3'→5' exonuclease activity, and/or 5'→3' excision repair activity.

9. The method of claim 1 further comprising amplifying a targeted segment of said amplified product to obtain a second amplification product.

10. The method of claim 9 further comprising determining the base composition of said second amplification product with the proviso that sequencing of said second amplification product is not performed to determine said base composition.

11. The method of claim 10 wherein said base composition of said second amplification product is determined by mass spectrometry.

12. The method of claim 9 further comprising determining the sequence of said second amplification product.

13. The method of claim 1 wherein said polysorbate 40 is 1% polysorbate 40 (w/v).

14. The method of claim 1 wherein said reaction mixture further comprises dimethyl sulfoxide (DMSO).

15. The method of claim 14 wherein said dimethyl sulfoxide (DMSO) is 2.5% dimethyl sulfoxide (DMSO).

16. The method of claim 1 wherein bovine serum albumin (BSA) is not included in said reaction mixture.

* * * * *